(12) United States Patent
Van Eck et al.

(10) Patent No.: US 9,115,338 B2
(45) Date of Patent: Aug. 25, 2015

(54) ENHANCEMENT OF BETA-CAROTENE CONTENT IN PLANTS

(75) Inventors: Joyce Van Eck, Ithaca, NY (US); David F. Garvin, Roseville, MN (US)

(73) Assignees: Boyce Thompson Institute for Plant Research, Ithaca, NY (US); The United States of America, as represented by the Secretary of Agriculture, Washington, DC (US)

( * ) Notice: Subject to any disclaimer, the term of this patent is extended or adjusted under 35 U.S.C. 154(b) by 1533 days.

(21) Appl. No.: 11/722,244

(22) PCT Filed: Dec. 19, 2005

(86) PCT No.: PCT/US2005/045640
§ 371 (c)(1),
(2), (4) Date: Jun. 9, 2008

(87) PCT Pub. No.: WO2006/068946
PCT Pub. Date: Jun. 29, 2006

(65) Prior Publication Data
US 2008/0276331 A1   Nov. 6, 2008

Related U.S. Application Data

(60) Provisional application No. 60/638,085, filed on Dec. 20, 2004.

(51) Int. Cl.
| | |
|---|---|
| C12N 15/82 | (2006.01) |
| C12N 5/14 | (2006.01) |
| A01H 5/00 | (2006.01) |
| A01H 5/08 | (2006.01) |
| A01H 5/10 | (2006.01) |
| C12N 9/02 | (2006.01) |

(52) U.S. Cl.
CPC ............ *C12N 9/0071* (2013.01); *C12N 9/0004* (2013.01); *C12N 15/825* (2013.01); *C12N 15/8243* (2013.01)

(58) Field of Classification Search
USPC ................... 370/442–443, 458; 455/450–453
See application file for complete search history.

(56) References Cited

U.S. PATENT DOCUMENTS 6,232,530 B1 * 5/2001 DellaPenna et al. .......... 800/282

OTHER PUBLICATIONS

Rissler, H. et al. Photosynthesis Research (2001); vol. 67, pp. 127-137.*
Varsha-Wesley, S. et al. The Plant Journal (2001) vol. 27(6), pp. 581-590.*
Romer, S. et al. Metabolic Engineering (2002); vol. 4 pp. 263-272.*
Stalberg, K. et al. Planta (1996) vol. 199; pp. 515-519.*
Lindstrom, J. et al. Developmental Genetics (1990) vol. 11, pp. 160-167.*
Rissler et al, 2001, Photosynthesis Res., 67:127-137.*
Romer et al, 2002, Metabolic Engineering, 4:263-272.*
Varsha-Wesley et al, 2001, The Plant J., 27:581-590.*
Rissler et al., "Antisense Inhibition of the Beta-carotene Hydroxylase Enzyme in *Arabidopsis* and the Implications for Carotenoid Accumulation, Photoprotection and Antenna Assembly," Photosynthesis Research. 67:127-137 (2001).
Davidson et al., "Overexpression of Beta-carotene Hydroxylase Enchances Stress Tolerance in *Arabidopsis*," Nature. 418:203-206 (2002).
Romer et al., "Genetic Engineering of a Zeaxanthin-rich Potato by Antisense Inactivation and Co-suppression of Carotenoid Epoxidation," Metabolic Engineering. 4:263-272 (2002).
Tian et al., "Functional Analysis of Beta- and Epsilon-Ring Carotenoid Hydroxylases in *Arabidopsis*," Plant Cell 15:1320-1332 (2003).
International Search Report and Written Opinion for corresponding PCT/US05/45640 (Jan. 3, 2007).

* cited by examiner

*Primary Examiner* — Russell Kallis
*Assistant Examiner* — Jason Deveau Rosen
(74) *Attorney, Agent, or Firm* — LeClairRyan, a Professional Corporation

(57) ABSTRACT

The present invention relates to a nucleic acid construct having a nucleic acid molecule configured to silence β-carotene hydroxylase expression, and host cells, expression systems, plants, and plant seeds having the nucleic acid construct. The present invention also relates to a method of enhancing beta-carotene content by growing a transgenic plant from a plant or seed transformed with the construct.

45 Claims, 9 Drawing Sheets

>EST416911 BE472058 cSTA31B10
On chromosome 6 (RNAi construct based on this gene)

GGGAGTNGGGGNTNTGGTTACTGAATAAGTATTACTCCTCGCGCGGNGCC
GGCCGCTCTAGAACTAGTGGATCCCCGGGCTGCAGGAATTCGGCACGAG
GCTAAATTGGTCATCCCCACAATCAATGGCTGCCGCCGCCAGAATTTCCGC
CTCTTCTACTTCAGGAACAATTTTTTTCCGTCATACTCCGTTTCTTGGCCCAA
AACCCACTTCAACAACCTCACATGTTTCTCCAATCTCTCCTTTTTCTCCTAAT
CTAGGCCCAATTCTGAGGTCTAGAAGAAAACCCAGTTTCACTG
TTTGCTTTGTTCTCGAGGATGAGAAGCTGAAACCTCAATTTGAGGATGAGGC
AGAGGATTTTGAAAAGAAGATTGAGGAACAGATCTCAGCTACACGCTTGGT
GGAAAAATTGGCTAGGAAGAAATCGGAGAGGTTTACTTATCTTGTAGCTGCT
GTAATGTCTAGTTTTGGGATTACTTCTATGGCTGTTATGGCGGTTTATTACAG
ATTTTCGTGGCAAATGGAGGGTGGAGAAGTTCCTTTAACCGAAATGTTGGG
TACATTTGCTCTCTCTGTTGGTGCTGCTGTAGGAATGGAGTTTTGGGCAAGA
TGGGCACACAAAGCATTGTGGCATGCTTCACTATGGCACATGCACGAGTCA
CATCACAAACCAAGAGAAGGACCTTTTGAGCTGAATGACGTTTTCGCCATAA
CAAACGCTGTTCCAGCAATAGCCCTCCTCAACTATGGTTTTTTCCACAAAAG
CCTCATTCCTTGGGCTATGCTTCCGCGCTTGGGCTAGGGATCACAGTATTT
GGAATGGCATACATGTTCGTTCACCATGGG

FIGURE 1A

>EST343470 AW907347 cSTA6D9
On chromosome 3

GGAAGAGAGTTTTNAANAATGGATAACATGCTGGAGCTCCACCTGAGTGGC
GTCCGCTCTAGAACTAGTGGATCCCCCGGGCTGCAGGAATTGGCACGAGG
ATTTCCTTAAATTGCCCCTCAACTGCCATCACTCCACTCCTCTCTACCAACTC
TGAGAGAGAGTCTAAATTGGTCATCCCCACAATCAATGGCTGCCGCCGCCA
GAATTTCCGCCTCTTCTACTTCAGGAACAATTTTTTTTCCGTCATACTCCGTTT
CTTGGCCCAAAACCCACTTCAACAACCTCACATGTTTCTCCAATCTCTCCTTT
TTCTCCTAATCTAGGCCCAATTCTGAGGTCTAGAAGAAAACCCAGTTTC
ACTGTTTGCTTTGTTCTCGAGGATGAGAAGCTGAAACCTCAATTTGAGGATG
AGGCAGAGGATTTTGAAAAGAAGATTGAGGAACAGATCTCAGCTACACGCT
TGGTGGAAAAATTGGCTAGGAAGAAATCGGAGAGGTTTACTTATCTTGTAGC
TGCTGTAATGTCTAGTTTTGGGATTACTTCTATGGCTGTTATGGCGGTTTATT
ACAGATTTTCGTGGCAAATGGAGGGTGGAGAAGTTCCTTTAACCGAAATGTT
GGGTACATTTGCTCTCTCTGTTGGTGCTGCTGTANGAATGGAGTTTTGGGCA
AGATGGGCACACAAAGCATTGTGGCATTGCTCACTATGGCACATGCACGAG
TCACATCACAAACCAAGAGAAGGACCTTTTGAGCTGGATGACGTTTTCGCCA
TAACAAACGCTTGTCCAACAATAGCCCCTCCCAACTATGGTTTTTCCCAAAG
GGCCATTCCCTGGCTTTGCTTCGGCGCTGGGCTAGGATCACAGATTTGAAT
GGCTCCATGTCGTTCACGAAGGTGGTTCCCAAAAAATTCCGTTGACC

FIGURE 1B

The homology values were from comparisons at the nucleotide level.

Upper sequence = chromosome 6 BCH open reading frame
Lower sequence = chromosome 3 BCH open reading frame Score = 43.0 bits (22), Expect = 0.54
Identities = 66/88 (75%)
Strand = Plus / Plus

```
Query: 138 tctctccttttctcctaatctaggcccaattctgaggtctagaagaaaacccagtttca 197
           ||||||| ||  |||  ||| | ||| ||||| ||  |||| |||||||| || || ||
Sbjct: 107 tctctccgttaactcgcaattttggcgcaattttgctgtctcgaagaaagccgaggttgg 166

Query: 198 ctgtttgctttgttctcgaggatgagaa 225
           | |||||||||||| ||  || |||||||
Sbjct: 167 cggtttgctttgtgctgaagaatgagaa 194
```

Score = 367 bits (191), Expect = 8e-99
Identities = 269/308 (87%)
Strand = Plus / Plus

```
Query: 300 tggtggaaaaattggctaggaagaaatcggagaggtttacttatcttgtagctgctgtaa 359
           ||| |||||||||||| |||||||||||||||||||||||||||||||||| || ||||| |
Sbjct: 287 tggcggaaaaattggcgaggaagaaatcggagaggtttacttatcttgtggcggctgtca 346

Query: 360 tgtctagtttgggattacttctatggctgttatggcggtttattacagattttcgtggc 419
           |||||||||| ||||||||||||||||  || ||  ||||||||||||||||||||||| ||||
Sbjct: 347 tgtctagtttagggattacttctatggcgattttgtcagtttattacagattttcatggc 406

Query: 420 aaatggagggtggagaagttcctttaaccgaaatgttgggtacatttgctctctctgttg 479
           ||||||||||||||||||||| |||||  | |||||||| | ||||||  |||||| |||
Sbjct: 407 aaatggagggtggagaagtgccttttctgaaatgttagctacattcactctctcgtttg 466

Query: 480 gtgctgctgtaggaatggagttttgggcaagatgggcacacaaagcattgtggcatgctt 539
           | ||||| |||||||||||||    ||||| ||||||||| ||  || | ||||||||||
Sbjct: 467 gcgctgccgtaggaatggagtactgggcgagatgggctcatagagcactatggcatgctt 526

Query: 540 cactatggcacatgcacgagtcacatcacaaaccaagagaaggaccttttgagctgaatg 599
           |  ||||||||||||||||||||| || |  |||||||||||||||||||||| |||| |
Sbjct: 527 ctttatggcacatgcacgagtcacaccatagaccaagagaaggaccttttgagatgaacg 586

Query: 600 acgttttc 607
           ||||||||
Sbjct: 587 acgttttc 59
```

Beta-carotene content in transgenic potato lines.

| Plant Identification | Beta-carotene (µg/100 g fresh weight)** | Standard deviation |
|---|---|---|
| 91E22 wt* | 0 | 0 |
| 91E22/35S-33 | 2.574 | 4.459 |
| 91E22/35S-64 | 1.569 | 2.718 |
| 91E22/gbss-147 | 47.54 | 15.56 |
| 91E22/gbss-181 | 3.071 | 0.041 |
| 91E22/gbss-185 | 64.653 | 6.802 |
| 91E22/gbss-88 | 12.943 | 7.879 |
| | | |
| DES wt | 0 | 0 |
| DES/35S-107 | 0 | 0 |
| DES/35S-112 | 2.333 | 3.3 |
| DES/35S-130 | 1.622 | 2.294 |
| DES/35S-139 | 0 | 0 |
| DES/35S-154 | 0 | 0 |
| DES/35S-163 | Analysis in progress | - |
| DES/35S-172 | 0 | 0 |
| DES/35S-61 | 11.381 | 7.479 |
| DES/35S-79 | 0 | 0 |
| DES/35S-93 | 3.918 | 5.541 |
| DES/gbss-113 | 0 | 0 |
| DES/gbss-128 | 0 | 0 |
| DES/gbss-136 | 1.575 | 2.728 |
| DES/gbss-150 | 20.062 | 20.57 |
| DES/gbss-178 | 29.755 | 8.715 |
| DES/gbss-19 | 32.79 | 10.28 |
| DES/gbss-48 | 0 | 0 |
| DES/gbss-73 | 3.661 | 3.232 |
| DES/gbss-86 | 33.352 | 5.464 |
| DES/gbss-96 | 20.849 | 4.309 |
| DES control | 0 | 0 |
| | | |
| YDH wt | 1.314 | 1.382 |
| YDH/35S-11 | 330.512 | 6.653 |
| YDH/35S-118 | 9.527 | 2.083 |
| YDH/35S-35 | 67.898 | 13.089 |
| YDH/35S-41 | 93.485 | 14.81 |
| YDH/35S-56 | 137.553 | 23.386 |
| YDH/35S-71 | 142.793 | 23.458 |
| YDH/35S-73 | 74.528 | 3.595 |
| YDH/35S-9 | 123.373 | 10.326 |
| YDH/gbss-12 | 66.964 | 86.149 |
| YDH/gbss-18 | 210.629 | 8.984 |
| YDH/gbss-2 | 314.533 | 7.841 |
| YDH/gbss-21 | 239.379 | 27.977 |
| YDH/gbss-28 | 116.191 | 9.761 |

FIGURE 5

| | | |
|---|---|---|
| YDH/gbss-31 | 196.979 | 11.278 |
| YDH/gbss-36 | 165.251 | 8.992 |
| YDH/gbss-41 | 150.243 | 4.924 |
| YDH/gbss-45 | 247.248 | 42.309 |
| YDH/gbss-57 | 215.88 | 17.324 |
| YDH/gbss-6 | 205.825 | 38.011 |
| YDH/gbss-62 | 236.086 | 41.9 |
| YDH/gbss-80 | 7.031 | 5.69 |
| YDH/gbss-86 | 107.683 | 1.575 |
| YDH/gbss-93 | 4.679 | 6.618 |
| YDH/gbss-95 | 121.788 | 22.943 |
| YDH/control | 35.038 | 4.234 |

*wt indicates non-transgenic control
**Average of 3 different HPLC runs
***control indicates transgenics derived from construct without bch.

FIGURE 5 (cont.)

ENHANCEMENT OF BETA-CAROTENE CONTENT IN PLANTS

This application claims the benefit of U.S. Provisional Patent Application Ser. No. 60/638,085, filed Dec. 20, 2004.

FIELD OF THE INVENTION

The present invention relates to a nucleic acid construct configured for enhancement of beta-carotene content in plants.

BACKGROUND OF THE INVENTION

Carotenoids represent a diverse group of lipid-soluble pigments found in plants, algae, and in many bacteria and fungi, where they serve several purposes including light harvesting, protection against oxidative damage, and attractants to animals and insects for pollination and seed dispersal. Plant carotenoids are synthesized in chloroplasts of photosynthetic tissues, and in chromoplasts of fruits and flowers. In general, carotenoids are $C_{40}$ terpenoids that consist of eight isoprene units synthesized by the isoprenoid biosynthetic pathway. Significant progress has been made in elucidating the molecular biology of carotenoid biosynthesis, and genes encoding all of the enzymes that are thought to form the backbone of the carotenoids' pathway in plants have been cloned.

In addition to the functions they serve in plants, carotenoids also play an essential role in human nutrition. Beta-carotene is the most well-known carotenoid in the human diet because it is the principal carotenoid used by the body for the synthesis of vitamin A and, as such, is referred to as a provitamin A carotenoid. Vitamin A and its derivatives are important components of nutrition, vision, and cellular differentiation (von Lintig et al., "Filling the Gap in Vitamin A Research," *J. Biol. Chem.* 275:11915-11920 (2000)). Lack of vitamin A, especially in children, can lead to blindness (West, C. E., "Meeting Requirements for Vitamin A," *Nutr. Rev.* 58:341-345 (2000)). The World Health Organization reports that vitamin A deficiency is a public health problem in 118 countries. They estimate that between 100 and 140 million children are vitamin A deficient and that 250,000 to 500,000 of them become blind every year with one-half of them dying within 12 months of losing their sight. Death rates from common childhood infections such as diarrheal disease and measles increase in children who are vitamin A deficient.

In general, animals are unable to synthesize vitamin A de novo, and, therefore, diet provides the precursors—carotenoids, that are necessary for synthesis of this essential vitamin (von Lintig et al., "Filling the Gap in Vitamin A Research," *J. Biol. Chem.* 275:11915-11920 (2000); West, C. E., "Meeting Requirements for Vitamin A," *Nutr. Rev.* 58:341-345 (2000)). Sources of vitamin A in the diet include meat and dairy, and there is some fortification of foods. However, vitamin A can also be derived from the provitamin A carotenoids, namely beta-carotene. Though there is, in general, no lack of provitamin A compounds in the Western diet, in some underdeveloped countries the diet is lacking adequate supplies of vitamin A (West, C. E., "Meeting Requirements for Vitamin A," *Nutr. Rev.* 58:341-345 (2000)). Recent studies have shown that 21 μg of beta-carotene are required to provide 1 μg of retinol or one retinol equivalent of vitamin A.

In addition, in recent years, there have been reports on the health benefits of other carotenoids, namely lycopene and lutein, the intake of which have been shown to be associated with a decreased risk of various forms of cancer, coronary heart disease, and some degenerative diseases (Krinsky et al., "Biologic Mechanisms of the Protective Role of Lutein and Zeaxanthin in the Eye," *Annual Rev. Nutr.* 23:171-201 (2003); Mayne, S. T., "Beta-Carotene, Carotenoids and Disease Prevention in Humans," *FASEB J.* 10:690-701 (1996); Osganian et al., "Dietary Carotenoids and Risk of Coronary Artery Disease in Women," *Am. J. Clin. Nutr.* 77:1390-1399 (2003); Rock et al., "Update on the Biological Characteristics of the Antioxdant Micronutrients Vitamin C, Vitamin E, and the Carotenoids, *J. AM. Diet. Assoc.* 96:683-702 (1996)).

The potato (genus *Solanum*), which originated in the highlands of South America, has been a major food staple for 8,000 years. After wheat, maize, and rice, it is the fourth most important food crop worldwide, and nearly one-third of potato production is in developing countries. In potato tubers, there are two principal classes of pigments. Red, blue, and purple flesh tubers owe their color to anthocyanins, whereas tubers with yellow and orange flesh contain carotenoids (Brown et al., "Orange Flesh Trait in Potato: Inheritance and Carotenoid Content," *J. Amer. Soc. Hort. Sci.* 118:145-150 (1993)). The carotenoids that potato accumulates in greatest abundance are xanthophylls. Unlike beta-carotene, xanthophylls cannot be converted by the human body into vitamin A, and, thus, potato is a poor source of this vitamin. Interestingly, in certain potato lines one such xanthophyll that accumulates to high abundance is zeaxanthin, a derivative of beta-carotene that is formed when a hydroxyl group is added to beta-carotene through the activity of β-carotene hydroxylase. The gene encoding beta-carotene hydroxylase has been cloned from plants (Hirshberg, "Molecular Biology of Carotenoid Biosynthesis," in Britton, eds., *Carotenoids*, 3, Berlin:Birkhaeuser Verlag, pp. 149-194 (1998)).

The inventors postulated that high zeaxanthin potato lines possess the potential to accumulate large amounts of beta-carotene in their tubers, but do not do so because of the activity of beta-carotene hydroxylase. In theory, reducing beta-carotene hydroxylase activity in such potato tubers should result in the accumulation of beta-carotene because it is the immediate precursor of zeaxanthin. RNA silencing is a means of providing specific and heritable genetic interference through the introduction into a genome of double-stranded RNA-expressing constructs (Chuang et al., "Specific and Heritable Genetic Interference by Double-Stranded RNA in *Arabidopsis thaliana*," *Proc. Nat'l. Acad. Sci. USA* 97:4985-4990 (2000); Waterhouse, et al., "Exploring Plant Genomes by RNA-Induced Gene Silencing," *Nat. Rev. Genet.* 4:29-38 (2003)).

The enhancement of beta-carotene accumulation in the potato, by RNA silencing with the activity of β-carotene hydroxylase, provides the potential of increasing vitamin A intake in developing countries, and of providing a source for increased beta-carotene intake in Western diets.

The present invention is directed to overcoming these and other deficiencies in the art.

SUMMARY OF THE INVENTION

The present invention relates to a nucleic acid construct having a nucleic acid molecule configured to silence β-carotene hydroxylase expression. The construct also includes a 5' DNA promoter sequence and a 3' terminator sequence. The nucleic acid molecule, the promoter, and the terminator are operatively coupled to permit transcription of the nucleic acid molecule.

Another aspect of the present invention is a method of enhancing beta-carotene content. This method involves providing a transgenic plant or plant seed transformed with a nucleic acid construct having a nucleic acid molecule configured to silence β-carotene hydroxylase, a 5' DNA promoter sequence, and a 3' terminator sequence. The method involves growing the transgenic plant or a transgenic plant grown from the transgenic plant seed under conditions effective to enhance beta-carotene content of the transgenic plant or the plant grown from the transgenic plant seed.

The present invention also relates to an expression system, host cells, plant cells, plants, and plant seeds having a nucleic acid construct configured to silence β-carotene hydroxylase expression.

The present invention provides a strategy for modifying the provitamin A content of plants by relying, not on reconstructing the carotenoid pathway, but rather by mitigating the action of a single carotenogenic gene that is already expressed. The enhancement of beta-carotene accumulation in plants that express beta-carotene, by RNA silencing with the activity of β-carotene hydroxylase, provides the potential of increasing vitamin A intake in developing countries, and of providing a source for increased beta-carotene intake in Western diets.

The main advantage of the present invention is that an increase in beta-carotene resulted by simply "turning off" a gene as opposed to insertion of a foreign gene. Expression of proteins from foreign genes can sometimes adversely affect the growth, development, and fecundity of plants. Specifically targeting the expression of a single gene makes it less likely that the expression of other genes would be affected and result in undesirable affects. Another advantage is from the perspective of consumer acceptance. Consumers might be more accepting of a product in which an endogenous plant gene was silenced than a product containing a foreign gene.

BRIEF DESCRIPTION OF THE DRAWINGS

FIGS. 1A-C show nucleotide sequences encoding β-carotene hydroxylase of *Solanum tubersosum*. FIG. 1A shows the nucleotide sequence (SEQ ID NO: 2) on chromosome 6 encoding β-carotene hydroxylase, while FIG. 1B shows a nucleotide sequence (SEQ ID NO: 3) encoding β-carotene hydroxylase on chromosome 3. Homology between the two potato genes is approximately 75% near the 5' end, increasing to 87% further into the gene, as shown in FIG. 1C (SEQ ID NOs:49-52).

FIG. 2A is a map showing p35S-Cha vector construction. FIG. 2B is a map showing pG-Cha vector construction.

FIG. 5 shows the beta-carotene content in transgenic potato plants.

DETAILED DESCRIPTION OF THE INVENTION

Figure 2A:
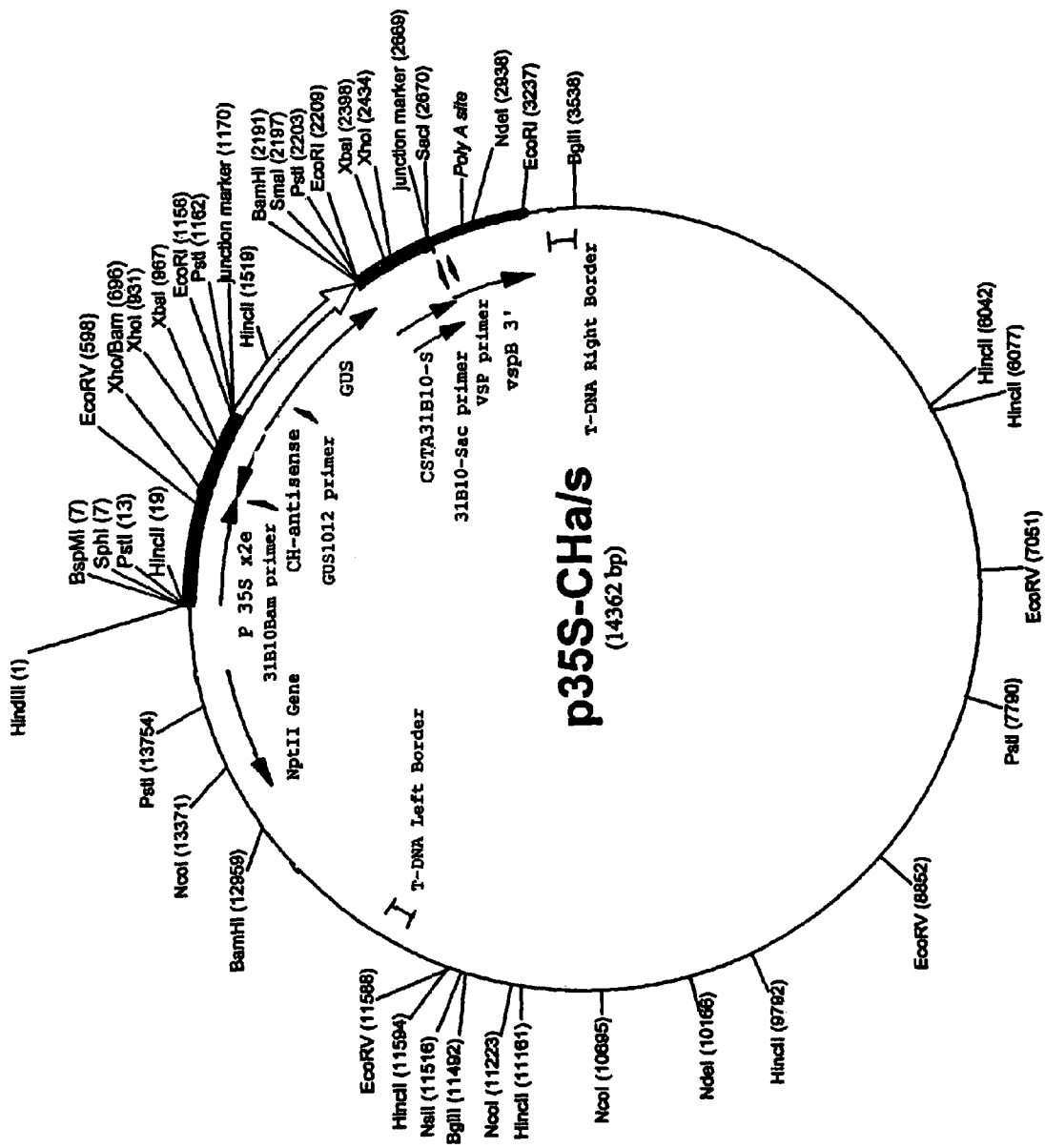
FIGS. 2A-B are maps of the plasmid vectors and orientations used in the present invention.

The present invention relates to a nucleic acid construct having a nucleic acid molecule configured to silence β-carotene hydroxylase expression. The construct also includes a 5' DNA promoter sequence and a 3' terminator sequence. The nucleic acid molecule, the promoter, and the terminator are operatively coupled to permit transcription of the nucleic acid molecule.

The β-carotene hydroxylase protein from potato (*Solanum tuberosum*) has an amino acid sequence of SEQ ID NO: 1 as follows:

```
Met Ala Ala Ala Ala Arg Ile Ser Ala Ser Ser Thr Ser Gly Thr Ile
 1               5                  10                  15

Tyr Phe Arg His Thr Pro Phe Leu Gly Pro Lys Pro Thr Ser Thr Thr
                20                  25                  30

Ser His Val Ser Pro Ile Ser Pro Phe Ser Pro Asn Leu Gly Pro Ile
            35                  40                  45

Leu Arg Ser Arg Arg Lys Pro Ser Phe Thr Val Cys Phe Val Leu Glu
        50                  55                  60

Asp Glu Lys Leu Lys Pro Gln Phe Glu Asp Glu Ala Glu Asp Phe Glu
65                  70                  75                  80

Lys Lys Ile Glu Glu Gln Ile Ser Ala Thr Arg Leu Ala Glu Lys Leu
                85                  90                  95

Ala Arg Lys Lys Ser Glu Arg Phe Thr Tyr Leu Val Ala Ala Val Met
            100                 105                 110

Ser Ser Phe Gly Ile Thr Ser Met Ala Val Met Ala Val Tyr Tyr Arg
        115                 120                 125

Phe Ser Trp Gln Met Glu Gly Gly Glu Val Pro Leu Thr Glu Met Leu
    130                 135                 140

Gly Thr Phe Ala Leu Ser Val Gly Ala Ala Val Gly Met Glu Phe Trp
145                 150                 155                 160

Ala Arg Trp Ala His Lys Ala Leu Trp His Ala Ser Leu Trp His Met
                165                 170                 175

His Glu Ser His His Lys Pro Arg Glu Gly Pro Phe Glu Leu Asn Asp
            180                 185                 190
```

```
Val Phe Ala Ile Thr Asn Ala Val Pro Ala Ile Ala Leu Leu Asn Tyr
            195                 200                 205

Gly Phe Phe His Lys Gly Leu Ile Pro Gly Leu Cys Phe Gly Ala Gly
        210                 215                 220

Leu Gly Ile Thr Val Phe Gly Met Ala Tyr Met Phe Val His Asp Gly
225                 230                 235                 240

Leu Val His Lys Arg Phe Pro Val Gly Pro Val Ala Asn Val Pro Tyr
                245                 250                 255

Leu Arg Lys Val Ala Ala Ala His Ser Leu His Ser Glu Lys Phe
                260                 265                 270

Asn Gly Val Pro Tyr Gly Leu Phe Leu Gly Pro Lys Glu Leu Glu Glu
            275                 280                 285

Val Gly Gly Thr Glu Glu Leu Glu Lys Glu Val Asn Arg Arg Thr Arg
    290                 295                 300

Leu Ser Lys Gly Ser
305
```

This protein is encoded by a gene found on chromosome 6 of potato (*Solanum tuberosum*) and has a nucleotide sequence of SEQ ID NO: 2, matching GenBank EST ID number EST416911 or *Solanum tuberosum* clone cSTA31B10 and mRNA sequence BE472058, as follows:

```
gggagtnggg gntntggtta ctgaataagt attactcctc gcgcggngcc ggccgctcta   60
gaactagtgg atcccccggg ctgcaggaat tcggcacgag gctaaattgg tcatccccac  120
aatcaatggc tgccgccgcc agaatttccg cctcttctac ttcaggaaca attttttttcc 180
gtcatactcc gtttcttggc ccaaaaccca cttcaacaac ctcacatgtt tctccaatct  240
ctccttttcc tcctaatcta ggcccaattc tgaggtctag aagaaaaccc agtttcactg  300
tttgctttgt tctcgaggat gagaagctga aacctcaatt tgaggatgag gcagaggatt  360
ttgaaaagaa gattgaggaa cagatctcag ctacacgctt ggtggaaaaa ttggctagga  420
agaaatcgga gaggtttact tatcttgtag ctgctgtaat gtctagtttt gggattactt  480
ctatggctgt tatggcggtt tattacagat tttcgtggca aatggagggt ggagaagttc  540
ctttaaccga aatgttgggt acatttgctc tctctgttgg tgctgctgta ggaatggagt  600
tttgggcaag atgggcacac aaagcattgt ggcatgcttc actatggcac atgcacgagt  660
cacatcacaa accaagagaa ggaccttttg agctgaatga cgttttcgcc ataacaaacg  720
ctgttccagc aatagccctc ctcaactatg gttttttcca caaaagcctc attccttggg  780
ctatgcttcc gcgcttgggc tagggatcac agtatttgga atggcataca tgttcgttca  840
ccatggg                                                            847
``` where n is any nucleotide.

Another β-carotene hydroxylase protein from potato (*Solanum tuberosum*) is encoded by a gene on chromosome 3 of potato (*Solanum tuberosum*) and has a nucleotide sequence of SEQ ID NO: 3, matching GenBank EST ID number EST343470 or *Solanum tuberosum* clone cSTA6D9 and mRNA sequence AW907347, as follows:

```
ggaagagagt tttnaanaat ggataacatg ctggagctcc acctgagtgg cgtccgctct   60
agaactagtg gatcccccgg gctgcaggaa ttggcacgag gatttcctta aattgcccct  120
caactgccat cactccactc ctctctacca actctgagag agagtctaaa ttggtcatcc  180
ccacaatcaa tggctgccgc cgccagaatt tccgcctctt ctacttcagg aacaattttt  240
```

```
ttccgtcata ctccgtttct tggcccaaaa cccacttcaa caacctcaca tgtttctcca  300
atctctcctt tttctcctaa tctaggccca attctgaggt ctagaagaaa acccagtttc  360
actgtttgct tgttctcga ggatgagaag ctgaaacctc aatttgagga tgaggcagag  420
gattttgaaa agaagattga ggaacagatc tcagctacac gcttggtgga aaaattggct  480
aggaagaaat cggagaggtt tacttatctt gtagctgctg taatgtctag ttttgggatt  540
acttctatgg ctgttatggc ggtttattac agatttcgt ggcaaatgga gggtggagaa  600
gttcctttaa ccgaaatgtt gggtacattt gctctctctg ttggtgctgc tgtangaatg  660
gagttttggg caagatgggc acacaaagca ttgtggcatt gctcactatg gcacatgcac  720
gagtcacatc acaaaccaag agaaggacct tttgagctgg atgacgtttt cgccataaca  780
aacgcttgtc caacaatagc ccctcccaac tatggttttt cccaaagggc cattccctgg  840
ctttgcttcg gcgctgggct aggatcacag atttgaatgg ctccatgtcg ttcacgaagg  900
tggttcccaa aaaattccgt tgacc                                       925
``` where n is any nucleotide.

Other plants with β-carotene hydroxylase genes include: *Arabidopsis*, barley, citrus, cotton, crocus, daffodil, grape, lettuce, marigold, maize, *Medicago truncatula*, onion, pepper, pine, potato, rice, *Sandersonia aurantiaca*, sorghum, soybean, tomato, *Brassica campestris* and wheat. Those plants with at least 50% homology at the protein level with potato β-carotene hydroxylase include: rice, citrus, *Arabidopsis*, daffodil, marigold, pepper, grape, crocus, and *Sandersonia aurantiaca*. Tomato is at least 90% homologous with potato β-carotene hydroxylase at the protein level.

The β-carotene hydroxylase from *Arabidopsis thaliana* has an amino acid sequence of SEQ ID NO: 4 as follows:

```
Met Ala Ala Gly Leu Ser Thr Ala Val Thr Phe Lys Pro Leu His Arg
 1               5                  10                  15

Ser Phe Ser Ser Ser Thr Asp Phe Arg Leu Arg Leu Pro Lys Ser
            20                  25                  30

Leu Ser Gly Phe Ser Pro Ser Leu Arg Phe Lys Arg Phe Ser Val Cys
            35                  40                  45

Tyr Val Val Glu Glu Arg Arg Gln Asn Ser Pro Ile Glu Asn Asp Glu
        50                  55                  60

Arg Pro Glu Ser Thr Ser Ser Thr Asn Ala Ile Asp Ala Glu Tyr Leu
65                  70                  75                  80

Ala Leu Arg Leu Ala Glu Lys Leu Glu Arg Lys Lys Ser Glu Arg Ser
                85                  90                  95

Thr Tyr Leu Ile Ala Ala Met Leu Ser Ser Phe Gly Ile Thr Ser Met
                   100                 105                 110

Ala Val Met Ala Val Tyr Tyr Arg Phe Ser Trp Gln Met Glu Gly Gly
               115                 120                 125

Glu Ile Ser Met Leu Glu Met Phe Gly Thr Phe Ala Leu Ser Val Gly
           130                 135                 140

Ala Ala Val Gly Met Glu Phe Trp Ala Arg Trp Ala His Arg Ala Leu
145                 150                 155                 160

Trp His Ala Ser Leu Trp Asn Met His Glu Ser His His Lys Pro Arg
                   165                 170                 175

Glu Gly Pro Phe Glu Leu Asn Asp Val Phe Ala Ile Val Asn Ala Gly
               180                 185                 190

Pro Ala Ile Gly Leu Leu Ser Tyr Gly Phe Phe Asn Lys Gly Leu Val
           195                 200                 205

Pro Gly Leu Cys Phe Gly Ala Gly Leu Gly Ile Thr Val Phe Gly Ile
       210                 215                 220

Ala Tyr Met Phe Val His Asp Gly Leu Val His Lys Arg Phe Pro Val
225                 230                 235                 240
```

```
Gly Pro Ile Ala Asp Val Pro Tyr Leu Arg Lys Val Ala Ala Ala His
                245                 250                 255

Gln Leu His His Thr Asp Lys Phe Asn Gly Val Pro Tyr Gly Leu Phe
                260                 265                 270

Leu Gly Pro Lys Glu Leu Glu Glu Val Gly Gly Asn Glu Glu Leu Asp
            275                 280                 285

Lys Glu Ile Ser Arg Arg Ile Lys Ser Tyr Lys Lys Ala Ser Gly Ser
        290                 295                 300

Gly Ser Ser Ser Ser Ser
305                 310
```

This protein is encoded by a protein having the nucleotide sequence of SEQ ID NO: 5 as follows:

```
atggcggcag gactctcaac cgccgttaca ttcaaaccac tccaccgctc tttctcctcc   60
tcctctaccg atttccgact ccgcctcccg aaatccttat ccggattctc tccgtctctt  120
cgatttaaac gcttttctgt ctgttacgtc gtcgaagaac ggagacagaa ttctccgatt  180
gagaacgatg agagaccgga gagcacgagc tccacaaacg ctatagacgc tgagtatctg  240
gcgttgcgtt tggcggagaa attggagagg aagaaatcgg agaggtccac ttatctaatc  300
gctgctatgt tgtcgagctt tggtatcact tctatggctg ttatggctgt tactacaga   360 ttctcttggc aaatggaggg aggtgagatc tcaatgttgg aaatgtttgg tacatttgct  420
ctctctgttg gtgctgctgt tggtatggaa ttctgggcaa gatgggctca tagagctctg  480
tggcacgctt ctctatggaa tatgcatgag tcacatcaca aaccaagaga aggaccgttt  540
gagctaaacg atgttttgc tatagtgaac gctggtccag cgattggtct cctctcttat   600
ggattcttca taaaggact cgttcctggt ctctgctttg gcgccgggtt aggcataacg   660
gtgtttggaa tcgcctacat gtttgtccac gatggtctcg tgcacaagcg tttccctgta  720
ggtcccatcg ccgacgtccc ttacctccga aaggtcgccg ccgctcacca gctacatcac  780
acagacaagt tcaatggtgt accatatgga ctgtttcttg gacccaagga attggaagaa  840
gttggaggaa atgaagagtt agataaggag attagtcgga gaatcaaatc atacaaaaag  900
gcctcgggct ccgggtcgag ttcgagttct tga                                933
```

The β-carotene hydroxylase from barley has an amino acid sequence of SEQ ID NO: 6 as follows:

```
Arg His Glu Ala Leu Gly Leu His His Gly Gln Leu Arg Arg Gln Glu
  1               5                  10                  15

Pro Ser Pro Arg Arg Ala Val Pro Asp Ala Ala Phe Pro Cys Arg
                20                  25                  30

Pro Ala Ser Pro Val Leu Pro Val His Ala Asp Gly Ala Gln Glu Gly
            35                  40                  45

Ala Arg Asp Arg Asp Val Leu Arg Pro Ala Gly Gly Ala Gly Ala Gly
        50                  55                  60

Pro Gly Ser Arg Ala Gly Ala Gly Asp Gly Ala Gly Ala Phe Ala Gly
 65                 70                  75                  80

Gly Arg Gly Gly Val Arg Gly Gly Ala Ala Arg Gly Gly Glu Glu Gly
                85                  90                  95

Ala Glu Ala Val Arg Glu Ala Asp Val Pro Gly Gly Arg Arg His Val
                100                 105                 110
```

```
Gln Pro Arg Gly His Leu His Gly His Arg Leu Arg Val Leu Pro Leu
        115                 120                 125
Arg Leu Ala Asn Gly Gly Arg Gly Ala Asp Arg Asp Ala Gly
    130                 135                 140
His Val Arg Ala Leu Arg Arg Arg Gly Arg Asp Gly Val Leu Gly
145                 150                 155                 160
Ala Val Gly Ala Gln Gly Ala Val Ala Arg Val Pro Val Ala His Ala
                165                 170                 175
Arg Val Ala Pro Pro Ala Ala Arg Arg Ala Leu Arg Ala Gln Arg Arg
                180                 185                 190
Leu Arg His His Gln Arg Arg Ala Gly His Arg Pro Pro Arg Leu Arg
                195                 200                 205
Leu Leu Pro Pro Arg Pro Arg Pro Arg Pro Leu Leu Arg Arg Gly Pro
        210                 215                 220
Trp Asp Tyr Ala Phe Arg Asp Gly Ile His Val Arg Pro Arg Arg Pro
225                 230                 235                 240
Gly Pro Pro Pro Leu Pro Arg Arg Pro His Arg Arg Ala Leu Leu
                245                 250                 255
Pro Ala Ser Gly Cys Arg Ser Gln Asp Thr Pro His Gly Gln Val Arg
                260                 265                 270
Gly Arg Thr Val Trp Ala Leu Pro Gly Thr Gln Gly Ala Gly Gly Arg
            275                 280                 285
Trp Trp Pro Arg Arg Ala Gly Ala Gly Ala Arg Gln Asn Gln Pro Asp
        290                 295                 300
Ser Glu His Leu Ser Ser Gly His Gly Val Ala Ala Tyr Ala Ala Arg
305                 310                 315                 320
Arg Thr Leu
```

35

The protein is encoded by a nucleotide acid having a nucleotide sequence of SEQ ID NO: 7 as follows:

```
cggcacgagg ctctcgggct ccaccatggc cagcttcgcc gtcaagaacc ctctcctcgc   60
cgccgcgcg taccggacgc tgccttcccg tgccggccgg cctctcccgt tctccccgtt  120
cacgcggacg gcgcgcagga gggggcaaga gaccgtgacg tgcttcgtcc cgcaggaggg  180
gcaggcgccg ggcccggctc ccgtgccgga gccggcgacg gtgccggtgc cttcgctgga  240
ggaagaggcg gcgtccgcgg cggcgcggcg cgtggcggag aggaaggcgc ggaagcagtc  300
cgagaggcgc acgtacctgg tggccgcccgt catgtccagc ctaggggtca cctccatggc  360
catcgcctcc gtgtactacc gcttcgcctg gcaaatggag ggcggcgagg tgccgatgac  420
cgagatgctg ggcacgttcg cgctctccgt cggcgcggcg gtcgggatgg agttctgggc  480
gcagtgggcg cacaaggcgc tgtggcacgc gtccctgtgg cacatgcacg agtcgcacca  540
ccggccgcgc gacgggccct cgagctcaa cgacgtcttc gccatcatca acgccgtgcc  600
ggccatcgcc ctcctcgcct acggcttctt ccaccgcggc ctcgtccccg gcctctgctt  660
cggcgcgggc cttgggatta cgcttttcgg gatggcatac atgttcgtcc acgacggcct  720
ggtccaccgc cgcttcccccg tcggccccat cgccgacgtg ccctacttcc ggcgagtggc  780
tgccgctcac aagatacacc acatggacaa gttcgagggc gtaccgtatg ggctcttcct  840
gggacccaag gagctggagg acgttggtgg cctcgacgag ctggagcagg agctcgccag  900
aatcaaccgg actcggagca tctgagctct ggacatggcg tggcggcata tgcagctaga  960
agaaccttgt g                                                     971
```

The β-carotene hydroxylase protein from *Brassica campestris* has an amino acid sequence of SEQ ID NO: 8 as follows:

```
Met Ala Ala Gly Leu Ser Thr Thr Val Thr Phe Asn Pro Leu His Arg
 1               5                   10                  15

Ser Phe Ser Ser Ser Ser Val Arg Leu His His Pro Arg Ser Leu
                20                  25                  30

Thr Gly Leu Pro Ser Ser Leu Arg Phe Arg Gly Phe Ser Val Cys Tyr
            35                  40                  45

Val Val Glu Glu Gln Arg Gln Ser Ser Pro Val Asp Asn Asp Glu Arg
        50                  55                  60

Pro Glu Arg Thr Asn Val Ile Asp Pro Glu Leu Leu Ala Leu Arg Leu
 65                 70                  75                  80

Ala Glu Lys Leu Glu Arg Lys Lys Ser Glu Arg Phe Thr Tyr Leu Ile
                85                  90                  95

Ala Ala Val Met Ser Ser Phe Gly Ile Thr Ser Met Ala Val Met Ala
                100                 105                 110

Val Tyr Tyr Arg Phe Ser Trp Gln Met Glu Gly Val Ile Pro Met
        115                 120                 125

Ser Glu Met Phe Gly Thr Phe Ala Leu Ser Val Gly Ala Ala Val Gly
    130                 135                 140

Met Glu Phe Trp Ala Arg Trp Ala His Arg Ala Leu Trp His Ala Ser
145                 150                 155                 160

Leu Trp Asn Met His Glu Ser His His Lys Pro Arg Glu Gly Pro Phe
                165                 170                 175

Glu Leu Asn Asp Val Phe Ala Ile Ile Asn Ala Val Pro Ala Ile Gly
            180                 185                 190

Leu Leu Ser Tyr Gly Phe Phe Asn Lys Gly Leu Val Pro Gly Leu Cys
        195                 200                 205

Phe Gly Ala Gly Leu Gly Ile Thr Val Phe Gly Ile Ala Tyr Met Phe
    210                 215                 220

Val His Asp Gly Leu Val His Lys Arg Phe Pro Val Gly Pro Ile Ala
225                 230                 235                 240

Asp Val Pro Tyr Leu Arg Lys Val Ala Ala Ala His Gln Leu His His
                245                 250                 255

Thr Asp Lys Phe Asp Gly Val Pro Tyr Gly Leu Phe Leu Gly Pro Lys
                260                 265                 270

Glu Leu Glu Glu Val Gly Gly Asp Glu Glu Leu Asp Lys Glu Ile Ser
            275                 280                 285

Arg Arg Ile Lys Leu Tyr Lys Lys Ser Ser Ser Ser
 290                 295                 300
```

This protein is encoded by a nucleic acid having a nucleotide sequence of SEQ ID NO: 9 as follows:

```
atggcggcag gtctctcaac caccgtaaca ttcaaccctc tccaccgctc tttctcatcc    60
tcctcaagtg tccgcttaca ccacccaaga tccttaaccg gactcccttc atctctccgg   120
ttcagaggct tctcggtctg ctacgtcgtc gaggagcaga ggcagagctc tcccgtcgac   180
aacgatgaaa gacctgagag aaccaacgtc atagatcccg agctcttggc tttgcgtttg   240
gctgagaagt tggagaggaa gaagtccgag aggttcactt atctaatagc agctgtgatg   300
tcgagctttg gtatcacttc catggccgtt atggccgttt actacagatt ctcttggcaa   360
atggagggag gtgtgatccc aatgtcagag atgttcggta catttgctct ctctgttggt   420
```

-continued

```
gctgctgtgg gcatggagtt tgggcaaga tgggctcata gagctctctg gcacgcttct    480
ctttggaata tgcatgagtc acatcacaaa ccaagagaag gtcccttga gctgaacgat    540 gtgtttgcaa ttataaacgc tgttcctgcg attggtctcc tttcttatgg tttcttcaat    600
aaaggactcg tccctggtct ttgctttggc gccggactag gaataacggt gtttgggatc    660
gcctatatgt ttgtccacga tggtttggtg cacaagcgtt tccctgtagg tcccatcgct    720
gatgtcccct tatctccgaa ggtcgctgcc gctcaccagc tacatcacac tgacaagttc    780
gatggtgtgc catatggact gtttcttgga ccaaaggaat tggaagaagt tggaggagat    840
gaagagttag acaaggagat tagtcggaga atcaaattat acaaaaagag ttcgagctct    900
```

The β-carotene hydroxylase protein from citrus has an amino acid sequence of SEQ ID NO: 10 as follows:

```
Met Ala Val Gly Leu Leu Ala Ala Ile Val Pro Lys Pro Phe Cys Leu
 1               5                  10                  15

Leu Thr Thr Lys Leu Gln Pro Ser Ser Leu Thr Thr Lys Pro Ala
                20                  25                  30

Pro Leu Phe Ala Pro Leu Gly Thr His His Gly Phe Phe Asn Gly Lys
            35                  40                  45

Asn Arg Arg Lys Leu Asn Ser Phe Thr Val Cys Phe Val Leu Glu Glu
 50                  55                  60

Lys Lys Gln Ser Thr Gln Ile Glu Thr Phe Thr Asp Glu Glu Glu
 65                  70                  75                  80

Glu Ser Gly Thr Gln Ile Ser Thr Ala Ala Arg Val Ala Glu Lys Leu
                85                  90                  95

Ala Arg Lys Arg Ser Glu Arg Phe Thr Tyr Leu Val Ala Ala Val Met
                100                 105                 110

Ser Ser Phe Gly Ile Thr Ser Met Ala Val Met Ala Val Tyr Tyr Arg
            115                 120                 125

Phe Trp Trp Gln Met Glu Gly Gly Glu Val Pro Leu Ala Glu Met Phe
        130                 135                 140

Gly Thr Phe Ala Leu Ser Val Gly Ala Ala Val Gly Met Glu Phe Trp
145                 150                 155                 160

Ala Arg Trp Ala His Lys Ala Leu Trp His Ala Ser Leu Trp His Met
                165                 170                 175

His Glu Ser His His Arg Pro Arg Glu Gly Pro Phe Glu Leu Asn Asp
            180                 185                 190

Val Phe Ala Ile Ile Asn Ala Val Pro Ala Ile Ala Leu Leu Ser Phe
            195                 200                 205

Gly Phe Phe His Lys Gly Leu Val Pro Gly Leu Cys Phe Gly Ala Gly
        210                 215                 220

Leu Gly Ile Thr Val Phe Gly Met Ala Tyr Met Phe Val His Asp Gly
225                 230                 235                 240

Leu Val His Lys Arg Phe Pro Val Gly Pro Ile Ala Asp Val Pro Tyr
                245                 250                 255

Phe Arg Arg Val Ala Ala Ala His Gln Leu His His Ser Asp Lys Phe
            260                 265                 270

His Gly Val Pro Tyr Gly Leu Phe Leu Gly Pro Lys Glu Leu Glu Glu
            275                 280                 285

Val Gly Gly Leu Glu Glu Leu Glu Lys Glu Ile Ser Lys Arg Ile Lys
        290                 295                 300

Ser Tyr Asn Arg Val Pro Lys
305                 310
```

This protein is encoded by a nucleic acid molecule having a nucleotice sequence of SEQ ID NO: 11 as follows:

```
atggcggtcg gactattggc cgccatagtc ccgaagccct tctgtctcct cacaacaaaa    60
cttcaaccct cttcgctcct cacaacaaaa cctgctcccc tttttgcccc cgccacggct   120
tctttaatgg caaaaaccga agaaaaatca actctttcac cgtatgtttt gttttagagg   180
agaaaaaaca aagcacccag atcgagactt tcacggagga ggaggaggag gagtcgggta   240
cccagatctc gactgctgcc cgcgtggccg agaaattggc gagaaagaga tccgagaggt   300
tcacttatct cgttgctgcc gtcatgtcta gttttggtat cacttccatg gctgtcatgg   360
ctgtttatta caggttctgg tggcaaatgg agggtggaga gctgaaatgt ttggcacatt   420
tgctctctct gttggtgctg ctgtgggcat ggagttttgg gcacgatggg ctcataaagc   480
tctgtggcat gcttctttat ggcatatgca cgagtctcac catcgaccaa gagagggtcc   540
ttttgagcta aacgatgtgt tgccataat caacgcagtt ccagccatag cccttctctc   600
ttttggcttc ttccacaaag gccttgtacc tggtctctgt tttggtgctg gacttggcat   660
tacggtgttt gggatggcct acatgttcgt ccacgatggt ctcgttcaca aaggttccc   720
tgtgggtccc attgccgacg tgccttattt ccggagagtc gctgcggctc accagcttca   780
ccactcggat aaattccacg tgttccata tgggctcttt ctcggaccta aggagcttga   840
agaagtgggg ggactagaag aattggagag gagatcagta agagaatcaa atcatacaac   900
agggttccaa aa                                                       912
```

See Kim, I.-J. et al., "Isolation and Characterization of cDNAs Encoding Beta-carotene Hydroxylase in Citrus," *Plant Sci.* 161(5):1005-1010 (2001), which is hereby incorporated by reference in its entirety.

The β-carotene hydroxylase protein from cotton has an amino acid sequence of SEQ ID NO: 12 as follows:

```
Met Ala Val Gly Leu Ser Ala Ala Val Thr Pro Lys Pro Phe Arg Ser
 1               5                  10                  15

Phe Pro Leu Leu Lys Pro Ala Pro Ile Phe His Pro Leu Leu His Leu
                20                  25                  30

Pro Lys Thr Thr Thr Tyr Ala Ala Arg Arg Lys Lys Ser Phe Ala Val
            35                  40                  45

Cys Phe Val Val Asp Glu Glu Gln Lys Gln Ser Ala Pro Thr Gln Ile
        50                  55                  60

Val Glu Gln Gly Phe Glu Asp Ala Arg Asp Arg Gln Ile Leu Ile Pro
 65                  70                  75                  80

Ser Arg Leu Ser Glu Lys Leu Ala Arg Lys Arg Ser Glu Arg Phe Thr
                85                  90                  95

Tyr Leu Val Ala Ala Val Met Ser Ser Phe Gly Ile Thr Ser Met Ser
                100                 105                 110

Val Met Ala Val Tyr Tyr Arg Phe Trp Trp Gln Met Glu Gly Gly Glu
            115                 120                 125

Val Pro Leu Ser Glu Met Phe Gly Thr Phe Thr Leu Ala Val Gly Ala
        130                 135                 140

Ala Val Gly Met Glu Phe Trp Ala Arg Trp Ala His Arg Ala Leu Trp
145                 150                 155                 160

His Ala Ser Leu Trp His Met His Glu Ser His His Arg Pro Arg Glu
                165                 170                 175

Gly Pro Phe Glu Leu Asn Asp Val Phe Ala Ile Thr Asn Ala Val Pro
                180                 185                 190
```

-continued

```
Ala Ile Ala Leu Leu Ser Tyr Gly Phe Phe Asn Lys Gly Leu Val Pro
            195                 200                 205

Gly Leu Cys Phe Gly Ala Gly Leu Gly Ile Thr Met Phe Gly Met Ala
            210                 215                 220

Tyr Met Phe Val His Asp Gly Leu Val His Lys Arg Phe Pro Val Gly
225                 230                 235                 240

Pro Ile Ala Asn Val Pro Tyr Phe Arg Lys Val Ala Ala His Gln
                245                 250                 255

Leu His His Ser Glu Lys Phe Asn Gly Val Pro Tyr Gly Leu Phe Leu
            260                 265                 270

Gly Pro Lys Glu Val Glu Asp Val Gly Gly His Glu Glu Leu Glu Lys
            275                 280                 285

Glu Ile Asn Arg Arg Ile Lys Ser Ser Lys Gly Ser
290                 295                 300
```

This protein is encoded by a nucleic acid molecule having the nucleotide sequence of SEQ ID NO: 13 as follows:

```
atggcggttg gcttatccgc cgccgtaact cctaaaccct tccgctcatt tccgctgctg    60
aagcctgcgc caattttcca tcctttactg cacctcccaa aaacaacaac ctacgcagct   120
cgaagaaaga aaagctttgc tgtttgtttc gtggtggatg aagaacagaa gcagagcgct   180
cctacccaga tcgtggaaca aggattcgag gatgctagag atcgtcagat cttaataccg   240
tcgcgtctgt cggagaaatt agctagaaag agatccgaaa ggtttactta cctcgttgcc   300
gctgtcatgt ctagctttgg gattacatcc atgtctgtta tggccgttta ttacaggttt   360
tggtggcaaa tggagggagg agaggtgcct ctttctgaaa tgttcggcac atttactta   420
gcagtcggtg ccgctgtggg catggagttt tgggctagat gggctcacag agctctctgg   480
cacgcatcgt tatggcatat gcacgagtca caccatcgac ccagagaagg accgttcgag   540
ctaaacgatg tgttcgccat aaccaacgcc gtcccagcaa ttgctcttct ctcgtatggt   600
ttcttcaaca aaggccttgt acctggtcta tgtttcggtg ctgggcttgg tataacgatg   660
tttggaatgg cttatatgtt cgtccacgat ggtctcgtcc ataagagatt ccccgtaggc   720
cctatcgcca acgtgcctta cttcaggaag gttgctgcgg ctcaccagct ccatcattca   780
gaaaaattca atggtgttcc atatgggctg tttctagggc cgaaggaagt ggaggatgtg   840
ggaggacatg aagaattgga gaagaaatc aacaggagaa tcaaatcaag caaaggttcc   900
```

The β-carotene hydroxylase protein from crocus has an amino acid sequence of SEQ ID NO: 14 as follows:

```
Met Ser Ala Lys Ile Ser Pro Ser Ala Thr Thr Leu Ala Ala Ser Phe
1                   5                  10                  15

Arg Arg Pro Pro Ser Gly Ala Arg Ile Ile Leu Leu Ser Ser Leu Pro
            20                  25                  30

Val Arg Arg Pro Val Glu Arg Ile Arg Pro Pro Leu Leu His Arg
            35                  40                  45

Arg Arg Arg Thr Ala Thr Val Phe Phe Val Leu Ala Glu Glu Lys Thr
        50                  55                  60

Thr Pro Phe Leu Asp Asp Val Glu Glu Glu Lys Ser Ile Ala Pro Ser
65                  70                  75                  80

Asn Arg Ala Ala Glu Arg Ser Ala Arg Lys Arg Ser Glu Arg Thr Thr
            85                  90                  95
```

-continued

```
Tyr Leu Ile Thr Ala Val Met Ser Ser Phe Gly Ile Thr Ser Met Ala
            100                 105                 110
Ala Ala Ala Val Tyr Tyr Arg Phe Ala Trp Gln Met Glu Gly Gly Asp
            115                 120                 125
Val Pro Val Thr Glu Met Ala Gly Thr Phe Ala Leu Ser Val Gly Ala
            130                 135                 140
Ala Val Gly Met Glu Phe Trp Ala Arg Trp Ala His Arg Ala Leu Trp
145                 150                 155                 160
His Ala Ser Leu Trp His Met His Glu Ser His His Arg Pro Arg Glu
                165                 170                 175
Gly Pro Phe Glu Leu Asn Asp Val Phe Ala Ile Asn Ala Val Pro
            180                 185                 190
Ala Ile Ala Leu Leu Asn Phe Gly Phe Phe His Arg Gly Leu Leu Pro
            195                 200                 205
Gly Leu Cys Phe Gly Ala Gly Leu Gly Ile Thr Leu Phe Gly Ile Ala
            210                 215                 220
Tyr Met Phe Val His Asp Gly Leu Val His Arg Arg Phe Pro Val Gly
225                 230                 235                 240
Pro Ile Ala Asp Val Pro Tyr Phe Gln Arg Val Ala Ala Ala His Gln
            245                 250                 255
Ile His His Ser Glu Lys Phe Glu Gly Val Pro Tyr Gly Leu Phe Met
            260                 265                 270
Gly Pro Lys Glu Leu Glu Glu Ile Gly Gly Leu Lys Glu Leu Glu Lys
            275                 280                 285
Glu Val Ser Arg Arg Ile Lys Ala Tyr Asn Asn Ser Ala Glu Ile Lys
            290                 295                 300
Thr
305
``` protein is encoded by a nucleic acid molecule having a nucleotide sequence of SEQ ID NO: 15 as follows:

```
atgtcggcca aaatctcccc ctccgccacc accctcgccg cctccttccg ccgccctccg    60
tccggcgcac gcatcatcct cctctcttcg ctccctgtcc gccgcccgt cgaacgtcga    120
atccggccgc cgttgcttca tcgtcggcgt cggacggcga cagtgttttt cgttctcgcc   180
gaagaaaaaa caactccttt tcttgacgat gtggaggaag agaagagtat tgcgccgtca    240
aatcgggcgg ctgagaggtc ggcgcggaag cggtcggagc ggaccacgta cctcatcacg    300
gcggttatgt cgagcttcgg catcacatcc atggccgccg ccgccgtcta ctaccgcttc    360
gcttggcaaa tggagggagg ggatgtgcca gtgacgagat ggcgggaac gttcgctctc    420
tcggtcgggg cggccgtggg gatggagttc tgggccaggt gggcccaccg ggcactctgg    480
cacgcgtcgc tctggcacat gcacgagtcc caccaccggc cgagggaggg cccttcgag    540
ctcaacgacg tcttcgccat aatcaacgcg gtccccgcca tcgccctcct caacttcggc    600
ttcttccaca gaggtctcct ccccggcctc tgtttcggcg ccgggctggg gatcacgctg    660
tttggtatig cgtacatgtt cgtccacgac gggctagtcc accggcggtt ccctgtgggg    720
cccatcgccg acgtgcccta cttccagcgc gtcgccgctg ctcaccagat ccaccactcg    780
gagaagttcg aagggggtgcc ctatggactg ttcatgggc ccaaggaatt ggaggagatt    840
ggtggattaa aagagctgga gaaggaggtg agcaggagga ttaaggcata taataacagc    900
gccgaaatca aaacc                                                    915
```

The β-carotene hydroxylase protein from daffodil has an amino acid sequence of SEQ ID NO: 16 as follows:

```
Met Ala Val Trp Ile Ser Ala Ala Pro Pro Ala Leu Ala Ile Ser Ser
 1               5                  10                  15

Ala Pro Arg Ile Arg Arg Val Ile Leu Phe Ser Pro Leu His Ser Arg
             20                  25                  30

Gln Ile Gly Trp Pro Pro Ile Arg Asn Arg Arg Lys Arg Ser Lys Ser
             35                  40                  45

Thr Val Phe Phe Ala Ser Asp Val Asp Val Gly Lys Ser Asn Gly Gly
         50                  55                  60

Asp Gly Ile Val Asp Lys Ile Glu Arg Leu Lys Lys Gln Glu Gln Leu
 65                  70                  75                  80

Met Ile Ser Lys Ser Arg Thr Thr Glu Arg Met Glu Arg Lys Arg Ser
                 85                  90                  95

Glu Arg Thr Thr Tyr Leu Ile Ala Ala Met Met Ser Ser Leu Gly Ile
                100                 105                 110

Thr Ser Met Ala Ile Val Ser Val Tyr Tyr Arg Phe Ala Trp Gln Met
             115                 120                 125

Glu Glu Gly Glu Ile Pro Val Thr Glu Met Leu Gly Thr Phe Ala Leu
130                 135                 140

Ser Val Gly Ala Ala Val Gly Met Glu Phe Trp Ala Arg Trp Ala His
145                 150                 155                 160

Arg Ala Leu Trp His Ala Ser Leu Trp His Met His Glu Ser His His
                 165                 170                 175

Lys Pro Arg Asp Gly Pro Phe Glu Leu Asn Asp Val Phe Ala Val Ile
             180                 185                 190

Asn Ala Val Pro Ala Ile Ser Leu Leu Tyr Tyr Gly Phe Phe Asn Arg
             195                 200                 205

Gly Leu Val Pro Gly Leu Cys Phe Gly Ala Gly Leu Gly Ile Thr Leu
         210                 215                 220

Tyr Gly Met Ala Tyr Met Phe Val His Asp Gly Leu Val His Arg Arg
225                 230                 235                 240

Phe Pro Val Gly Pro Ile Ala Asp Val Pro Tyr Phe Arg Arg Val Ala
                 245                 250                 255

Ala Ala His Arg Ile His His Thr Glu Lys Phe Asn Gly Val Pro Tyr
             260                 265                 270

Gly Leu Phe Leu Gly Pro Lys Glu Leu Glu Val Gly Gly Glu Glu
         275                 280                 285

Glu Leu Glu Lys Leu Ile Lys Arg Arg Ile Glu Ile Asn Ser Arg Ser
290                 295                 300

Leu Asp Val Lys
305
```

This protein is encoded by a nucleic acid molecule having a nucleotide sequence of SEQ ID NO: 17 as follows:

```
ATGGCAGTTT GGATCTCCGC CGCTCCCCCG GCCCTCGCGA TCTCCTCCGC CCCCCGCATC    60

CGCCGTGTCA TCCTCTTCTC CCCGCTCCAC AGCCGTCAGA TCGGATGGCC GCCGATCAGG   120

AACCGTCGAA AGAGGAGCAA GTCGACGGTG TTTTTCGCCT CGGACGTGGA CGTCGGTAAG   180

TCCAACGGCG GCGATGGGAT CGTCGATAAA ATTGAGCGAC TGAAGAAACA GGAGCAGCTG   240

ATGATCTCGA AATCGCGCAC GACGGAGAGA ATGGAGAGGA AGCGATCGGA GAGGACGACG   300
```

```
TATCTGATCG CGGCGATGAT GTCGAGCTTG GGGATCACGT CAATGGCGAT CGTCTCCGTT    360

TATTACCGAT TTGCTTGGCA AATGGAGGAA GGGGAGATTC CCGTAACGGA AATGCTGGGA    420

ACGTTCGCGT TGTCAGTGGG GGCCGCAGTT GGGATGGAAT TTTGGGCGAG ATGGGCGCAT    480

CGAGCTCTAT GGCATGCATC CTTGTGGCAC ATGCATGAGT CGCATCACAA ACCACGTGAC    540

GGTCCATTTG AGCTCAACGA TGTTTTCGCC GTCATTAACG CCGTTCCGGC GATCTCTCTT    600

CTATACTACG GCTTCTTCAA CCGCGGACTA GTTCCCGGCC TCTGCTTTGG TGCCGGTCTT    660

GGAATCACAC TCTACGGGAT GGCGTACATG TTCGTTCACG ACGGATTGGT TCACCGGCGA    720

TTCCCAGTGG GACCCATTGC CGATGTTCCC TATTTCAGAA GAGTTGCCGC TGCTCATCGG    780

ATCCACCATA CTGAGAAGTT CAACGGGGTG CCCTATGGGC TGTTCTTGGG TCCCAAGGAA    840

TTGGAGGAGG TGGGCGGTGA AGAGGAGCTG GAGAAATTGA TTAAGAGGAG GATTGAGATT    900

AACAGCCGCA GCTTAGATGT TAA                                           923
```

The β-carotene hydroxylase from grape has an amino acid sequence of SEQ ID NO: 18 as follows:

```
Met Ala Thr Gly Ile Ser Ala Ser Leu Asn Ser Met Ser Cys Arg Leu
 1               5                  10                  15

Gly Arg Asn Ser Phe Thr Ala Thr Gly Pro Ser Ser Val Ile Ser Leu
            20                  25                  30

Ser Ser Phe Leu Thr Pro Val Thr His Leu Lys Gly Asn Ile Phe Pro
        35                  40                  45

Leu Gln Arg Arg Arg Ser Leu Lys Val Cys Leu Val Leu Glu Lys Glu
    50                  55                  60

Ile Glu Asp Gly Ile Glu Ile Glu Asp Asp Ser Pro Glu Ser Ser Asn
65                  70                  75                  80

Arg Ala Ser Glu Arg Leu Ala Arg Lys Lys Ala Glu Arg Tyr Thr Tyr
                85                  90                  95

Leu Val Ala Ala Met Met Ser Ser Leu Gly Ile Thr Ser Met Ala Ile
            100                 105                 110

Val Ala Val Tyr Tyr Arg Leu Ser Trp Gln Met Glu Gly Gly Glu Ile
        115                 120                 125

Pro Val Leu Glu Met Leu Gly Thr Phe Ala Leu Ser Val Gly Ala Ala
    130                 135                 140

Val Gly Met Glu Phe Trp Ala Arg Trp Ala His Lys Ala Leu Trp His
145                 150                 155                 160

Ala Ser Leu Trp His Met His Glu Ser His His Arg Pro Arg Glu Gly
                165                 170                 175

Pro Phe Glu Leu Asn Asp Val Phe Ala Ile Ile Asn Ala Val Pro Ala
            180                 185                 190

Ile Ser Leu Leu Ser Tyr Gly Leu Phe Asn Lys Gly Leu Val Pro Gly
        195                 200                 205

Leu Cys Phe Gly Ala Gly Leu Gly Ile Thr Val Phe Gly Met Ala Tyr
    210                 215                 220

Met Phe Val His Asp Gly Leu Val His Arg Arg Phe Pro Val Gly Pro
225                 230                 235                 240

Ile Ala Asn Val Pro Tyr Leu Arg Lys Val Ala Ser Ala His Gln Leu
                245                 250                 255
```

-continued

```
His His Ser Asp Lys Phe Asn Gly Val Pro Tyr Gly Leu Phe Leu Gly
            260                 265                 270

Pro Met Glu Leu Glu Glu Val Gly Gly Met Glu Glu Leu Glu Lys Glu
            275                 280                 285

Ile Ser Arg Arg Ile Lys Ser Ser Asp Ser Ser
    290                 295
```

This protein is encoded by a nucleotide sequence of SEQ ID NO: 19 as follows:

```
atggcgacag gaatttcggc ttctttaaac tccatgtcgt gccgtttggg ccggaatagt   60
ttcacagcca ccggacccag ctcggtgata agtttgtcgt ctttcttaac tccggtgacc  120
cacttgaagg ggaatatttt tcctctacag agaaggagga gcttgaaggt gtgcttggtc  180
ctggagaaga aaattgaaga tggtattgaa attgaggacg acagtccgga aagctcgaac  240
agggcctcgg agagactagc gaggaagaaa gcggaaagat acacttatct tgttgctgct  300
atgatgtcta gcctcggcat cacttcaatg gctatcgttg ctgtctacta cagatttct   360
tggcaaatgg agggtggaga atcccagtt ctggaaatgt tgggtacatt tgctctttct  420
gtgggagctg ctgtggggat ggagttttgg gctcggtggg ctcacaaagc gctctggcat  480
gcttcactgt ggcatatgca cgagtctcac catagacoca gagaaggtcc tttcgagctc  540
aacgatgtgt ttgccatcat caatgccgtc ccggcaatat ctctgctctc ctatggcctc  600
ttcaacaaag gcctcgtccc aggtctctgt ttcggagctg gactaggaat aacagtgttt  660
ggcatggcct acatgtttgt ccacgacggc cttgtccacc gtcgattccc tgtaggaccc  720
atcgccaacg tcccttatct acgaaaagta gcttcggccc accaacttca tcactctgac  780
aaatttaatg gagttccata cgggctgttc ttgggaccca tggagctgga agaggtggga  840
ggcatggaag agttggaaaa ggagatcaat agaagaatta aatcatctga ctcttca     897
```

The β-carotene hydroxylase from maize has an amino acid sequence of SEQ ID NO: 20 as follows:

```
Met Glu Gly Gly Gly Glu Ile Pro Val Thr Glu Met Val Gly Thr Phe
  1               5                  10                  15

Ala Leu Ser Val Gly Ala Ala Val Gly Met Glu Phe Trp Ala Arg Trp
            20                  25                  30

Ala His Arg Ala Leu Trp His Ala Ser Leu Trp His Met His Gln Ser
        35                  40                  45

His His Arg Pro Arg Asp Gly Pro Phe Glu Leu Asn Asp Val Phe Ala
    50                  55                  60

Ile Val Asn Ala Val Pro Ala Met Ser Leu Leu Ala Tyr Gly Phe Phe
 65                  70                  75                  80

Asn Arg Gly Leu Val Pro Gly Leu Cys Phe Gly Ala Gly Leu Gly Ile
                85                  90                  95

Thr Leu Phe Gly Met Ala Tyr Met Phe Val His Asp Gly Leu Val His
            100                 105                 110

Arg Arg Phe Pro Val Gly Pro Ile Glu Asn Val Pro Tyr Phe Arg Arg
        115                 120                 125

Val Ala Ala Ala His Gln Ile His His Met Asp Lys Phe Gln Gly Val
    130                 135                 140
```

```
Pro Tyr Gly Leu Phe Leu Gly Pro Lys Glu Leu Lys Glu Val Gly Gly
145                 150                 155                 160

Thr Glu Glu Leu Glu Lys Glu Ile Lys Lys Arg Ile Arg Arg Arg Glu
                165                 170                 175

Ala Leu Asp Ala Ile Gln
            180
```

The protein is encoded by a nucleic acid having the nucleotide sequence of SEQ ID NO: 21 as follows:

```
atggagggg gcggcgagat cccggtgacg gagatggtcg gcaccttcgc gctctcggtg    60
ggcgccgcgg tggggatgga gttctgggcg cggtgggcgc accgggcgct gtggcacgcg  120
tcgctgtggc acatgcacca gtcccaccac cggccccgcg acgggcccct cgagctcaac  180
gacgtcttcg ccatcgtcaa cgccgtcccg gccatgtccc tcctcgccta cggcttcttc  240
aaccggggcc tagtgccggg cctctgcttc ggcgcgggc tggggatcac gctgttcggg  300
atggcctaca tgttcgtgca cgacggcctc gtccaccgcc gcttcccgt cgggcccatc  360 gagaacgtgc cctacttccg ccgcgtcgcc gccgcccatc agatacatca catggacaag  420
ttccagggcg tgccctacgg cctgttcctg gggcccaagg agctgaagga ggtggagga  480 actgaggagc tggagaagga gatcaagaag aggatcagga ggagggaggc cctagacgcc  540
atccaata                                                           548
```

The β-carotene hydroxylase protein from marigold has an amino acid sequence for SEQ ID NO: 22 as follows:

```
Met Ala Ala Ala Ile Ala Val Pro Cys Ser Ser Arg Pro Phe Gly Leu
  1               5                  10                  15

Gly Arg Met Arg Leu Leu Gly His Lys Pro Thr Thr Ile Thr Cys His
                20                  25                  30

Phe Pro Phe Ser Phe Ser Ile Lys Ser Phe Thr Pro Ile Val Arg Gly
            35                  40                  45

Arg Arg Cys Thr Val Cys Phe Val Ala Gly Gly Asp Ser Asn Ser Asn
        50                  55                  60

Ser Asn Asn Ser Asp Ser Asn Ser Asn Asn Pro Gly Leu Asp Leu
 65                 70                  75                  80

Asn Pro Ala Val Met Asn Arg Asn Arg Leu Val Glu Glu Lys Met Glu
                85                  90                  95

Arg Lys Lys Ser Glu Arg Phe Thr Tyr Leu Val Ala Ala Ile Met Ser
            100                 105                 110

Thr Phe Gly Ile Thr Ser Met Ala Val Met Ala Val Tyr Tyr Arg Phe
        115                 120                 125

Ser Trp Gln Met Glu Gly Gly Glu Ile Pro Tyr Val Glu Met Phe Gly
    130                 135                 140

Thr Phe Ala Leu Ser Val Gly Ala Ala Val Gly Met Glu Tyr Trp Ala
145                 150                 155                 160

Arg Trp Ala His Glu Ala Leu Trp His Ala Ser Leu Trp His Met His
                165                 170                 175

Glu Ser His His Lys Pro Arg Glu Gly Pro Phe Glu Leu Asn Asp Val
            180                 185                 190

Phe Ala Ile Thr Asn Ala Val Pro Ala Ile Ala Leu Leu Ser Tyr Gly
        195                 200                 205
```

-continued

```
Phe Phe His Lys Gly Ile Ile Pro Gly Leu Cys Phe Gly Ala Gly Leu
    210             215                 220
Gly Ile Thr Val Phe Gly Met Ala Tyr Met Phe Val His Asp Gly Leu
225             230                 235                 240
Val His Arg Arg Phe Gln Val Gly Pro Ile Ala Asn Val Pro Tyr Leu
                245                 250                 255
Arg Arg Val Ala Ala Ala His Gln Leu His His Thr Glu Lys Phe Asn
            260                 265                 270
Gly Val Pro Tyr Gly Leu Phe Leu Gly Pro Lys Glu Leu Glu Glu Val
        275                 280                 285
Gly Gly Thr Glu Glu Leu Asp Lys Glu Ile Gln Arg Arg Ile Lys Leu
    290             295                 300
Tyr Asn Asn Thr Lys
305
```

This protein is encoded by a nucleic acid molecule having a nucleotide sequence of SEQ ID NO: 23 as follows:

```
atggcggcag caattgctgt cccttgtagc tcaagaccat ttggcttagg tcgaatgcgg   60
ttacttggtc ataaacccac aaccataact tgtcacttcc cctttcttt ttctatcaaa   120
tcatttaccc caattgttag gggcagaaga tgtactgttt gttttgttgc cggtggcgac   180
agtaatagta acagtaataa taatagtgac agtaatagta ataatccggg tctggattta   240
aacccggcgg ttatgaaccg taaccgtttg gttgaagaaa aaatggagag gaaaaaatcg   300
gaacgattta cttatcttgt tgcagctatt atgtctactt ttggaattac ttcaatggcg   360
gttatggcgg tttattaccg gttttcatgg caaatggagg gtggagaaat tccttatgtg   420
gagatgtttg gtacatttgc tctctccgtt ggtgctgcgg taggaatgga gtattgggca   480
agatgggctc atgaggcact atggcatgct tctttgtggc acatgcatga gtcacaccat   540
aagccacgag aaggtccgtt tgagcttaat gatgtgtttg ctataacaaa tgcggtcccg   600
gccattgcgt tgcttagtta tgggttttc cacaaaggca taattccggg tctttgtttt   660
ggggcgggac tgggaattac ggtgtttgga atggcgtata tgttcgtcca cgacgggcta   720
gttcacagaa gattccaagt gggtccgatt gcgaatgttc cctatcttcg aagggttgca   780
gcggctcatc agctgcatca cacggaaaaa tttaatggtg ttccttatgg cttgttcttg   840
ggacctaagg agctagaaga agtgggtggt acggaagaat tggacaagga gattcaaaga   900
agaattaaat tgtataataa tactaaa                                       927
```

See Moehs C P et al., "Analysis of Carotenoid Biosynthetic Gene Expression During Marigold Petal Development," Plant Mol. Biol. 45:281-293 (2001), which is hereby incorporated by reference in its entirety.

The β-carotene hydroxylase protein from *Medicago truncatula* has an amino acid sequence of SEQ ID NO: 24 as follows:

```
Met Gly Ser Gln Ala Leu Trp His Ala Ser Leu Trp His Met His Glu
1               5                   10                  15
Ser His His Arg Ala Arg Glu Gly Ala Phe Glu Leu Asn Asp Val Phe
                20                  25                  30
Ala Ile Ile Asn Ala Val Pro Ala Ile Ala Leu Leu Asn Phe Gly Phe
                35                  40                  45
Phe His Lys Gly Leu Val Pro Gly Leu Cys Phe Gly Ala Gly Leu Gly
            50                  55                  60
```

```
Ile Thr Val Phe Gly Met Ala Tyr Met Phe Val His Asp Gly Leu Val
 65                  70                  75                  80

His Arg Arg Phe Ser Val Gly Pro Ile Ala Asn Val Pro Tyr Phe Arg
                 85                  90                  95

Arg Val Ala Ala Ala His Lys Leu His His Ser Asp Lys Phe Glu Gly
            100                 105                 110

Val Pro Tyr Gly Leu Phe Leu Gly Pro Lys Glu Leu Glu Glu Val Gly
        115                 120                 125

Gly Leu Glu Glu Leu Glu Lys Glu Ile Ser Arg Arg Thr Lys Ser Tyr
130                 135                 140

Asn Ser Ser Ser
145
```

This protein is encoded by a nucleic acid molecule having a nucleotide sequence of SEQ ID NO: 25 as follows:

```
atggagtttt gggctagatg ggctcacagg ctctttggca tgcttccttg tggcacatgc      60
atgagtccca tcatagagca agagaaggag ctttcgagtt gaatgatgtt tttgcaataa     120
tcaatgctgt tcctgctatc gctctcctta actttggttt ctttcacaaa ggattggtcc     180
ctggtctttg ctttggtgcg ggtcttggaa ttacggtatt tgggatggcc tacatgtttg     240
tacatgatgg tttggttcat aggagattct cagtgggacc cattgccaat gtgccctatt     300
tcagaagggt agctgcagcc cacaaacttc accattcaga caaattcgaa ggggtgccat     360
atgggctgtt tttgggacca aaggaacttg aggaagtggg agggctagaa gagctagaga     400
aagagataag taggaggaca aaatcataca atagtagttc a                         461
```

The β-carotene hydroxylase protein from onion has an amino acid sequence of SEQ ID NO: 26 as follows:

```
Met Ala Val Gly Ile Ser Ala Arg Pro Arg Pro Thr Leu Asn Leu Val
  1               5                  10                  15

Ala Asp Thr Phe Ser Arg Pro Pro Phe Pro Arg Arg Cys Leu Phe Pro
             20                  25                  30

Ser Phe Pro Pro Ser Thr Asn Arg Phe Leu Ser Ser Pro Pro Leu Arg
         35                  40                  45

Ser Arg Gln Lys Arg Ser Ser Arg Thr Val Tyr Leu Val Leu His Glu
         50                  55                  60

Gly Asp Lys Ser Thr Ala Asp Asn Glu Val Glu Ile Glu Lys Asn Leu
 65                  70                  75                  80

Glu Glu Ser Arg Val Ser Lys Gln Arg Ala Met Glu Arg Thr Glu Arg
                 85                  90                  95

Lys Lys Thr Glu Arg Thr Thr Tyr Leu Val Ala Ala Ile Met Ser Ser
            100                 105                 110

Phe Gly Ile Thr Ser Met Ala Ile Val Ser Val Tyr Tyr Arg Phe Ala
        115                 120                 125

Trp Gln Phe Glu Gly Gly Glu Ile Pro Leu Thr Glu Met Phe Gly Thr
130                 135                 140

Phe Ala Leu Ser Val Gly Ala Ala Val Gly Met Glu Phe Trp Ala Asp
145                 150                 155                 160

Gly Pro Thr Glu Pro Tyr Gly Thr Pro His Tyr Gly Thr Cys Thr Asn
                165                 170                 175

Leu Ile Thr Ser Gln Glu Glu Gly Pro Phe
            180                 185
```

This protein is encoded by a nucleic acid molecule having a nucleotide sequence of SEQ ID NO: 27:

```
atggcggtcg gaatctccgc cagaccccga ccaaccctca acctcgtcgc tgacaccttc    60
tcccgaccgc cattccccccg acgctgctta ttcccatcct ttcctccatc gacgaaccgt   120
ttcttatcct cacctccgct tagatcgagg caaaaacgaa gcagcagaac cgtgtatctc   180
gtcctccacg agggagataa gtctaccgcc gacaacgaag tcgaaatcga agaatcta    240
gaggagagta gggtttctaa caacgtgca atggagagaa ccgaaaggaa gaaaacggaa   300
cggaccactt atttggttgc ggcgattatg tccagcttcg gaattacttc tatggcgatt   360
gtttccgtct attatcgatt cgcttggcaa ttcgagggag gagagattcc attaaccgaa   420
atgtttggga catttgcatt atcagttggc gccgctgtag gaatggagtt ttgggcagat   480
gggcccacag agccctatgg cacgccacat tatggcacat gcacgaatct catcaccagc   540
caagaagaag gtc cttttttg                                              560
```

The β-carotene hydroxylase protein from pepper has an amino acid sequence of SEQ ID NO: 28 as follows:

```
Met Ala Ala Glu Ile Ser Ile Ser Ala Ser Ser Arg Ala Ile Cys Leu
 1               5                  10                  15

Gln Arg Asn Pro Phe Pro Ala Pro Lys Tyr Phe Ala Thr Ala Pro Pro
            20                  25                  30

Leu Leu Phe Phe Ser Pro Leu Thr Cys Asn Leu Asp Ala Ile Leu Arg
        35                  40                  45

Ser Arg Arg Lys Pro Arg Leu Ala Ala Cys Phe Val Leu Lys Asp Asp
    50                  55                  60

Lys Leu Tyr Thr Ala Gln Ser Gly Lys Gln Ser Asp Thr Glu Ala Ile
65                  70                  75                  80

Gly Asp Glu Ile Glu Val Glu Thr Asn Glu Glu Lys Ser Leu Ala Val
                85                  90                  95

Arg Leu Ala Glu Lys Phe Ala Arg Lys Lys Ser Glu Arg Phe Thr Tyr
            100                 105                 110

Leu Val Ala Ala Val Met Ser Ser Leu Gly Ile Thr Ser Met Ala Val
        115                 120                 125

Ile Ser Val Tyr Tyr Arg Phe Ser Trp Gln Met Glu Gly Gly Glu Met
    130                 135                 140

Pro Phe Ser Glu Met Phe Cys Thr Phe Ala Leu Ala Phe Gly Ala Ala
145                 150                 155                 160

Ile Gly Met Glu Tyr Trp Ala Arg Trp Ala His Arg Ala Leu Trp His
                165                 170                 175

Ala Ser Leu Trp His Met His Glu Ser His His Arg Pro Arg Glu Gly
            180                 185                 190

Pro Phe Glu Leu Asn Asp Ile Phe Ala Ile Ile Asn Ala Val Pro Ala
        195                 200                 205

Ile Ala Phe Phe Ser Phe Gly Phe Asn His Lys Gly Leu Ile Pro Gly
    210                 215                 220

Ile Cys Phe Gly Ala Gly Leu Gly Ile Thr Val Phe Gly Met Ala Tyr
225                 230                 235                 240

Met Phe Val His Asp Gly Leu Val His Lys Arg Phe Pro Val Gly Pro
                245                 250                 255

Ile Ala Lys Val Pro Tyr Phe Gln Arg Val Ala Ala His Gln Leu
            260                 265                 270
```

```
His His Ser Asp Lys Phe Asp Gly Val Pro Tyr Gly Leu Phe Leu Gly
        275                 280                 285

Pro Lys Glu Leu Glu Glu Val Gly Val Ile Glu Glu Leu Glu Lys Glu
        290                 295                 300

Val Asn Arg Arg Ile Lys Ser Leu Lys Arg Leu
305                 310                 315
```

See Bouvier et al., "Xanthophyll Biosynthesis: Molecular and Functional Characterization of Carotenoid Hydroxylases from Pepper Fruits (*Capsicum annuum* L.)," *Biochim. Biophys. Acta* 1391(3):320-328 (1998), which is hereby incorporated by reference in its entirety. This protein is encoded by a nucleic acid having a nucleotide sequence of SEQ ID NO: 29 as follows:

```
ATGGCTGCTG AAATTTCAAT CTCCGCTAGC TCCCGTGCCA TTTGTCTCCA GCGCAACCCC   60
TTTCCTGCTC CAAAATACTT TGCAACTGCC CCGCCACTTC TCTTCTTCTC TCCTTTAACT  120
TGTAATCTCG ACGCAATTTT GCGGTCTCGG AGAAAGCCTA GGTTGGCTGC TTGCTTTGTG  180
CTGAAGGATG ACAAATTGTA TACTGCACAA AGTGGAAAAC AAAGCGATAC TGAAGCAATA  240
GGTGATGAGA TTGAAGTAGA GACTAATGAG GAGAAGAGTT TAGCTGTCAG GCTGGCCGAA  300
AAATTTGCGA GGAAGAAGTC AGAGAGGTTT ACTTATCTTG TAGCTGCGGT AATGTCCAGT  360
TTGGGGATTA CTTCTATGGC GGTTATTTCA GTTTATTACA GATTTTCGTG GCAAATGGAA  420
GGTGGAGAAA TGCCTTTTTC TGAAATGTTT TGTACATTCG CTCTCGCCTT TGGCGCTGCC  480
ATAGGAATGG AGTACTGGGC GAGATGGGCG CATAGAGCAC TATGGCATGC TTCTTTGTGG  540
CATATGCACG AGTCACACCA TAGACCAAGG GAAGGACCTT TCGAGCTGAA CGATATTTTT  600
GCCATAATCA ATGCTGTTCC AGCTATAGCT TTTTTTTCAT TCGGTTTCAA CCATAAAGGC  660
CTTATCCCTG GAATATGTTT TGGCGCTGGA TTAGGGATTA CAGTATTTGG GATGGCCTAC  720
ATGTTTGTTC ACGATGGATT AGTTCACAAG AGATTCCCCG TGGGACCCAT TGCCAAAGTA  780
CCTTATTTTC AGAGAGTAGC TGCAGCACAT CAGCTTCATC ACTCGGACAA ATTTGATGGG  840
GTCCCATATG GCTTGTTCCT AGGACCTAAG GAATTGGAAG AAGTAGGGGT TTGGAAAAGG  900
AAGTTAACCG AAGAATTAAA AGTTTGAAGA GATTA                              945
```

The β-carotene hydroxylase protein from pine has an amino acid sequence of SEQ ID NO: 30 as follows:

```
Met Gly Leu Arg Ser Val Ser Ser Pro Tyr Gly Leu Ser Lys Cys Asp
 1                   5                  10                  15

Ser Ile Leu Ser Pro Pro Leu Ser Ser Thr Lys Pro Ala Ala Ala Pro
            20                  25                  30

Leu Gly Arg Ala Val Tyr Cys Tyr Tyr Leu Ala Leu Ala Arg Ala Ser
            35                  40                  45

Ser Val Asn Arg Asn Gly Phe Arg Ser Ala Arg Val Phe Ser Glu Phe
        50                  55                  60

Arg Gly Arg Arg Lys Val Leu Ser Leu Val Phe Ala Ser Thr Lys Lys
65                  70                  75                  80

Ser Gln Gln Leu Glu Met Lys Ser Glu Ser Ile Glu Asp Ala Ser
                    85                  90                  95

Ala Thr Glu Phe Ala Asp Ser Leu Ser Ser Arg Val Asp Glu Ile Ala
                100                 105                 110

Asn Lys Arg Glu Arg Asp Lys Arg Ala Ala Thr Arg Lys Ser Glu Arg
            115                 120                 125
```

```
His Ala Tyr Phe Phe Ala Ala Val Ala Ser Ser Val Gly Ile Thr Ser
            130                 135                 140
Met Thr Ala Ala Ala Val Tyr Tyr Arg Phe Val Trp Gln Met Gln Gly
145                 150                 155                 160
Ala Gln Ile Pro Tyr Met Glu Ile Phe Gly Thr Phe Ala Leu Ala Val
                165                 170                 175
Gly Ala Thr Val Gly Met Glu Phe Trp Ala Arg Trp Ala His Arg Ala
                180                 185                 190
Leu Trp His Ala Ser Leu Trp His Met His Glu Ser His His Arg Pro
            195                 200                 205
Arg Glu Gly Pro Phe Glu Leu Asn Asp Val Phe Ala Ile Ile Asn Ala
            210                 215                 220
Phe Pro Ala Ile Ala Leu Met Ala Tyr Gly Phe Phe Asn Lys Gly Phe
225                 230                 235                 240
Val Pro Gly Leu Cys Phe Gly Ala Gly Leu Gly Ile Thr Val Phe Gly
                245                 250                 255
Met Ala Tyr Met Phe Val His Asp Gly Leu Val His Arg Arg Phe Pro
                260                 265                 270
Val Gly Pro Ile Ala Asp Val Pro Tyr Leu Leu Lys Val Ala Ala Ala
            275                 280                 285
His Gln Leu His His Ala Asp Lys Phe Asn Gly Val Pro Tyr Gly Leu
            290                 295                 300
Phe Leu Gly Pro Lys Glu Leu Glu Glu Val Gly Gly His Asp Glu Leu
305                 310                 315                 320
Glu Lys Leu Phe Asn Ser Lys Met Lys Gly Leu Gln Lys His
                325                 330
```

This protein is encoded by a nucleic acid having the nucleotide sequence of SEQ ID NO: 31 as follows:

```
atggggctga ggagtgtttc atctccatac ggattgtcaa agtgcgattc gatcctctca    60
cctccgcttt catcaaccaa accagctgca gcaccactgg gcagggcggt ttattgttat   120
tatctcgcgc ttgccagagc ttcttcagtt aacagaaatg ggttccgttc tgcccgcgtt   180
ttttctgaat ttcgtgggag aaggaaggtg ctgtctctag tctttgcgtc gactaaaaaa   240
tcccaacagc tagagatgaa atcagaatcc attgaagatg atgcttctgc tactgaattt   300
gcagactcat taagcagtag agttgatgag attgcgaata aaagggaacg ggataaaaga   360
gctgcgacga ggaagtccga acgccatgcc tacttctttg ctgccgttgc ctccagtgtt   420
ggtattacta gtatgactgc cgctgctgtt tactaccgat tgtttggca gatgcagggt   480
gcacagattc cctacatgga gatctttgga acttttgcat tagcagtggg agccacggtt   540
ggaatggaat ttgggcacg ttgggctcac cgagctctat ggcacgcctc cttgtggcac   600
atgcatgagt ctcatcaccg gccaagggag ggacctttg agttgaatga tgtgttcgca   660
atcatcaatg cttttcctgc cattgcacta atggcttatg gattctttaa caaaggcttt   720
gtgccaggtc tttgctttgg tgctgggctt ggtatcaccg ttttggggat ggcatatatg   780
tttgtccatg atgggcttgt tcatcgccgc tttcctgttg gacctattgc tgatgttcca   840
tatcttctta aagtagctgc tgcacatcag cttcatcatg cagataagtt taatggtgtg   900
ccttatggtc ttttccttgg accaaaagaa ctggaagagg ttgggggcca tgacgagcta   960
gaaaaattgt ttaatagtaa gatgaagggc ctccaaaagc acta                  1004
```

The β-carotene hydroxylase protein from rice has an amino acid sequence of SEQ ID NO: 32 as follows:

```
Met Ala Val Ala Arg Leu Val Val Ile Thr Pro Ala Val Leu Leu Gly
 1               5                  10                  15

Arg Thr Ala Arg Val Ser Pro Ser Ala Val Pro Arg Leu Arg Pro Ile
                20                  25                  30

Val Ala Gly Arg Arg Ala Val Ala Ala Pro Thr Arg Ala Val Leu Gly
            35                  40                  45

Asp Gly Ala Gly Val Gly Gly Glu Glu Asp Ala Val Val Ala Val Val
        50                  55                  60

Glu Glu Asp Ala Val Ala Arg Arg Ala Ala Arg Lys Arg Ser Glu Arg
 65                  70                  75                  80

Arg Thr Tyr Leu Val Ala Ala Val Met Ser Ser Leu Gly Phe Thr Ser
                85                  90                  95

Met Ala Ala Ala Ala Val Tyr Tyr Arg Phe Ala Trp Gln Met Glu Ala
                100                 105                 110

Gly Gly Gly Asp Val Pro Ala Thr Glu Met Val Gly Thr Phe Ala Leu
            115                 120                 125

Ser Val Gly Ala Ala Val Gly Met Glu Phe Trp Ala Arg Trp Ala His
        130                 135                 140

Arg Ala Leu Trp His Ala Ser Leu Trp His Met His Glu Ser His His
145                 150                 155                 160

Arg Pro Arg Asp Gly Pro Phe Glu Leu Asn Asp Val Phe Ala Ile Ala
                165                 170                 175

Asn Ala Ala Pro Ala Ile Ser Leu Leu Ala Tyr Gly Leu Leu Asn Arg
                180                 185                 190

Gly Leu Leu Pro Gly Leu Cys Phe Gly Ala Gly Leu Gly Ile Thr Leu
            195                 200                 205

Phe Gly Met Ala Tyr Met Phe Val His Asp Gly Leu Val His Arg Arg
            210                 215                 220

Phe Pro Val Gly Pro Ile Glu Asn Val Pro Tyr Phe Arg Arg Val Ala
225                 230                 235                 240

Ala Ala His Gln Ile His His Thr Asp Lys Phe Glu Gly Val Pro Tyr
                245                 250                 255

Gly Leu Phe Leu Gly Pro Lys Glu Leu Glu Glu Val Gly Gly Thr Glu
                260                 265                 270

Glu Leu Asp Lys Glu Ile Lys Lys Arg Ile Lys Arg Lys Glu Ala Met
                275                 280                 285

Asp Ala Ile Arg
    290
```

This protein is encoded by a nucleic acid having the nucleotide sequence of SEQ ID NO: 33 as follows:

```
atggccgtcg cgaggctggt ggtcatcacc ccgccgtcc tcctcggccg caccgcccgc   60
gtctcgccgt cggcggtgcc gcggctgcgg cccatcgtcg ccggccgccg cgccgtggcg  120
gcgcccacac gcgccgtcct gggagacggg gcgggtgtcg gcggcgagga ggatgcggtg  180
gtggcggtgg tggaggagga cgcggtcgcc cggcgcgcgg cgaggaagcg gtcggagcgg  240
cgcacgtacc tggtggcggc ggtgatgtcc agcctcgggt tcacgtccat ggccgccgcc  300
gccgtctact accgcttcgc ctggcaaatg gaggccggcg gcggcgacgt tccggcgacg  360
gagatggtcg gcacgttcgc gttgtcggtg ggggcggcgg tggggatgga gttctgggcg  420
cggtgggcgc accgggcgct gtggcacgcg tcgctgtggc acatgcacga gtcgcaccac  480
```

-continued

```
cgcccgcgcg acggcccgtt cgagctcaac gacgtcttcg ccatcgccaa cgccgccccg   540
gccatctccc tcctcgccta cggcctcctc aaccgcggcc tcctccccgg cctctgcttc   600
ggcgcggggc ttgggattac gctgttcggg atggcgtaca tgttcgtcca cgacggcctg   660
gtccaccggc gcttccccgt ggggcccatc gagaacgtgc cctacttccg ccgagttgct   720
gccgcccacc agatacatca cacggacaag ttcgaaggcg tgccctacgg cctgttcctc   780
ggacccaagg agttggagga ggtgggtggg actgaggagc tggacaagga gatcaagaag   840
aggatcaaga ggaaggaggc catggacgcc atcaga                              876
```

The β-carotene hydroxylase protein from sorghum has an amino acid sequence of SEQ ID NO: 34 as follows:

```
Thr Pro Gly Ser Arg Ser Pro Gly Ser Leu Ser Cys Pro Ser Ile Ala
  1               5                  10                  15

Phe His Trp Lys Val Gln Ala Arg Ala His Gly Arg Arg Ser Val Arg
                 20                  25                  30

Arg Arg Asp Asp Arg Val Arg Arg Gln Glu Pro Ala Ala Arg Gly Arg
             35                  40                  45

Gly Arg Gly Ala Pro Gln Gly Ala Ser Thr Cys Arg Ala Arg Pro Ala
 50                  55                  60

Val Leu Ala Ala His His His Gln Gly Arg Ala Pro Pro Arg Ala Arg
 65                  70                  75                  80

Asp Arg His Val Leu Arg Ala Ala Arg His Gly Ala Pro Gly Gly Pro
                 85                  90                  95

Gly Pro Gly Cys Ser Gly Ala Gly Ala Gly Ala Gly Asp Gly Ala Gly
                100                 105                 110

Arg Gly Gly Gln Gly Arg Gly Gly Ala Ala His Arg Gly Glu Glu Gly
             115                 120                 125

Ala Glu Ala Val Arg Ala Ser Asp Val Pro Gly Gly Arg His Asp Val
    130                 135                 140

Gln Pro Arg Val His Val His Gly Arg Arg Arg Val Leu Ser Leu
145                 150                 155                 160

Gln Leu Ala Asn Gly Gly Arg Arg Gly Ala Gly Glu Arg Asp Val Gly
                165                 170                 175

His Val Arg Ala Leu Arg Arg Arg Gly Gly Arg Asp Gly Val Leu Gly
                180                 185                 190

Ala Val Gly Ala Pro Gly Ala Val Ala Arg Leu Pro Val Ala His Ala
            195                 200                 205

Arg Val Ala Pro Pro Ala Ala Gly Gly Pro Leu Arg Ala Gln Arg Arg
        210                 215                 220

Val Arg His His Gln Arg Arg Ala Gly His Leu Ser Pro Arg Leu
225                 230                 235
```

This protein is encoded by a nucleic acid having the nucleotide sequence of SEQ ID NO: 35 as follows:

```
actcccggct cccgctcgcc cgggtccctg tcctgtccat ctatagcgtt ccattggaaa    60
gtgcaagcac gggcccatgg ccgccggtct gtccggcgcc gcgatgaccg ggttcgtcgc   120
caagaacccg ctgctcgcgg ccgcggccgc ggcgcgccgc agggcgcatc cacttgccgg   180
gcgcgccctg ccgttctcgc cgctcaccac caccagggcc gcgcgccgcc gcgggctcgg   240
gaccgtcacg tgcttcgtgc cgccagacac ggagcacccg gcggcccggg ccccggctgc   300
```

-continued
```
tccggtgccg gtgccggtgc cggagacggc gctggacgag gaggccaggg ccgcggcggc  360
gcggcgcatc gcggagaaga aggcgcggaa gcggtccgag cgtcggacgt acctggtggc  420
cgccatgatg tccagcctcg ggttcacgtc catggccgtc gccgccgtgt actctcgctt  480
cagctggcaa atggagggcg gcgaggtgcc ggtgagcgag atgttgggca cgttcgcgct  540
ctccgtcggc gcggcggtcg ggatggagtt ctgggcgcgg tgggcgcacc gggcgctgtg  600
gcacgcctcc ctgtggcaca tgcacgagtc gcaccaccgg ccgcgggagg gccccttcga  660
gctcaacgac gtgttcgcca tcatcaacgc cgtgccggcc atctgtctcc tcgccta     717
```

The β-carotene hydroxylase protein from *Sandersonia aurantiaca* has an amino acid sequence of SEQ ID NO: 36 as follows:

```
Leu Glu Phe Trp Ala Arg Trp Ala His Arg Ala Leu Trp His Ala Ser
 1               5                  10                  15

Leu Trp His Met His Glu Ser His His Arg Ala Arg Glu Gly Pro Phe
            20                  25                  30

Glu Leu Asn Asp Val Phe Ala Ile Thr Asn Ala Val Pro Ala Ile Ala
        35                  40                  45

Leu Leu Ser Tyr Gly Phe Phe His Arg Gly Leu Leu Pro Gly Leu Cys
    50                  55                  60

Phe Gly Ala Gly Leu Gly Ile Thr Leu Phe Gly Met Ala Tyr Met Phe
65                  70                  75                  80

Val His Asp Gly Leu Val His Arg Arg Phe Pro Val Gly Pro Ile Ala
                85                  90                  95

Asn Val Pro Tyr Phe Gln Arg Val Ala Ala His Gln Ile His His
            100                 105                 110

Met Asp Lys Phe Glu Gly Val Pro Tyr Gly Leu Phe Met Gly Pro
        115                 120                 125
```

This protein is encoded by a nucleic acid having the nucleotide sequence of SEQ ID NO: 37 as follows:

```
ttggagttct gggcgagatg ggcgcaccgg gcgctgtggc acgcgtcgct gtggcatatg   60
cacgagtcgc accaacgggc gagggagggn ccgttcgagc tcaacgacgt cttcgccatc  120
acgaacgccg tccctgcgat cgcgctccta tcgtatggat tcttccatcg cggcctcctt  180
cctggactct gcttcggagc tgggctgggg attacgctgt tcgggatggc gtacatgttc  240
gtccacgacg ggctggtgca caggaggttc ccggtggggc ccatcgccaa cgtgccctac  300
ttccagagag tcgcggcggc tcatcagatc caccacatgg acaagtttga agggtgcct   360 tatgggctgt tcatgggtcc c                                            381
``` wherein n is any nucleotide.

The β-carotene hydroxylase protein from soybean has an amino acid sequence of SEQ ID NO: 38 as follows:

```
Met Gly Asp Arg Gly Ser Ser His Ser Leu Leu Ala Gly Gln His Lys
 1               5                  10                  15

His Ser Leu Phe Ala Ser Trp Arg Asn Ser Ile Glu Ala Ile Tyr Pro
            20                  25                  30

Ser Met Ala Ala Gly Len Pro Thr Ala Ala Ile Leu Lys Pro Tyr Asn
        35                  40                  45
```

-continued

```
Leu Val Gln Pro Pro Ile Pro Leu Ser Lys Pro Thr Thr Ser Leu Phe
     50                  55                  60

Phe Asn Pro Leu Arg Cys Phe His His Ser Thr Ile Leu Arg Val Arg
 65                  70                  75                  80

Pro Arg Arg Arg Met Ser Gly Phe Thr Val Cys Val Leu Thr Glu Asp
                 85                  90                  95

Ser Lys Gln Ile Lys Thr Val Glu Gln Gln Gln Gln Val Ile Pro
            100                 105                 110

Gln Ala Val Ser Ala Gly Val Ala Gln Lys Len Ala Arg Lys Lys Ser
            115                 120                 125

Gln Arg Phe Thr Tyr Leu Val Ala Ala Val Met Ser Ser Phe Gly Ile
        130                 135                 140

Thr Ser Met Ala Val Phe Ala Val Tyr Tyr Arg Phe Ser Trp Gln Met
145                 150                 155                 160

Gln Gly Gly Asp Val Pro Trp Ser Gln Met Len Gly Thr Phe Ser Len
                165                 170                 175

Ser Val Gly Ala Ala Val Ala Met Gln Phe Trp Ala Arg Trp Ala His
            180                 185                 190

Arg Ala Leu Trp His Ala Ser Leu Trp His Met His Glu Ser His His
        195                 200                 205

Arg Pro Arg Glu Gly Pro Phe Glu Leu Asn Asp Val Phe Ala Ile Ile
    210                 215                 220

Asn Ala Val Pro Ala Ile Ala Leu Leu Ser Tyr Gly Ile Phe His Lys
225                 230                 235                 240

Gly Leu Val Pro Gly Leu Cys Phe Gly Ala Gly Leu Gly Ile Thr Val
                245                 250                 255

Phe Gly Met Ala Tyr Met Phe Val His Asp Gly Leu Val His Lys Arg
            260                 265                 270

Phe Pro Val Gly Pro Ile Ala Asn Val Pro Tyr Phe Arg Arg Val Ala
        275                 280                 285

Ala Ala His Gln Leu His His Ser Asp Lys Phe Asn Gly Ala Pro Tyr
    290                 295                 300

Gly Leu Phe Leu Gly Pro Lys Glu Val Glu Val Gly Gly Leu Glu
305                 310                 315                 320

Glu Leu Glu Lys Glu Ile Ser Arg Arg Ile Arg Ser Gly Ser
                325                 330
```

This protein is encoded by a nucleic acid having a nucleotide sequence of SEQ ID NO: 39 as follows:

```
atggcggcag gactctccac cgccgcaatc ttaaagccct acaatctcgt ccaaccccca    60
atccctcttt ctaaaccaac cacatcactc ttcttcaacc ccttaagatg tttccatcac   120
agtacaatcc ttcgagttcg acccagaaga agaatgagcg gcttcaccgt tgcgtcctc   180
acggaggatt ccaaagagat caaaacggtc gaacaagaac aagaacaagt gattcctcaa   240
gccgtgtcag caggtgtggc agagaagttg gcgagaaaga agtcccagag gttcacttat   300
ctcgttgcgg ctgtcatgtc tagctttggc atcacctcta tggcagtctt tgccgtttat   360
tatagattct cctggcaaat ggagggtgga gatgttcctt ggtctgaaat gctaggcaca   420
ttttccctct ccgtcggtgc tgctgtggct atggaatttt gggcaagatg ggctcataga   480
gctctttggc atgcttcctt gtggcacatg cacgagtcac accatcgacc aagagaggga   540
ccgttcgagc ttaacgacgt ttttgcgata attaacgctg tccctgcgat cgttcttctc   600
```

-continued

```
tcatacggtt ttttccacaa gggtctggtc cctggcctct gttttggtgc aggccttgga   660
atcacggtgt ttgggatggc ctacatgttt gtccacgatg gattggttca taagagattc   720
cctgtgggtc ccattgccaa cgtgccctac tttagaagag ttgctgctgc tcaccaactc   780
caccattcgg acaaattcaa cggggtgcca tatggcttgt ttttgggacc aaaggaagtt   840
gaagaagtgg gagggctaga agagctagag aaagagataa gtaggagaat caggtccggt   900
tcatgaccat gccactggta ttagctagac ttgtttgaaa gaattgaggg tagagaaagg   960
gaaacaattc aattaatgaa tgaaatgatt tgaatctttt ttttttcttt catacagcta  1020
ttcatattat aatagcagag catataacag aaaaataggg ttaaacgttt atagatgtat  1080
aaacagatca aacatgtgtc aatggaaatg ttctaattgc agcat                 1125
```

The β-carotene hydroxylase protein from tomato has an amino acid sequence of SEQ ID NO: 40 as follows:

```
Met Ala Ala Ala Arg Ile Ser Ala Ser Ser Thr Ser Arg Thr Phe
 1               5                  10                  15

Tyr Phe Arg His Ser Pro Phe Leu Gly Pro Lys Pro Thr Ser Thr
                20                  25                  30

Ser His Val Ser Pro Ile Ser Pro Phe Ser Leu Asn Leu Gly Pro Ile
            35                  40                  45

Leu Arg Ser Arg Arg Lys Pro Ser Phe Thr Val Cys Phe Val Leu Glu
        50                  55                  60

Asp Glu Lys Leu Lys Pro Gln Phe Asp Asp Ala Glu Asp Phe Glu
 65                  70                  75                  80

Lys Lys Ile Glu Glu Gln Ile Leu Ala Thr Arg Leu Ala Glu Lys Leu
                85                  90                  95

Ala Arg Lys Lys Ser Glu Arg Phe Thr Tyr Leu Val Ala Ala Ile Met
            100                 105                 110

Ser Ser Phe Gly Ile Thr Ser Met Ala Val Met Ala Val Tyr Tyr Arg
        115                 120                 125

Phe Ser Trp Gln Met Glu Gly Gly Glu Val Pro Val Thr Glu Met Leu
    130                 135                 140

Gly Thr Phe Ala Leu Ser Val Gly Ala Ala Val Gly Met Glu Phe Trp
145                 150                 155                 160

Ala Arg Trp Ala His Lys Ala Leu Trp His Ala Ser Leu Trp His Met
                165                 170                 175

His Glu Ser His His Lys Pro Arg Glu Gly Pro Phe Glu Leu Asn Asp
            180                 185                 190

Val Phe Ala Ile Thr Asn Ala Val Pro Ala Ile Ala Leu Leu Asn Tyr
        195                 200                 205

Gly Phe Phe His Lys Gly Leu Ile Ala Gly Leu Cys Phe Gly Ala Gly
    210                 215                 220

Leu Gly Ile Thr Val Phe Gly Met Ala Tyr Met Phe Val His Asp Gly
225                 230                 235                 240

Leu Val His Lys Arg Phe Pro Val Gly Pro Val Ala Asn Val Pro Tyr
                245                 250                 255

Leu Arg Lys Val Ala Ala Ala His Ser Leu His His Ser Glu Lys Phe
            260                 265                 270
```

-continued

```
Asn Gly Val Pro Tyr Gly Leu Phe Phe Gly Pro Lys Glu Leu Glu Glu
        275                 280                 285

Val Gly Gly Thr Glu Glu Leu Glu Lys Glu Val Ile Arg Arg Thr Arg
        290                 295                 300

Leu Ser Lys Gly Ser
305
```

The protein is encoded by a nucleic acid having a nucleotide sequence of SEQ ID NO: 41 as follows:

```
atggctgccg ccgccagaat ctccgcctcc tctacctcac gaactttta tttccgtcat    60 tcaccgtttc ttggcccaaa acctacttcg acaacctcac atgtttctcc aatctctcct   120
ttttctctta atctaggccc aattttgagg tctagaagaa aacccagttt cactgtttgc   180
tttgttctcg aggatgagaa gctgaaacct caatttgacg atgaggctga ggattttgaa   240
aagaagattg aggaacagat cttagctact cgcttggcgg agaaactggc taggaagaaa   300
tcggagaggt ttacttatct tgtggctgct ataatgtcta gttttgggat tacttctatg   360
gctgttatgg ctgtttatta cagattttcg tggcaaatgg agggaggaga agttcctgta   420
accgaaatgt tgggtacatt tgctctctct gttggtgctg ctgtaggaat ggagttttgg   480
gcgagatggg cacacaaagc actgtggcat gcttcactat ggcacatgca tgagtcacac   540
cacaaaccaa gagaaggacc ttttgagctg aacgacgttt tcgccataac aaacgctgtt   600
ccagcaatag ccctcctcaa ctatggtttc ttccataaag gcctcattgc cggactatgc   660
ttcggtgctg ggctagggat cacagtattt ggaatggcat acatgtttgt tcacgatggt   720
ttggttcaca agagattccc agttggacct gtagccaatg taccttatct taggaaggtg   780
gctgctgctc attcgcttca tcactcagag aagttcaatg tgtcccata tggcttgttc    840 ttcggaccta aggaactgga agaagtagga gggacggaag agttggaaaa ggaagtgata   900
cgaaggacga gactttcgaa aggatca                                       927
```

See Hirschberg J., "Carotenoid Biosynthesis in Flowering Plants," *Curr Opin Plant Biol* 4:210-218 (2002), which is hereby incorporated by reference in its entirety.

The β-carotene hydroxylase protein from wheat has an animo acid sequence of SEQ ID NO: 42 as follows:

```
Met Ala Val Ala Arg Arg Gly Ala Ala Pro Phe Pro Leu Ala Ala Ala
 1               5                  10                  15

Arg Ala Arg Gly Pro Arg Ala Arg Leu Leu Phe Ala Pro Leu Ser Ala
            20                  25                  30

Leu Pro Arg Arg Ala Ala Ala Pro Ala Met Arg Val Ala Ser Asp Gly
        35                  40                  45

Asn Gly Gly Leu Val Pro Val Arg Pro Gly Gln Glu Ala Glu Asp
        50                  55                  60

Ala Ala Ala Thr Ala Arg Gly Ala Val Ser Asp Arg Ala Ala Arg Lys
 65                  70                  75                  80

Glu Ser Glu Arg Arg Thr Tyr Leu Val Ala Ala Leu Met Ser Ser Leu
                85                  90                  95

Gly Ile Thr Ser Met Asp Gly Val Ala Val Tyr Tyr Arg Phe Ala Trp
            100                 105                 110

Glu Met Glu Gly Gly Glu Ile Pro Val Thr Glu Met Leu Gly Thr Leu
        115                 120                 125
```

```
Ala Leu Ser Val Gly Ala Ala Ala Gly Met Glu Phe Trp Ala Leu Cys
        130                 135                 140
Ala His Arg Ser Leu Trp His Ala Ser Met Trp Asp Met His Gln Phe
145                 150                 155                 160
His His Leu Pro Arg Glu Gly Pro Phe Gln Leu His Asp Val Phe Ala
                165                 170                 175
Ile Leu Asn Gly Val Pro Gly His Gly Pro Pro Trp Val Trp Val Phe
            180                 185                 190
Met Thr Gly Gly Ser Ala Pro Ser Tyr Val Arg Gly Pro Val Leu Gly
        195                 200                 205
Pro Pro Arg Ser Arg Met Gly Lys Leu Cys Val Pro His Gly Leu Gly
        210                 215                 220
Arg Pro Pro His Ser Pro Arg Gly Pro Leu Trp Asn Arg Pro His Phe
225                 230                 235                 240
Pro Gly Asn Leu Ala Gly Pro Ala Leu Val Ala Gly Gln Val Gln His
                245                 250                 255
Pro Ala Ser Gly Leu Phe Pro Pro Gln Pro Gln Val Ala Trp Arg Arg
                260                 265                 270
```

The protein is encoded by a nucleic acid having a nucleotide sequence of SEQ ID NO: 43 as follows:

```
atggccgtcg cgaggcgggg ggccgcgcca ttccccctcg ccgccgcccg cgcccgcggc   60
ccgcgggcgc ggctgctgtt cgcgccgctc tctgcgctcc ccgtcgcgc ggccgcgccc  120
gccatgcgcg tggcgtcaga cggcaacggc ggcggccttg tccccgtccg cccggggcag  180
gaggcggagg acgccgcggc gacggcgcgg ggcgcggtgt cggatcgcgc ggcgaggaag  240
gagtcggagc ggcggacgta cctggtggcc gcgctcatgt ccagcctcgg catcaccctcc  300
atggacggcg tcgccgtcta ctaccgattc gcctgggaaa tggagggcgg cgagattccg  360
gtgacggaga tgctgggcac cttggcactc tccgtgggcg cggcggcggg gatggagttc  420
tgggcgctgt gtgcgcaccg ctcgctgtgg cacgcgtcga tgtgggacat gcaccaattc  480
caccaccttc cccgcgaagg gccctttcag cttcacgacg tgttcgccat tctaaacggc  540
gtacccggcc atggccctcc ctgggtttgg gttttatga ctgggggctc cgccccgtct  600
tatgttcggg gccggtctt gggaccccccc cggtcgcgaa tggcaaaact ttgcgtcccc  660
cacgggcttg gtcgaccgcc ccactccccc aggggccccc tgtggaaccg tccccacttc  720
ccgggaaatc ttgcggggcc agcgttggtc gctggacagg ttcagcatcc ggcatccggg  780
ctcttccccc cccaaccaca agtagcgtgg cggcgg                            816
```

The β-carotene hydroxylase protein from lettuce has an amino acid sequence of SEQ ID NO: 44 as follows:

```
Met Ala Ala Ala Ile Ala Val Ala Ser Ser Ser Arg Ser Phe Arg
1               5                   10                  15
Leu Thr Arg Met Pro Phe Leu Gly Gln Lys Pro Thr Ser Arg Thr Ser
            20                  25                  30
Gln Phe Pro Ser Ser Ile Arg Asn Phe Asp Pro Ile Ala Arg Phe Arg
        35                  40                  45
Arg Thr Pro Arg Leu Thr Val Cys Phe Val Ala Gly Asp Gln Lys Leu
    50                  55                  60
Glu Thr Gln Ile Val Glu Asp Asn Gly Ser Gly Asn Asn Pro Gly Pro
65                  70                  75                  80
```

```
Ser Gly Gly Glu Gly Ser Asp Glu Glu Ile Thr Gln Val Met Leu Ser
                85                  90                  95
Ser Thr Ser Asn Arg Val Val Glu Glu Lys Met Ala Arg Lys Lys Ser
            100                 105                 110
Glu Arg Phe Thr Tyr Leu Val Ala Ala Ile Met Ser Thr Phe Gly Ile
        115                 120                 125
Thr Ser Met Ala Val Met Ala Val Tyr Tyr Arg Phe Ser Trp Gln Met
    130                 135                 140
Glu Gly Gly Asp Val Pro Phe Val Glu Met Phe Gly Thr Phe Ala Leu
145                 150                 155                 160
Ser Val Gly Ala Ala Val Gly Met Glu Tyr Trp Ala Arg Trp Ala His
                165                 170                 175
Glu Ala Leu Trp His Ala Ser Leu Trp His Thr His Glu Ser His His
            180                 185                 190
Lys Pro Arg Glu Gly Pro Phe Glu Leu Asn Asp Val Phe Ala Ile Ile
        195                 200                 205
Asn Ala Val Pro Ala Ile Ala Leu Leu Asn Tyr Gly Phe Phe His Lys
    210                 215                 220
Gly Ile Phe Pro Gly Leu Cys Phe Gly Ala Gly Leu Gly Ile Thr Val
225                 230                 235                 240
Phe Gly Met Ala Tyr Met Phe Val His Asp Gly Leu Val His Arg Arg
                245                 250                 255
Phe Gln Val Gly Pro Ile Ala Asn Val Pro Tyr Leu Arg Arg Val Ala
            260                 265                 270
Ala Ala His Gln Leu His His Thr Glu Glu Phe Asn Gly Val
        275                 280                 285
```

The protein is encoded by a nucleic acid having a nucleotide sequence of SEQ ID NO: 45 as follows:

```
atggcggcag cagcaatcgc cgtcgcttcc agttcacgct ccttccgttt aacccgaatg    60
ccgttcctag gtcaaaaacc cacatctaga acttctcaat ttccatcctc tatcagaaac   120
ttcgacccga ttgctcggtt ccgacggacg cctaggttga cagtctgttt cgttgccgga   180
gaccagaagt tagagaccca aattgttgag gacaacggca gtggtaacaa tcctggacct   240
agcggcggcg agggttcaga tgaggaaata actcaggtga tgttgagtag tactagtaac   300
cgcgtcgtag aggaaaaaat ggctaggaag aagtccgaac gctttactta ccttgtcgca   360
gctatcatgt ctacttttgg gattacttcc atggctgtta tggctgttta ttacaggttt   420
tcatggcaaa tggagggtgg agatgttcct tttgtggaga tgtttgggac atttgctctc   480
tctgttggcg ctgcggtagg aatggagtat gggcgagat gggcgcatga agctctatgg   540
catgcttctt tatggcacac gcatgagtca caccataaac cccgagaagg ccccttcgag   600
ctcaacgacg tgttcgcgat tataaacgcc gttccggcga ttgcgttact gaactacggc   660
ttcttccata aaggaatatt tcccggcctc tgtttcggcg ctgggcttgg gataacggtg   720
tttggaatgg cgtacatgtt cgtccacgat ggccttgttc ataggagatt ccaagtgggt   780
cccattgcaa atgtccccta ccttcgaaga gttgcagctg ctcatcagtt gcatcacaca   840
gaagaattta atg gggtac                                                859
```

In one aspect of the present invention, the nucleic acid construct results in interference of β-carotene hydroxylase expression by sense or co-suppression in which the nucleic acid molecule of the construct is in a sense (5′→3′) orientation. Co-suppression has been observed and reported in many plant species and may be subject to a transgene dosage effect or, in another model, an interaction of endogenous and transgene transcripts that results in aberrant mRNAs (Senior, "Uses of Plant Gene Silencing," *Biotechnology and Genetic Engineering Reviews* 15:79-119 (1998); Waterhouse et al., "Exploring Plant Genomes by RNA-Induced Gene Silencing," *Nature Review: Genetics* 4: 29-38 (2003), which are hereby incorporated by reference in their entirety). A construct with the nucleic acid molecule in the sense orientation may also give sequence specificity to RNA silencing when inserted into a vector along with a construct of both sense and antisense nucleic acid orientations as described infra (Wesley et al., "Construct Design for Efficient, Effective and High-Throughput Gene Silencing in Plants," *Plant Journal* 27(6) 581-590 (2001), which is hereby incorporated by reference in its entirety).

In another embodiment of the present invention, the nucleic acid construct results in interference of β-carotene hydroxylase expression by the use of antisense suppression in which the nucleic acid molecule of the construct is an antisense (3'→5') orientation. The use of antisense RNA to downregulate the expression of specific plant genes is well known (van der Krol et al., *Nature*, 333:866-869 (1988) and Smith et al., *Nature*, 334:724-726 (1988), which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). In the target cell, the antisense nucleic acids hybridize to a target nucleic acid and interfere with transcription, and/or RNA processing, transport, translation, and/or stability. The overall effect of such interference with the target nucleic acid function is the disruption of protein expression (Baulcombe, "Mechanisms of Pathogen-Derived Resistance to Viruses in Transgenic Plants," *Plant Cell* 8:1833-44 (1996); Dougherty, et al., "Transgenes and Gene Suppression Telling us Something New?," *Current Opinion in Cell Biology* 7:399-05 (1995); Lomonossoff, "Pathogen-Derived Resistance to Plant Viruses," *Ann. Rev. Phytopathol.* 33:323-43 (1995), which are hereby incorporated by reference in their entirety). Accordingly, one aspect of the present invention involves a construct which contains the nucleic acid molecule of the present invention being inserted into the construct in antisense orientation.

Interference of β-carotene hydroxylase expression is also achieved in the present invention by the generation of double-stranded RNA ("dsRNA") through the use of inverted-repeats, segments of gene-specific sequences oriented in both sense and antisense orientations. In one embodiment of this aspect of the present invention, sequences in the sense and antisense orientations are linked by a third segment, and inserted into a suitable expression vector having the appropriate 5' and 3' regulatory nucleotide sequences operably linked for transcription. The expression vector having the modified nucleic acid molecule is then inserted into a suitable host cell or subject. In the present invention the third segment linking the two segments of sense and antisense orientation may be any nucleotide sequence such as a fragment of the β-glucuronidase ("GUS") gene. In another embodiment of this aspect of the present invention, a functional (splicing) intron of β-carotene hydroxylase may be used for the third (linking) segment, or, in yet another aspect of the present invention, other nucleotide sequences without complementary components in the β-carotene hydroxylase gene may be used to link the two segments of sense and antisense orientation (Chuang et al., "Specific and Heritable Genetic Interference by Double-Stranded RNA in *Arabidopsis thaliana*," *Proc. Nat'l Academy of Sciences USA* 97(9):4985-4990 (2000); Smith et al., "Total Silencing by Intron-Spliced Hairpin RNAs," *Nature* 407:319-320 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6): 581-590 (2001), which are hereby incorporated by reference in their entirety). In any of the embodiments with inverted repeats of β-carotene hydroxylase, the sense and antisense segments may be oriented either head-to-head or tail-to-tail in the construct.

Another aspect of the present invention involves using hairpin RNA ("hpRNA") which may also be characterized as dsRNA. This involves RNA hybridizing with itself to form a hairpin structure that comprises a single-stranded loop region and a base-paired stem. Though a linker may be used between the inverted repeat segments of sense and antisense sequences to generate hairpin or double-stranded RNA, the use of intron-free hpRNA can also be used to achieve silencing of β-carotene hydroxylase expression.

Alternatively, in another aspect of the present invention, a plant may be transformed with constructs encoding both sense and antisense orientation molecules having separate promoters and no third segment linking the sense and antisense sequences (Chuang et al., "Specific and Heritable Genetic Interference by Double-Stranded RNA in *Arabidopsis thaliana*," *Proc. Nat'l Academy of Sciences USA* 97(9): 4985-4990 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety).

The β-carotene hydroxylase nucleotide sequences of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y.: Cold Spring Harbor Press (1989), and Ausubel et al., *Current Protocols in Molecular Biology*, New York, N.Y.: John Wiley & Sons (1989), which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of Agrobacterium tumefaciens. Fraley et al., "Expression of Bacterial Genes in Plant Cells," Proc. Nat'l Acad. Sci. 80:4803-4807 (1983), which is hereby incorporated by reference in its entirety.

Further improvement of this technique led to the development of the binary vector system. Bevan, "Binary Agrobacterium Vectors for Plant Transformation," Nucleic Acids Res. 12:8711-8721 (1984), which is hereby incorporated by reference in its entirety. In this system, all the T-DNA sequences (including the borders) are removed from the pTi, and a second vector containing T-DNA is introduced into Agrobacterium tumefaciens. This second vector has the advantage of being replicable in E. coli as well as A. tumefaciens, and contains a multiclonal site that facilitates the cloning of a transgene. An example of a commonly-used vector is pBin19. Frisch et al., "Complete Sequence of the Binary Vector Bin19," Plant Molec. Biol. 27:405-409 (1995), which is hereby incorporated by reference in its entirety. In the present invention, the parent vector used was pGPTV-KAN. Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase (NOS) gene promoter, from Agrobacterium tumefaciens (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," Proc. Natl. Acad. Sci. 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog. Schena et al., "A Steroid-Inducible Gene Expression System for Plant Cells," Proc. Natl. Acad. Sci. USA 88:10421-5 (1991); Aoyama et al., "A Glucocorticoid-Mediated Transcriptional Induction System in Transgenic Plants," Plant J. 11:605-612 (1997); and McNellis et al., "Glucocorticoid-Inducible Expression of a Bacterial Avirulence Gene in Transgenic Arabidopsis Induces Hypersensitive Cell Death, Plant J. 14(2):247-57 (1998), which are hereby incorporated by reference in their entirety. In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 to Shewmaker et al., which is hereby incorporated by reference in its entirety). One of the promoters suitable in the present invention is the tuber-specific granule bound starch synthase (GBSS) promoter.

A number of tissue- and organ-specific promoters have been developed for use in genetic engineering of plants (Potenza et al., "Targeting Transgene Expression in Research, Agricultural, and Environmental Applications: Promoters used in Plant Transformation," In Vitro Cell. Dev. Biol. Plant 40:1-22 (2004), which is hereby incorporated by reference in its entirety). Examples of such promoters include those that are floral-specific (Annadana et al., "Cloning of the Chrysanthemum UEP1 Promoter and Comparative Expression in Florets and Leaves of Dendranthema grandiflora," Transgenic Res. 11:437-445 (2002), which is hereby incorporated by reference in its entirety), seed-specific (Kluth et al., "5' Deletion of a gbss1 Promoter Region Leads to Changes in Tissue and Developmental Specificities," Plant Mol. Biol. 49:669-682 (2002), which is hereby incorporated by reference in its entirety), root-specific (Yamamoto et al., "Characterization of cis-acting Sequences Regulating Root-Specific Gene Expression in Tobacco," Plant Cell 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," Proc. Natl. Acad. Sci. USA 99:1092-1097 (2002), which is hereby incorporated by reference in its entirety), and tuber/storage organ-specific (Visser et al., "Expression of a Chimaeric Granule-Bound Starch Synthase-GUS gene in transgenic Potato Plants," Plant Mol. Biol.

17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

The nucleic acid construct of the present invention also includes an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313 (6005):810-812 (1985), which is hereby incorporated by reference in its entirety). Virtually any 3' regulatory region known to be operable in plants would be suitable for use in conjunction with the present invention.

The different components described above can be ligated together to produce the expression systems which contain the nucleic acid constructs of the present invention, using well known molecular cloning techniques as described in Sambrook et al., *Molecular Cloning: A Laboratory Manual*, Second Edition Cold Spring Harbor, N.Y.: Cold Spring Harbor Press (1989), and Ausubel et al. *Current Protocols in Molecular Biology*, New York, N.Y.: John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 µm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or Ri) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., *Proc. Natl. Acad. Sci. USA* 79:1859-63 (1982), which is hereby incorporated by reference in its entirety). The nucleic acid molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures*, Vol. 1, New York, N.Y.: MacMillan Publishing Co. (1983); Vasil, ed., *Cell Culture and Somatic Cell Genetics of Plants*, Vol. I (1984) and Vol. III (1986), Orlando: Acad. Press; and Fitch et al., "Somatic Embryogenesis and Plant Regeneration from Immature Zygotic Embryos of *Papaya* (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferase II ("nptII") gene which confers kanamycin resistance (Fraley et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y.: Cold Spring Harbor Press (1989), which is hereby incorporated by reference in its entirety).

After the fusion gene containing a nucleic acid construct of the present invention is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants. The component parts and fruit of such plants are encompassed by the present invention.

The present invention can be utilized in conjunction with a wide variety of plants or their seeds. Suitable plants are any plant with a β-carotene hydroxylase gene, including dicots and monocots. Plants can include: *Arabidopsis*, barley, citrus, cotton, crocus, daffodil, grape, marigold, maize, *Medicago truncatula*, onion, pepper, pine, potato, rice, *Sandersonia aurantiaca*, sorgum, soybean, tomato, lettuce, and wheat.

Another aspect of the present invention is a method of enhancing beta-carotene content. This method involves providing a transgenic plant or plant seed transformed with a nucleic acid construct having a nucleic acid molecule configured to silence β-carotene hydroxylase, a 5' DNA promoter sequence, and a 3' terminator sequence. The method involves growing the transgenic plant or a transgenic plant grown from the transgenic plant seed under conditions effective to enhance beta-carotene content of the transgenic plant or the plant grown from the transgenic plant seed.

EXAMPLES

Example 1

Construction of Plant Expression Plasmid with Beta-Carotene Hydroxylase Gene in Inverted Orientations and Cauliflower Mosaic Virus Promoter In one construct, the cauliflower mosaic virus (CaMV 35S) promoter was chosen for fusion with a segment of the β-carotene hydroxylase gene in zeaxanthin-accumulating potato plants. Identical segments in inverted orientations of the β-carotene hydroxylase gene (SEQ ID NO: 1) from chromosome 6 of *Solanum tuberosum* were fused to the CaMV 35S promoter. The intervening linker segment is a DNA sequence of the β-glucuronidase gene with the following sequence:

```
                                        SEQ ID NO: 46
ATCTACCCGC TTCGCGTCGG CATCCGGTCA TGGCAGTGA

AGGGCCAACA GTTCCTGATT AA
```

The plasmid chosen for this construct was p35S-Cha. The map for plasmid vector p35S-Cha is shown in FIG. 2A which describes the elements of the vector. The terminator used was soybean vspB 3'-end sequence, and the parent vector was pGPTV-KAN with the neomycin phosphotransferase II gene, transferring kanamycin resistance for transgene selection. The binary vector plasmid, p35S-Cha containing a segment of the beta-carotene hydroxylase gene in both orientations, the linker segment, a CaMV 35S promoter, and the vspB terminator sequence was obtained by ligating the expression cassette into pGPTV-Kan (Becker et al., "New Plant Binary Vectors with Selectable Markers Located Proximal to the Left T-DNA Border," *Plant Mol. Biol.* 20:1195-1197 (1992), which is hereby incorporated by reference in its entirety). The CaMV 35S promoter was chosen because it is a strong constitutive promoter.

Established methods for recombinant DNA manipulations were used to prepare the expression vectors (Sambrook et al., *Molecular Cloning: A Laboratory Manual*, Second Edition, Cold Spring Harbor, N.Y.: Cold Spring Harbor Press, (1989), which is hereby incorporated by reference in its entirety).

The p35S-Cha expression cassette was introduced into electrocompetent *Escherichia coli* DH5α cells by electroporation. Following electroporation, SOC medium (2% bacto-tryptone, 0.5% bacto-yeast extract, 0.05% NaCl, 20 mM glucose) was added, and the cells were incubated at 37° C. for 1 hour. The cells were plated onto LB medium (1% bacto-tryptone, 0.5% bacto-yeast extract, 1% NaCl) solidified with 1.2% Bactoagar, and containing 50 mg/l kanamycin. Cultures were incubated overnight at 37° C. Several bacterial colonies were picked, transferred to 3 ml of LB medium containing 50 mg/l kanamycin, and cultured overnight at 37° C. in a shaking incubator. DNA was isolated, and the integrity of the expression vector was verified by sequencing analysis. The p35S-Cha expression vector DNA was stored at −20° C.

Example 2

Construction of Plant Expression Plasmid with Beta-Carotene Hydroxylase Gene in Inverted Orientations and Tuber-Specific Granule Bound Starch Synthase Promoter In one construct, the tuber-specific granule bound starch synthase (GBSS) promoter was chosen for fusion with a segment of the β-carotene hydroxylase gene in zeaxanthin-accumulating potato plants. Identical segments in inverted orientations of the β-carotene hydroxylase gene (SEQ ID NO: 2) from chromosome 6 of *Solanum tubersosum* were fused to the GBSS promoter. The intervening linker segment is the DNA sequence of SEQ ID NO: 46.

Figure 2B:
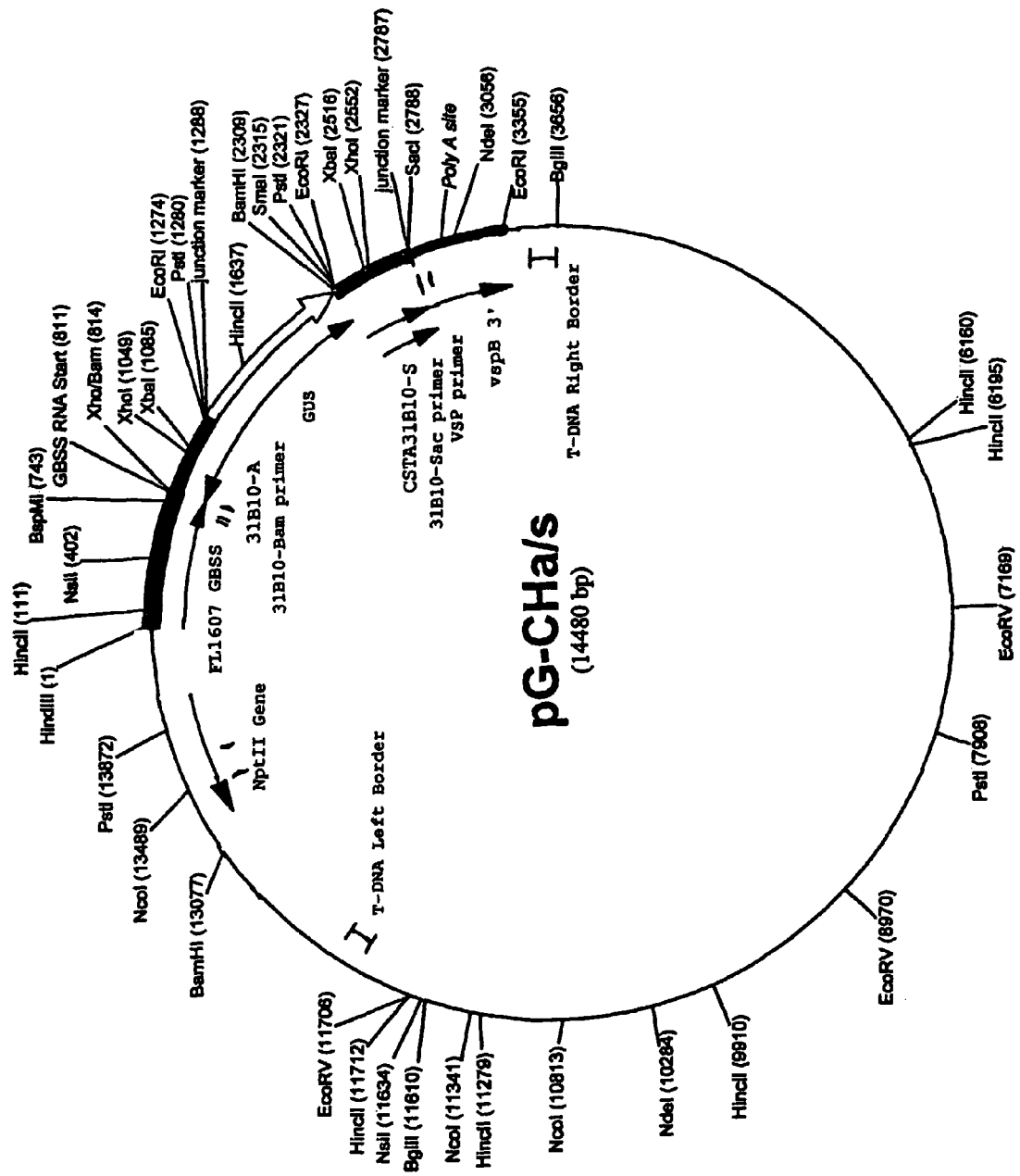

The plasmid chosen for this construct was pG-Cha. The map for plasmid vector pG-Cha is shown in FIG. 2B which describes the elements of the vector. The terminator used was soybean vspB 3'-end sequence, and the parent vector was pGPTV-KAN with the neomycin phosphotransferase II gene, transferring kanamycin resistance for transgene selection. The binary vector plasmid, pG-Cha containing a segment of the β-carotene hydroxylase gene in both orientations, the linker segment, a GBSS promoter, and the vspB terminator sequence was obtained by ligating the expression cassette into pGPTV-Kan (Becker et al., "New Plant Binary Vectors with Selectable Markers Located Proximal to the Left T-DNA Border," *Plant Mol. Biol.* 20:1195-1197 (1992), which is hereby incorporated by reference in its entirety). The GBSS promoter was chosen as an alternative to the CaMV 35S as GBSS is tuber-specific and would not cause unwanted silencing in leaf tissues. Established methods for recombinant DNA manipulations were used to prepare the expression vectors (Sambrook et al., *Molecular Cloning: A Laboratory Manual*, Second Edition, Cold Spring Harbor, N.Y.: Cold Spring Harbor Press, (1989), which is hereby incorporated by reference in its entirety).

The pG-Cha expression cassette was introduced into electrocompetent *Escherichia coli* DH5α cells by electroporation. Following electroporation, SOC medium (2% bacto-tryptone, 0.5% bacto-yeast extract, 0.05% NaCl, 20 mM glucose) was added, and the cells were incubated at 37° C. for 1 hour. The cells were plated onto LB medium (1% bacto-tryptone, 0.5% bacto-yeast extract, 1% NaCl) solidified with 1.2% Bactoagar, and containing 50 mg/l kanamycin. Cultures were incubated overnight at 37° C. Several bacterial colonies were picked, transferred to 3 ml of LB medium containing 50 mg/l kanamycin, and cultured overnight at 37° C. in a shaking incubator. DNA was isolated, and the integrity of the expression vector was verified by sequencing analysis. The pG-Cha expression vector DNA was stored at −20° C.

Example 3

Plasmid Transfer to *Agrobacterium* and Plant Transformation

The next stage was to transfer the plasmid vector to the bacterium *Agrobacterium tumefaciens*. This bacterium was then used to inoculate plant cells and transfer the beta-carotene hydroxylase gene in inverted orientations with an intervening DNA segment, flanked by T-DNA borders, to the plant. Potato (*Solanum tuberosum* 91E22) were used as hosts for genetic transformation by *Agrobacterium tumefaciens* containing p35S-Cha and pG-Cha. Transformations were carried out by stem cultivation methods. For each plasmid transfer and plant transformation, approximately 100 stem internode segments between 0.5 cm and 1 cm in length were excised from six-week-old plants and incubated per 50 ml of *Agrobacterium tumefaciens* strain LBA4404 containing either P35S-Cha or pG-Cha for ten minutes. Internodes were then blotted dry on sterile filter paper and transferred to a callus induction medium containing Murashige and Skoog salts (Caisson Laboratories, Sugar City, Id.), 2 mg/l glycine, 0.5 mg/l nicotinic acid, 0.5 mg/l pyridoxine, 0.4 mg/l thiamine, 0.25 mg/l folic acid, 0.05 mg/l D-biotin, 100 mg/l myoinositol, 30 g/l sucrose (grade II, Phyto Technology Laboratories, Shawnee Mission, Kans.), 1 mg/l benzyladenine, 2 mg/l naphtaleneacetic acid (added after autoclaving), and 6 g/l Agar/Agar (Sigman, St. Louis, Mo.). The pH of the medium was adjusted to 5.6 before the addition of the Agar/Agar. One hundred explants were cultured per 100×20 mm Petri plates and maintained at 24±1° C. under a photoperiod of 16 h (light)/8 h (dark) at 74 HE m$^{-2}$s$^{-1}$ for 48 hours before transfer for selective plant regeneration.

Example 4

Regeneration of Transgenic Potato Plants

The potato explants were incubated in the *Agrobacterium* suspension and co-cultivated at 24° C. under a photoperiod of 16 h (light)/8 h (dark) at 74 μE m$^{-2}$s$^{-1}$ for 48 hours. After 48 hours, the internode segments were transferred to selective plant regeneration medium containing Murashige and Skoog salts (Caisson Laboratories, Sugar City, Id.), 1 mg/l thiamine, 0.5 mg/l nicotinic acid, 0.5 mg/l pyridoxine, 100 mg/l myo-inositol, 30 g/l sucrose, 0.1 mg/l indole-3-acetic acid (added after autoclaving), 3.4 mg/l zeatin riboside (added after autoclaving), 500 mg/l carbenicillin (Phytotechnology Laboratories) (added after autoclaving), 75 mg/l kanamycin monosulfate (added after autoclaving), and 8 g/l Agar/Agar. The pH of the medium was adjusted to 5.9 before the addition of Agar/Agar. Twenty-five internode segments were cultured per 100×20 mm Petri plate, and the plates were sealed with 0.5 inch Micropore Tape (3M HealthCare, St. Paul, Minn.). Explants were transferred weekly for one month to fresh selective plant regeneration medium, then every ten to fourteen days after the one-month period. All cultures were maintained at 24±1° C. under a photoperiod of 16 h (light)/8 h (dark) at 74 μm$^{-2}$s$^{-}$.

When regenerants were approximately 0.5 cm to 1 cm in length, they were excised and transferred to selective rooting medium which contained Murashige and Skoog salts (Caisson Laboratories, Sugar City, Id.), 0.4 mg/l thiamine, 0.1 mg/l myoinositol, 500 mg/l carbenicillin (added after autoclaving) and 75 mg/l kanamycin (added after autoclaving). Five regenerants were cultured per GA7 Magenta box (Phytotechnology Laboratories). For extended maintenance of the transgenic lines, the shoot tip from each plant was transferred to test tubes containing rooting medium without kanamycin and carbenecillin.

Example 5

Analysis by PCR for Selection of Transformed Plants

Plants were initially screened by selecting those that rooted on rooting medium containing kanamycin. Confirmation of the beta-carotene hydroxylase gene in the plants was shown by PCR analysis. DNA was isolated from leaf material for PCR analysis by homogenization in a buffer of 0.2M Tris, 0.25M NaCl, 25 mM EDTA, and 5 mg/ml SDS. The DNA was precipitated in isopropanol, and the resultant pellet was washed in 70% ethanol. The primers used to detect the presence of the neomycin phosphotransferase II gene were as follows:

```
SEQ ID NO: 47  Forward 5'-GGGTGGAGAGGCTATTC-3'

SEQ ID NO: 48  Reverse 5'-GAAGGCGATAGAAGGCG-3'
```

Transgenic lines in which a 735 base pair fragment was amplified, were selected.

Example 6

Propagation of Transgenic Lines

Figure 3:
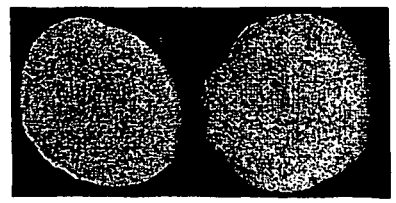
FIG. 3 shows a comparison of wild type *Solanum tuberosum* 91E22 tubers with tubers of silenced transgenic lines. It is visually apparent that there is a decrease in zeaxanthin content in the tubers of silenced lines based on the change from yellow flesh in wild type 91E22 tubers (left) to white in transgenic lines (right).

No differences were observed for growth rates of the transgenic lines compared to the wild types. There were differences in the number of tubers, tuber size, and weight for the various lines tested. A total of 185 plants was recovered from transformations with the pG-Cha plasmid, and 250 plants were recovered with p35S-Cha. Of these, 118 pG-Cha lines and 45 p35S-Cha lines were transferred to the greenhouse for tuber production. The PCR positive lines were transferred first to Jiffy 7 pots, placed in a tray, and covered with a plastic dome. Over the course of one week, the dome was gradually lifted to give a gradual acclimation to greenhouse conditions. After one week, the dome was removed. In about two weeks, or when the roots were growing through the Jiffy 7 pots, the plants were transferred to soil-less potting mix in 5 gallon pots. Tubers were harvested 4 months after the transfer to the Jiffy 7 pots. Morphology of all the transgenic lines was similar to wild type 91E22. It was visually apparent that there was a decrease in zeaxanthin content in the tubers based on the change from yellow flesh in wild type Solanum tubersosum 91E22 tubers to white in the transgenic lines (FIG. 3).

Example 7

HPLC Analysis

Figure 4:
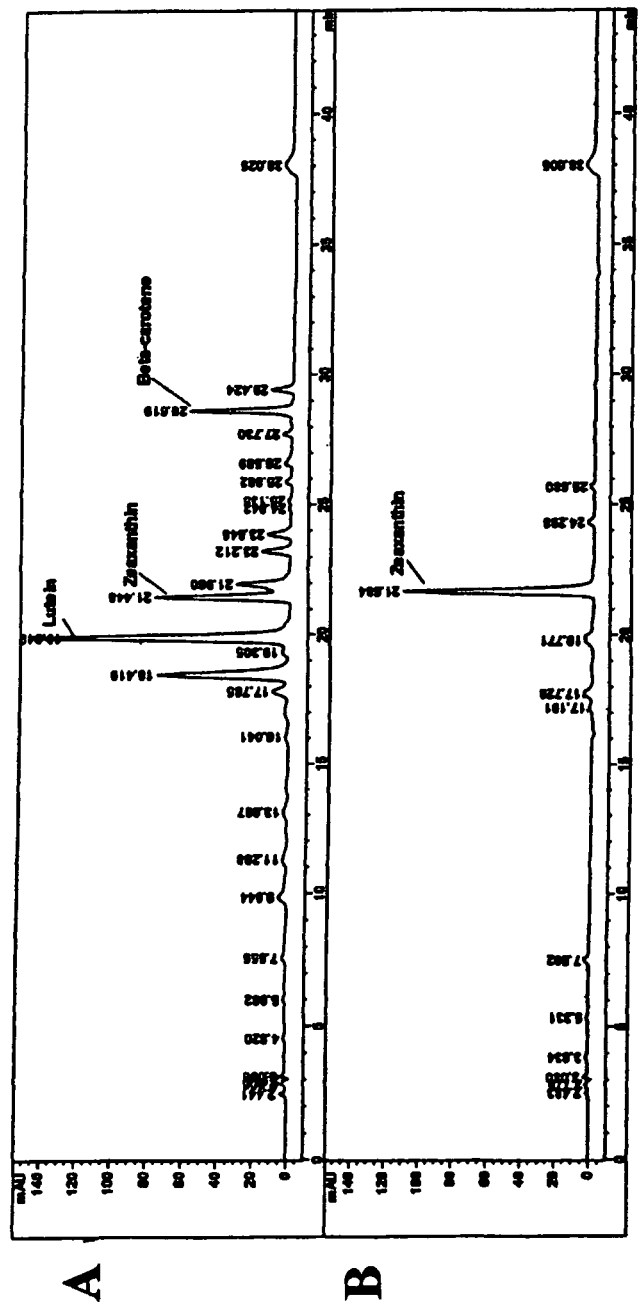
FIGS. 4A-B show the results of HPLC analysis performed on tubers harvested from p35S-Cha transgenic lines (FIG. 4A) and wild type 91E22 controls (FIG. 4B).

HPLC analysis was performed on 40 transgenic lines. The total carotenoid content varied for each transgenic line, and the amount of beta-carotene also differed. An example of the differences in the carotenoid profiles based on HPLC between the wild type line and one of the transgenic lines, p35S-Cha, can be seen in FIGS. 4A-B. The carotenoid profile of p35S-Cha differed from the wild type line in zeaxanthin, beta-carotene, and lutein. The zeaxanthin content was significantly decreased in the transgenic lines as expected from the use of RNA silencing of the β-carotene hydroxylase gene. The amount of beta-carotene in the wild type was present in only trace amounts, whereas there was a significant increase in the amount in p35S-Cha. This trend was similar in all transgenic lines; however, the amounts of lutein, beta-carotene, and zeaxanthin differed for each line. See FIG. 5.

Although preferred embodiments have been depicted and described in detail herein, it will be apparent to those skilled in the relevant art that various modifications, additions, substitutions, and the like can be made without departing from the spirit of the invention and these are, therefore, considered to be within the scope of the invention as defined in the claims which follow.

What is claimed:

1. A nucleic acid construct comprising:
   (a) a nucleic acid molecule configured to silence β-carotene hydroxylase expression, wherein the nucleic acid molecule
      (i) encodes β-carotene hydroxylase comprising the amino acid sequence of SEQ ID NO: 1,
      (ii) is an antisense form of the nucleic acid molecule that encodes β-carotene hydroxylase comprising the amino acid sequence of SEQ ID NO: 1, or
      (iii) is a combination of (i) and (ii), and
   wherein either (i), (ii), or (iii) is positioned in the nucleic acid construct to result in suppression or interference with endogenous mRNA encoding β-carotene hydroxylase;
   (b) a 5' DNA heterologous promoter sequence, wherein the DNA promoter is a tissue-specific promoter or an organ-specific promoter; and
   (c) a 3' terminator sequence,
   wherein the nucleic acid molecule, the promoter, and the terminator are operatively coupled to permit transcription of the nucleic acid molecule.

2. The nucleic acid construct according to claim 1, wherein the nucleic acid molecule encodes the β-carotene hydroxylase and is in sense orientation.

3. The nucleic acid construct according to claim 1, wherein the nucleic acid molecule is the antisense form of the nucleic acid molecule encoding the β-carotene hydroxylase.

4. The nucleic acid construct according to claim 1, wherein the nucleic acid molecule comprises a first segment encoding the β-carotene hydroxylase, a second segment in an antisense form of the first segment, and a third segment linking the first and second segments.

5. An expression vector comprising the nucleic acid construct according to claim 1.

6. A host cell transformed with the nucleic acid construct according to claim 1.

7. The host cell according to claim 6, wherein the host cell is a bacterial cell or a plant cell.

8. The host cell according to claim 7, wherein the host cell is a plant cell.

9. The plant cell according to claim 8, wherein the plant cell is selected from the group consisting of *Arabidopsis*, barley, citrus, cotton, crocus, daffodil, grape, marigold, maize, *Medicago truncatula*, onion, pepper, pine, potato, rice, *Sandersonia aurantiaca*, sorghum, soybean, tomato, lettuce, and wheat.

10. A plant transformed with the nucleic acid construct according to claim 1.

11. The plant according to claim 10, wherein the nucleic acid molecule encodes the β-carotene hydroxylase and is in sense orientation.

12. The plant according to claim 10, wherein the nucleic acid molecule is the antisense form of the nucleic acid molecule encoding the β-carotene hydroxylase.

13. The plant according to claim 10, wherein the plant is transformed with first and second of the nucleic acid constructs with the first nucleic acid construct encoding the β-carotene hydroxylase in sense orientation and the second nucleic acid construct encoding the β-carotene hydroxylase in antisense form.

14. The plant according to claim 10, wherein the nucleic acid molecule comprises a first segment encoding the β-carotene hydroxylase, a second segment in an antisense form of the first segment, and a third segment linking the first and second segments.

15. The plant according to claim 10, wherein the plant is selected from the group consisting of *Arabidopsis*, barley, citrus, cotton, crocus, daffodil, grape, marigold, maize, *Medicago truncatula*, onion, pepper, pine, potato, rice, *Sandersonia aurantiaca*, sorghum, soybean, tomato, lettuce, and wheat.

16. A component part of the plant according to claim 10.

17. A fruit of the plant according to claim 10.

18. A plant seed produced from the plant according to claim 10.

19. A plant seed transformed with the nucleic acid construct according to claim 1.

20. The plant seed according to claim 19, wherein the nucleic acid molecule encodes the β-carotene hydroxylase and is in sense orientation.

21. The plant seed according to claim 19, wherein the nucleic acid molecule is the antisense form of the nucleic acid molecule encoding the β-carotene hydroxylase.

22. The plant seed according to claim 19, wherein the plant seed is transformed with first and second of the nucleic acid constructs with the first nucleic acid construct encoding the β-carotene hydroxylase in sense orientation and the second nucleic acid construct encoding the β-carotene hydroxylase in antisense form.

23. The plant seed according to claim 19, wherein the nucleic acid molecule comprises a first segment encoding the β-carotene hydroxylase, a second segment in an antisense form of the first segment, and a third segment linking the first and second segments.

24. A method of enhancing beta-carotene content, said method comprising:
   providing a transgenic plant seed transformed with a nucleic acid construct comprising:
   (a) a nucleic acid molecule configured to silence β-carotene hydroxylase expression, wherein the nucleic acid molecule
      (i) encodes β-carotene hydroxylase comprising the amino acid sequence of SEQ ID NO: 1,
      (ii) is an antisense form of the nucleic acid molecule that encodes β-carotene hydroxylase comprising the amino acid sequence of SEQ ID NO: 1, or
      (iii) is a combination of (i) and (ii), and
      wherein either (i), (ii), or (iii) is positioned in the nucleic acid construct to result in suppression or interference with endogenous mRNA encoding β-carotene hydroxylase;
   (b) a 5' DNA heterologous promoter sequence, wherein the DNA promoter is a tissue-specific promoter or an organ-specific promoter; and
   (c) a 3' terminator sequence,
      wherein the nucleic acid molecule, the promoter, and the terminator are operatively coupled to permit transcription of the nucleic acid molecule, and
   growing the transgenic plant or a transgenic plant grown from the transgenic plant seed under conditions effective to enhance the beta-carotene content of said transgenic plant or said plant grown from the transgenic plant seed.

25. The method according to claim 24, wherein the transgenic plant is provided.

26. The method according to claim 24, wherein the transgenic plant seed is provided.

27. The method according to claim 24, wherein said providing comprises:
   providing the nucleic acid construct and transforming a plant cell with the nucleic acid construct.

28. The method according to claim 27, wherein the nucleic acid molecule encodes the β-carotene hydroxylase in sense orientation.

29. The method according to claim 27, wherein the nucleic acid molecule is the antisense form of the nucleic acid molecule encoding the β-carotene hydroxylase.

30. The method according to claim 27, wherein the plant cell is transformed with first and second of the nucleic acid constructs with the first nucleic acid construct encoding the β-carotene hydroxylase in sense orientation and the second nucleic acid construct encoding the β-carotene hydroxylase in antisense form.

31. The method according to claim 27, wherein the nucleic acid molecule comprises a first segment encoding the β-carotene hydroxylase, a second segment in an antisense form of the first segment, and a third segment linking the first and second segments.

32. The method according to claim 27 further comprising: propagating plants from the transformed plant cell.

33. The method according to claim 27, wherein said transforming comprises *Agrobacterium*-mediated transformation, vacuum infiltration, biolistic transformation, electroporation, micro-injection, polyethylene-mediated transformation, or laser-beam transformation.

34. The method according to claim 27, wherein the plant cell is selected from the group consisting of: *Arabidopsis*, barley, citrus, cotton, crocus, daffodil, grape, marigold, maize, *Medicago truncatula*, onion, pepper, pine, potato, rice, *Sandersonia aurantiaca*, sorghum, soybean, tomato, lettuce, and wheat.

35. The nucleic acid construct according to claim 1, wherein the promoter is a tuber-specific promoter.

36. The nucleic acid construct according to claim 35, wherein the promoter is a GBSS promoter.

37. The nucleic acid construct according to claim 1, wherein the nucleic acid construct is configured to selectively silence β-carotene hydroxylase expression in fruit.

38. The nucleic acid construct according to claim 1, wherein the nucleic acid construct is configured to silence tuber β-carotene hydroxylase expression.

39. The nucleic acid construct according to claim 1, wherein the nucleic acid molecule is configured to silence expression of β-carotene hydroxylase expression in a 4-month old plant.

40. The method according to claim 24, wherein the transgenic plant or a transgenic plant grown from the transgenic plant seed is grown to maturity.

41. The method according to claim 24, wherein the transgenic plant or a transgenic plant grown from the transgenic plant seed is grown to at least 4 months.

42. The method according to claim 24, wherein the beta carotene content of said transgenic plant or transgenic plant grown from the transgenic plant seed is enhanced by at least 1.6 fold.

43. The nucleic acid construct according to claim 1, wherein the nucleic acid molecule (i) comprises the nucleotide sequence of SEQ ID NO:2, (ii) is an antisense form of the nucleotide sequence of SEQ ID NO:2, or (iii) is a combination of (i) and (ii).

44. The method according to claim 24, wherein the nucleic acid molecule (i) comprises the nucleotide sequence of SEQ ID NO:2, (ii) is an antisense form of the nucleotide sequence of SEQ ID NO:2, or (iii) is a combination of (i) and (ii).

45. A nucleic acid construct comprising:
   (a) a nucleic acid molecule configured to silence β-carotene hydroxylase expression, wherein the nucleic acid molecule
      (i) comprises the nucleotide sequence of SEQ ID NO: 2,
      (ii) is an antisense form of the nucleotide sequence of SEQ ID NO: 2, or
      (iii) is a combination of (i) and (ii), and
      wherein either (i), (ii), or (iii) is positioned in the nucleic acid construct to result in suppression or interference with endogenous mRNA encoding β-carotene hydroxylase;
   (b) a 5' DNA heterologous promoter sequence, wherein the DNA promoter is a tissue-specific promoter or an organ-specific promoter; and
   (c) a 3' terminator sequence,
      wherein the nucleic acid molecule, the promoter, and the terminator are operatively coupled to permit transcription of the nucleic acid molecule.

* * * * *

SEQUENCE LISTING

```
<160> NUMBER OF SEQ ID NOS: 52

<210> SEQ ID NO 1
<211> LENGTH: 309
<212> TYPE: PRT
<213> ORGANISM: Solanum tuberosum

<400> SEQUENCE: 1

Met Ala Ala Ala Ala Arg Ile Ser Ala Ser Ser Thr Ser Gly Thr Ile
1               5                   10                  15

Tyr Phe Arg His Thr Pro Phe Leu Gly Pro Lys Pro Thr Ser Thr Thr
            20                  25                  30

Ser His Val Ser Pro Ile Ser Pro Phe Ser Pro Asn Leu Gly Pro Ile
        35                  40                  45

Leu Arg Ser Arg Arg Lys Pro Ser Phe Thr Val Cys Phe Val Leu Glu
    50                  55                  60

Asp Glu Lys Leu Lys Pro Gln Phe Glu Asp Glu Ala Glu Asp Phe Glu
65                  70                  75                  80

Lys Lys Ile Glu Glu Gln Ile Ser Ala Thr Arg Leu Ala Glu Lys Leu
                85                  90                  95

Ala Arg Lys Lys Ser Glu Arg Phe Thr Tyr Leu Val Ala Ala Val Met
            100                 105                 110

Ser Ser Phe Gly Ile Thr Ser Met Ala Val Met Ala Val Tyr Tyr Arg
        115                 120                 125

Phe Ser Trp Gln Met Glu Gly Gly Glu Val Pro Leu Thr Glu Met Leu
    130                 135                 140
```

```
Gly Thr Phe Ala Leu Ser Val Gly Ala Ala Val Gly Met Glu Phe Trp
145                 150                 155                 160

Ala Arg Trp Ala His Lys Ala Leu Trp His Ala Ser Leu Trp His Met
                165                 170                 175

His Glu Ser His His Lys Pro Arg Glu Gly Pro Phe Glu Leu Asn Asp
            180                 185                 190

Val Phe Ala Ile Thr Asn Ala Val Pro Ala Ile Ala Leu Leu Asn Tyr
        195                 200                 205

Gly Phe Phe His Lys Gly Leu Ile Pro Gly Leu Cys Phe Gly Ala Gly
    210                 215                 220

Leu Gly Ile Thr Val Phe Gly Met Ala Tyr Met Phe Val His Asp Gly
225                 230                 235                 240

Leu Val His Lys Arg Phe Pro Val Gly Pro Val Ala Asn Val Pro Tyr
                245                 250                 255

Leu Arg Lys Val Ala Ala Ala His Ser Leu His His Ser Glu Lys Phe
            260                 265                 270

Asn Gly Val Pro Tyr Gly Leu Phe Leu Gly Pro Lys Glu Leu Glu Glu
        275                 280                 285

Val Gly Gly Thr Glu Glu Leu Glu Lys Glu Val Asn Arg Arg Thr Arg
    290                 295                 300

Leu Ser Lys Gly Ser
305
```

<210> SEQ ID NO 2
<211> LENGTH: 847
<212> TYPE: DNA
<213> ORGANISM: Solanum tuberosum
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t

<400> SEQUENCE: 2
gggagtnggg gntntggtta ctgaataagt attactcctc gcgcggngcc ggccgctcta      60
gaactagtgg atcccccggg ctgcaggaat tcggcacgag gctaaattgg tcatccccac     120
aatcaatggc tgccgccgcc agaatttccg cctcttctac ttcaggaaca atttttttcc     180
gtcatactcc gtttcttggc ccaaaaccca cttcaacaac ctcacatgtt tctccaatct     240 ctccttttc tcctaatcta ggcccaattc tgaggtctag aagaaaaccc agtttcactg     300
tttgctttgt tctcgaggat gagaagctga aacctcaatt tgaggatgag cagaggatt     360 ttgaaaagaa gattgaggaa cagatctcag ctacacgctt ggtggaaaaa ttggctagga     420
agaaatcgga gaggtttact tatcttgtag ctgctgtaat gtctagtttt gggattactt     480
ctatggctgt tatggcggtt tattacagat tttcgtggca aatggagggt ggagaagttc     540 cctttaaccga aatgttgggt acatttgctc tctctgttgg tgctgctgta ggaatggagt     600
tttgggcaag atgggcacac aaagcattgt ggcatgcttc actatggcac atgcacgagt     660

```
cacatcacaa accaagagaa ggacctttg agctgaatga cgttttcgcc ataacaaacg      720
ctgttccagc aatagccctc ctcaactatg gttttttcca caaaagcctc attccttggg      780
ctatgcttcc gcgcttgggc tagggatcac agtatttgga atggcataca tgttcgttca      840
ccatggg                                                                847
```

<210> SEQ ID NO 3
<211> LENGTH: 925
<212> TYPE: DNA
<213> ORGANISM: Solanum tuberosum
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t

<400> SEQUENCE: 3

```
ggaagagagt tttnaanaat ggataacatg ctggagctcc acctgagtgg cgtccgctct       60
agaactagtg gatccccgg gctgcaggaa ttggcacgag gatttcctta aattgccct       120 caactgccat cactccactc ctctctacca actctgagag agagtctaaa ttggtcatcc      180
ccacaatcaa tggctgccgc cgccagaatt tccgcctctt ctacttcagg aacaattttt      240
ttccgtcata ctccgtttct tggcccaaaa cccacttcaa caacctcaca tgtttctcca      300
atctctcctt tttctcctaa tctaggccca attctgaggt ctagaagaaa acccagtttc      360
actgtttgct ttgttctcga ggatgagaag ctgaaacctc aatttgagga tgaggcagag      420
gattttgaaa agaagattga ggaacagatc tcagctacac gcttggtgga aaaattggct      480
aggaagaaat cggagaggtt tacttatctt gtagctgctg taatgtctag ttttgggatt      540
acttctatgg ctgttatggc ggtttattac agattttcgt ggcaaatgga gggtggagaa      600
gttcctttaa ccgaaatgtt gggtacattt gctctctctg ttggtgctgc tgtangaatg      660
gagttttggg caagatgggc acacaaagca ttgtggcatt gctcactatg gcacatgcac      720
gagtcacatc acaaaccaag agaaggacct tttgagctgg atgacgtttt cgccataaca      780
aacgcttgtc caacaatagc ccctcccaac tatggttttt cccaaagggc cattccctgg      840
ctttgcttcg gcgctgggct aggatacacag atttgaatgg ctccatgtcg ttcacgaagg      900
tggttcccaa aaaattccgt tgacc                                           925
```

<210> SEQ ID NO 4
<211> LENGTH: 310
<212> TYPE: PRT
<213> ORGANISM: Arabidopsis thaliana

<400> SEQUENCE: 4

```
Met Ala Ala Gly Leu Ser Thr Ala Val Thr Phe Lys Pro Leu His Arg
1               5                   10                  15

Ser Phe Ser Ser Ser Ser Thr Asp Phe Arg Leu Arg Leu Pro Lys Ser
            20                  25                  30

Leu Ser Gly Phe Ser Pro Ser Leu Arg Phe Lys Arg Phe Ser Val Cys
        35                  40                  45

Tyr Val Val Glu Glu Arg Arg Gln Asn Ser Pro Ile Glu Asn Asp Glu
```

```
                 50                  55                  60
Arg Pro Glu Ser Thr Ser Thr Asn Ala Ile Asp Ala Glu Tyr Leu
 65                  70                  75                  80

Ala Leu Arg Leu Ala Glu Lys Leu Glu Arg Lys Ser Glu Arg Ser
                 85                  90                  95

Thr Tyr Leu Ile Ala Ala Met Leu Ser Ser Phe Gly Ile Thr Ser Met
                100                 105                 110

Ala Val Met Ala Val Tyr Tyr Arg Phe Ser Trp Gln Met Glu Gly Gly
            115                 120                 125

Glu Ile Ser Met Leu Glu Met Phe Gly Thr Phe Ala Leu Ser Val Gly
        130                 135                 140

Ala Ala Val Gly Met Glu Phe Trp Ala Arg Trp Ala His Arg Ala Leu
145                 150                 155                 160

Trp His Ala Ser Leu Trp Asn Met His Glu Ser His His Lys Pro Arg
                165                 170                 175

Glu Gly Pro Phe Glu Leu Asn Asp Val Phe Ala Ile Val Asn Ala Gly
            180                 185                 190

Pro Ala Ile Gly Leu Leu Ser Tyr Gly Phe Phe Asn Lys Gly Leu Val
        195                 200                 205

Pro Gly Leu Cys Phe Gly Ala Gly Leu Gly Ile Thr Val Phe Gly Ile
210                 215                 220

Ala Tyr Met Phe Val His Asp Gly Leu Val His Lys Arg Phe Pro Val
225                 230                 235                 240

Gly Pro Ile Ala Asp Val Pro Tyr Leu Arg Lys Val Ala Ala His
                245                 250                 255

Gln Leu His His Thr Asp Lys Phe Asn Gly Val Pro Tyr Gly Leu Phe
            260                 265                 270

Leu Gly Pro Lys Glu Leu Glu Glu Val Gly Gly Asn Glu Glu Leu Asp
        275                 280                 285

Lys Glu Ile Ser Arg Arg Ile Lys Ser Tyr Lys Lys Ala Ser Gly Ser
290                 295                 300

Gly Ser Ser Ser Ser Ser
305                 310

<210> SEQ ID NO 5
<211> LENGTH: 933
<212> TYPE: DNA
<213> ORGANISM: Arabidopsis thaliana

<400> SEQUENCE: 5
atggcggcag gactctcaac cgccgttaca ttcaaaccac tccaccgctc tttctcctcc     60
tcctctaccg atttccgact ccgcctcccg aaatccttat ccggattctc tccgtctctt    120
cgatttaaac gcttttctgt ctgttacgtc gtcgaagaac ggagacagaa ttctccgatt    180
gagaacgatg agagaccgga gagcacgagc tccacaaacg ctatagacgc tgagtatctg    240
gcgttgcgtt tggcggagaa attggagagg aagaaatcgg agaggtccac ttatctaatc    300
gctgctatgt tgtcgagctt tggtatcact tctatggctg ttatggctgt ttactacaga    360
ttctcttggc aaatggaggg aggtgagatc tcaatgttgg aaatgtttgg tacatttgct    420
ctctctgttg gtgctgctgt tggtatggaa ttctgggcaa gatgggctca tagagctctg    480
tggcacgctt ctctatggaa tatgcatgag tcacatcaca aaccaagaga aggaccgttt    540
gagctaaacg atgtttttgc tatagtgaac gctggtccag cgattggtct cctctcttat    600
ggattcttca ataaaggact cgttcctggt ctctgctttg gcgccgggtt aggcataacg    660
```

```
gtgtttggaa tcgcctacat gtttgtccac gatggtctcg tgcacaagcg tttccctgta    720
ggtcccatcg ccgacgtccc ttacctccga aggtcgccg ccgctcacca gctacatcac      780
acagacaagt tcaatggtgt accatatgga ctgtttcttg acccaagga attggaagaa      840 gttggaggaa atgaagagtt agataaggag attagtcgga gaatcaaatc atacaaaaag    900
gcctcgggct ccgggtcgag ttcgagttct tga                                 933

<210> SEQ ID NO 6
<211> LENGTH: 323
<212> TYPE: PRT
<213> ORGANISM: Barley

<400> SEQUENCE: 6
```

Arg His Glu Ala Leu Gly Leu His His Gly Gln Leu Arg Arg Gln Glu
1               5                   10                  15

Pro Ser Pro Arg Arg Ala Val Pro Asp Ala Ala Phe Pro Cys Arg
            20                  25                  30

Pro Ala Ser Pro Val Leu Pro Val His Ala Asp Gly Ala Gln Glu Gly
        35                  40                  45

Ala Arg Asp Arg Asp Val Leu Arg Pro Ala Gly Ala Gly Ala Gly
50                  55                  60

Pro Gly Ser Arg Ala Gly Ala Gly Asp Gly Ala Gly Ala Phe Ala Gly
65                  70                  75                  80

Gly Arg Gly Gly Val Arg Gly Gly Ala Ala Arg Gly Gly Glu Glu Gly
                85                  90                  95

Ala Glu Ala Val Arg Glu Ala Asp Val Pro Gly Gly Arg Arg His Val
            100                 105                 110

Gln Pro Arg Gly His Leu His Gly His Arg Leu Arg Val Leu Pro Leu
        115                 120                 125

Arg Leu Ala Asn Gly Gly Arg Arg Gly Ala Asp Asp Arg Asp Ala Gly
130                 135                 140

His Val Arg Ala Leu Arg Arg Gly Gly Arg Asp Gly Val Leu Gly
145                 150                 155                 160

Ala Val Gly Ala Gln Gly Ala Val Ala Arg Val Pro Val Ala His Ala
                165                 170                 175

Arg Val Ala Pro Pro Ala Ala Arg Arg Ala Leu Arg Ala Gln Arg Arg
            180                 185                 190

Leu Arg His His Gln Arg Arg Ala Gly His Arg Pro Arg Leu Arg
        195                 200                 205

Leu Leu Pro Pro Arg Pro Arg Pro Leu Leu Arg Gly Pro
        210                 215                 220

Trp Asp Tyr Ala Phe Arg Asp Gly Ile His Val Arg Pro Arg Pro
225                 230                 235                 240

Gly Pro Pro Leu Pro Arg Pro His Arg Arg Ala Leu Leu
                245                 250                 255

Pro Ala Ser Gly Cys Arg Ser Gln Asp Thr Pro His Gly Gln Val Arg
            260                 265                 270

Gly Arg Thr Val Trp Ala Leu Pro Gly Thr Gln Gly Ala Gly Arg
        275                 280                 285

Trp Trp Pro Arg Arg Ala Gly Ala Gly Ala Arg Gln Asn Gln Pro Asp
        290                 295                 300

Ser Glu His Leu Ser Ser Gly His Gly Val Ala Ala Tyr Ala Ala Arg
305                 310                 315                 320

Arg Thr Leu

<210> SEQ ID NO 7
<211> LENGTH: 971
<212> TYPE: DNA
<213> ORGANISM: Barley

<400> SEQUENCE: 7

```
cggcacgagg ctctcgggct ccaccatggc cagcttcgcc gtcaagaacc ctctcctcgc    60
cgccgcgcgg taccggacgc tgccttcccg tgccggccgg cctctcccgt tctccccgtt   120
cacgcggacg gcgcgcagga gggggcaaga gaccgtgacg tgcttcgtcc cgcaggaggg   180
gcaggcgccg ggcccggctc ccgtgccgga gccggcgacg gtgccggtgc cttcgctgga   240
ggaagaggcg gcgtccgcgg cggcgcggcg cgtggcggag aggaaggcgc ggaagcagtc   300
cgagaggcgg acgtacctgg tggccgccgt catgtccagc ctaggggtca cctccatggc   360
catcgcctcc gtgtactacc gcttcgcctg gcaaatggag gcggcgagg  tgccgatgac   420
cgagatgctg ggcacgttcg cgctctccgt cggcgcggcg gtcgggatgg agttctgggc   480
gcagtgggcg cacaaggcgc tgtggcacgc gtccctgtgg cacatgcacg agtcgcacca   540
ccggccgcgc gacgggccct tcgagctcaa cgacgtcttc gccatcatca acgccgtgcc   600
ggccatcgcc ctcctcgcct acggcttctt ccaccgcggc ctcgtccccg gcctctgctt   660
cggcgcgggc cttgggatta cgcttttcgg gatggcatac atgttcgtcc acgacggcct   720
ggtccaccgc cgcttccccg tcggccccat cgccgacgtg ccctacttcc ggcgagtggc   780
tgccgctcac aagatacacc acatggacaa gttcgagggc gtaccgtatg gctctcttcct   840
gggacccaag gagctggagg acgttggtgg cctcgacgag ctggagcagg agctcgccag   900
aatcaaccgg actcggagca tctgagctct ggacatggcg tggcggcata tgcagctaga   960
agaaccttgt g                                                        971
```

<210> SEQ ID NO 8
<211> LENGTH: 300
<212> TYPE: PRT
<213> ORGANISM: Brassica campestris

<400> SEQUENCE: 8

```
Met Ala Ala Gly Leu Ser Thr Thr Val Thr Phe Asn Pro Leu His Arg
  1               5                  10                  15

Ser Phe Ser Ser Ser Ser Val Arg Leu His His Pro Arg Ser Leu
                 20                  25                  30

Thr Gly Leu Pro Ser Ser Leu Arg Phe Arg Gly Phe Ser Val Cys Tyr
             35                  40                  45

Val Val Glu Glu Gln Arg Gln Ser Ser Pro Val Asp Asn Asp Glu Arg
 50                  55                  60

Pro Glu Arg Thr Asn Val Ile Asp Pro Glu Leu Leu Ala Leu Arg Leu
 65                  70                  75                  80

Ala Glu Lys Leu Glu Arg Lys Lys Ser Glu Arg Phe Thr Tyr Leu Ile
                 85                  90                  95

Ala Ala Val Met Ser Ser Phe Gly Ile Thr Ser Met Ala Val Met Ala
            100                 105                 110

Val Tyr Tyr Arg Phe Ser Trp Gln Met Glu Gly Gly Val Ile Pro Met
            115                 120                 125

Ser Glu Met Phe Gly Thr Phe Ala Leu Ser Val Gly Ala Ala Val Gly
        130                 135                 140
```

Met Glu Phe Trp Ala Arg Trp Ala His Arg Ala Leu Trp His Ala Ser
145                 150                 155                 160

Leu Trp Asn Met His Glu Ser His His Lys Pro Arg Glu Gly Pro Phe
                165                 170                 175

Glu Leu Asn Asp Val Phe Ala Ile Ile Asn Ala Val Pro Ala Ile Gly
            180                 185                 190

Leu Leu Ser Tyr Gly Phe Phe Asn Lys Gly Leu Val Pro Gly Leu Cys
        195                 200                 205

Phe Gly Ala Gly Leu Gly Ile Thr Val Phe Gly Ile Ala Tyr Met Phe
    210                 215                 220

Val His Asp Gly Leu Val His Lys Arg Phe Pro Val Gly Pro Ile Ala
225                 230                 235                 240

Asp Val Pro Tyr Leu Arg Lys Val Ala Ala His Gln Leu His His
                245                 250                 255

Thr Asp Lys Phe Asp Gly Val Pro Tyr Gly Leu Phe Leu Gly Pro Lys
            260                 265                 270

Glu Leu Glu Glu Val Gly Gly Asp Glu Leu Asp Lys Glu Ile Ser
        275                 280                 285

Arg Arg Ile Lys Leu Tyr Lys Lys Ser Ser Ser Ser
    290                 295                 300

<210> SEQ ID NO 9
<211> LENGTH: 900
<212> TYPE: DNA
<213> ORGANISM: Brassica campestris

<400> SEQUENCE: 9
atggcggcag gtctctcaac caccgtaaca ttcaaccctc tccaccgctc tttctcatcc      60
tcctcaagtg tccgcttaca ccacccaaga tccttaaccg gactcccttc atctctccgg     120
ttcagaggct tctcggtctg ctacgtcgtc gaggagcaga ggcagagctc tcccgtcgac     180
aacgatgaaa gacctgagag aaccaacgtc atagatcccg agctcttggc tttgcgtttg     240
gctgagaagt tggagaggaa gaagtccgag aggttcactt atctaatagc agctgtgatg     300
tcgagctttg gtatcacttc catggccgtt atggccgttt actacagatt ctcttggcaa     360
atggagggag gtgtgatccc aatgtcagag atgttcggta catttgctct ctctgttggt     420
gctgctgtgg gcatggagtt tgggcaaga tgggctcata gagctctctg gcacgcttct     480
ctttggaata tgcatgagtc acatcacaaa ccaagagaag gtccctttga gctgaacgat     540
gtgtttgcaa ttataaacgc tgttcctgcg attggtctcc tttcttatgg tttcttcaat     600
aaaggactcg tccctggtct tgctttggc gccggactag aataacggt gtttgggatc     660 gcctatatgt ttgtccacga tggtttggtg cacaagcgtt ccctgtagg tcccatcgct     720 gatgtccctt atctccggaa ggtcgctgcc gctcaccagc tacatcacac tgacaagttc     780
gatggtgtgc catatggact gttcttggga ccaaaggaat tggaagaagt tggaggagat     840
gaagagttag acaaggagat tagtcggaga atcaaattat acaaaaagag ttcgagctct     900

<210> SEQ ID NO 10
<211> LENGTH: 311
<212> TYPE: PRT
<213> ORGANISM: Citrus

<400> SEQUENCE: 10

Met Ala Val Gly Leu Leu Ala Ala Ile Val Pro Lys Pro Phe Cys Leu
1                   5                   10                  15

```
Leu Thr Thr Lys Leu Gln Pro Ser Ser Leu Thr Thr Lys Pro Ala
             20                  25                  30

Pro Leu Phe Ala Pro Leu Gly Thr His His Gly Phe Phe Asn Gly Lys
         35                  40                  45

Asn Arg Arg Lys Leu Asn Ser Phe Thr Val Cys Phe Val Leu Glu Glu
     50                  55                  60

Lys Lys Gln Ser Thr Gln Ile Glu Thr Phe Thr Asp Glu Glu Glu
 65              70                  75                  80

Glu Ser Gly Thr Gln Ile Ser Thr Ala Ala Arg Val Ala Glu Lys Leu
             85                  90                  95

Ala Arg Lys Arg Ser Glu Arg Phe Thr Tyr Leu Val Ala Ala Val Met
        100                 105                 110

Ser Ser Phe Gly Ile Thr Ser Met Ala Val Met Ala Val Tyr Tyr Arg
        115                 120                 125

Phe Trp Trp Gln Met Glu Gly Gly Glu Val Pro Leu Ala Glu Met Phe
130                 135                 140

Gly Thr Phe Ala Leu Ser Val Gly Ala Ala Val Gly Met Glu Phe Trp
145                 150                 155                 160

Ala Arg Trp Ala His Lys Ala Leu Trp His Ala Ser Leu Trp His Met
                165                 170                 175

His Glu Ser His His Arg Pro Arg Glu Gly Pro Phe Glu Leu Asn Asp
            180                 185                 190

Val Phe Ala Ile Ile Asn Ala Val Pro Ala Ile Ala Leu Leu Ser Phe
        195                 200                 205

Gly Phe Phe His Lys Gly Leu Val Pro Gly Leu Cys Phe Gly Ala Gly
210                 215                 220

Leu Gly Ile Thr Val Phe Gly Met Ala Tyr Met Phe Val His Asp Gly
225                 230                 235                 240

Leu Val His Lys Arg Phe Pro Val Gly Pro Ile Ala Asp Val Pro Tyr
                245                 250                 255

Phe Arg Arg Val Ala Ala Ala His Gln Leu His Ser Asp Lys Phe
        260                 265                 270

His Gly Val Pro Tyr Gly Leu Phe Leu Gly Pro Lys Glu Leu Glu Glu
            275                 280                 285

Val Gly Gly Leu Glu Glu Leu Glu Lys Glu Ile Ser Lys Arg Ile Lys
290                 295                 300

Ser Tyr Asn Arg Val Pro Lys
305                 310

<210> SEQ ID NO 11
<211> LENGTH: 912
<212> TYPE: DNA
<213> ORGANISM: Citrus

<400> SEQUENCE: 11
atggcggtcg gactattggc cgccatagtc ccgaagccct tctgtctcct cacaacaaaa    60
cttcaaccct cttcgctcct cacaacaaaa cctgctcccc ttttgccccc cgccacggct   120
tctttaatgg caaaaaccga agaaaaatca actctttcac cgtatgtttt gttttagagg   180
agaaaaaaca aagcacccag atcgagactt tcacggagga ggaggaggag gagtcgggta   240
cccagatctc gactgctgcc gcgtggccg agaaattggc gagaaagaga tccgagaggt   300
tcacttatct cgttgctgcc gtcatgtcta gttttggtat cacttccatg gctgtcatgg   360
ctgtttatta caggttctgg tggcaaatgg agggtggaga gctgaaatgt ttggcacatt   420
```

```
tgctctctct gttggtgctg ctgtgggcat ggagttttgg gcacgatggg ctcataaagc    480
tctgtggcat gcttctttat ggcatatgca cgagtctcac catcgaccaa gagagggtcc    540
ttttgagcta aacgatgtgt tgccataat caacgcagtt ccagccatag cccttctctc     600
ttttggcttc ttccacaaag gcctgtacc tggtctctgt tttggtgctg gacttggcat     660
tacggtgttt gggatggcct acatgttcgt ccacgatggt ctcgttcaca aaggttccc    720 tgtgggtccc attgccgacg tgccttattt ccggagagtc gctgcggctc caagcttca    780 ccactcggat aaattccacg gtgttccata tgggctcttt ctcggaccta aggagcttga    840
agaagtgggg ggactagaag aattggagag gagatcagta agagaatcaa atcatacaac    900
agggttccaa aa                                                        912
```

<210> SEQ ID NO 12
<211> LENGTH: 300
<212> TYPE: PRT
<213> ORGANISM: Cotton

<400> SEQUENCE: 12

```
Met Ala Val Gly Leu Ser Ala Ala Val Thr Pro Lys Pro Phe Arg Ser
1               5                   10                  15

Phe Pro Leu Leu Lys Pro Ala Pro Ile Phe His Pro Leu Leu His Leu
                20                  25                  30

Pro Lys Thr Thr Thr Tyr Ala Ala Arg Arg Lys Lys Ser Phe Ala Val
            35                  40                  45

Cys Phe Val Val Asp Glu Glu Gln Lys Gln Ser Ala Pro Thr Gln Ile
        50                  55                  60

Val Glu Gln Gly Phe Glu Asp Ala Arg Asp Arg Gln Ile Leu Ile Pro
65                  70                  75                  80

Ser Arg Leu Ser Glu Lys Leu Ala Arg Lys Arg Ser Glu Arg Phe Thr
                85                  90                  95

Tyr Leu Val Ala Ala Val Met Ser Ser Phe Gly Ile Thr Ser Met Ser
                100                 105                 110

Val Met Ala Val Tyr Tyr Arg Phe Trp Trp Gln Met Glu Gly Gly Glu
            115                 120                 125

Val Pro Leu Ser Glu Met Phe Gly Thr Phe Thr Leu Ala Val Gly Ala
        130                 135                 140

Ala Val Gly Met Glu Phe Trp Ala Arg Trp Ala His Arg Ala Leu Trp
145                 150                 155                 160

His Ala Ser Leu Trp His Met His Glu Ser His His Arg Pro Arg Glu
                165                 170                 175

Gly Pro Phe Glu Leu Asn Asp Val Phe Ala Ile Thr Asn Ala Val Pro
            180                 185                 190

Ala Ile Ala Leu Leu Ser Tyr Gly Phe Phe Asn Lys Gly Leu Val Pro
        195                 200                 205

Gly Leu Cys Phe Gly Ala Gly Leu Gly Ile Thr Met Phe Gly Met Ala
    210                 215                 220

Tyr Met Phe Val His Asp Gly Leu Val His Lys Arg Phe Pro Val Gly
225                 230                 235                 240

Pro Ile Ala Asn Val Pro Tyr Phe Arg Lys Val Ala Ala His Gln
                245                 250                 255

Leu His His Ser Glu Lys Phe Asn Gly Val Pro Tyr Gly Leu Phe Leu
            260                 265                 270

Gly Pro Lys Glu Val Glu Asp Val Gly Gly His Glu Glu Leu Glu Lys
        275                 280                 285
```

```
Glu Ile Asn Arg Arg Ile Lys Ser Ser Lys Gly Ser
    290                 295                 300
```

```
<210> SEQ ID NO 13
<211> LENGTH: 900
<212> TYPE: DNA
<213> ORGANISM: Cotton

<400> SEQUENCE: 13
atggcggttg gcttatccgc cgccgtaact cctaaaccct tccgctcatt tccgctgctg      60
aagcctgcgc caattttcca tcctttactg cacctcccaa aaacaacaac ctacgcagct     120
cgaagaaaga aaagctttgc tgtttgtttc gtggtggatg aagaacagaa gcagagcgct     180
cctacccaga tcgtggaaca aggattcgag gatgctagag atcgtcagat cttaataccg     240
tcgcgtctgt cggagaaatt agctagaaag agatccgaaa ggtttactta cctcgttgcc     300
gctgtcatgt ctagctttgg gattacatcc atgtctgtta tggccgttta ttacaggttt     360
tggtggcaaa tggaggagg agaggtgcct ctttctgaaa tgttcggcac atttactta      420 gcagtcggtg ccgctgtggg catggagttt tgggctagat gggctcacag agctctctgg     480
cacgcatcgt tatggcatat gcacgagtca caccatcgac ccagagaagg accgttcgag     540
ctaaacgatg tgttcgccat aaccaacgcc gtcccagcaa ttgctcttct ctcgtatggt     600
ttcttcaaca aaggccttgt acctggtcta tgtttcggtg ctgggcttgg tataacgatg     660
tttggaatgg cttatatgtt cgtccacgat ggtctcgtcc ataagagatt ccccgtaggc     720
cctatcgcca acgtgcctta cttcaggaag gttgctgcgg ctcaccagct ccatcattca     780
gaaaaattca atggtgttcc atatgggctg tttctagggc cgaaggaagt ggaggatgtg     840
ggaggacatg aagaattgga gaaagaaatc aacaggagaa tcaaatcaag caaaggttcc     900

<210> SEQ ID NO 14
<211> LENGTH: 305
<212> TYPE: PRT
<213> ORGANISM: Crocus

<400> SEQUENCE: 14

Met Ser Ala Lys Ile Ser Pro Ser Ala Thr Thr Leu Ala Ala Ser Phe
1               5                   10                  15

Arg Arg Pro Pro Ser Gly Ala Arg Ile Ile Leu Leu Ser Ser Leu Pro
            20                  25                  30

Val Arg Arg Pro Val Glu Arg Ile Arg Pro Pro Leu Leu His Arg
        35                  40                  45

Arg Arg Arg Thr Ala Thr Val Phe Phe Val Leu Ala Glu Glu Lys Thr
    50                  55                  60

Thr Pro Phe Leu Asp Asp Val Glu Glu Glu Lys Ser Ile Ala Pro Ser
65                  70                  75                  80

Asn Arg Ala Ala Glu Arg Ser Ala Arg Lys Arg Ser Glu Arg Thr Thr
                85                  90                  95

Tyr Leu Ile Thr Ala Val Met Ser Ser Phe Gly Ile Thr Ser Met Ala
            100                 105                 110

Ala Ala Ala Val Tyr Tyr Arg Phe Ala Trp Gln Met Glu Gly Gly Asp
        115                 120                 125

Val Pro Val Thr Glu Met Ala Gly Thr Phe Ala Leu Ser Val Gly Ala
    130                 135                 140

Ala Val Gly Met Glu Phe Trp Ala Arg Trp Ala His Arg Ala Leu Trp
145                 150                 155                 160
```

```
His Ala Ser Leu Trp His Met His Glu Ser His His Arg Pro Arg Glu
                165                 170                 175

Gly Pro Phe Glu Leu Asn Asp Val Phe Ala Ile Ile Asn Ala Val Pro
            180                 185                 190

Ala Ile Ala Leu Leu Asn Phe Gly Phe His Arg Gly Leu Leu Pro
        195                 200                 205

Gly Leu Cys Phe Gly Ala Gly Leu Gly Ile Thr Leu Phe Gly Ile Ala
    210                 215                 220

Tyr Met Phe Val His Asp Gly Leu Val His Arg Arg Phe Pro Val Gly
225                 230                 235                 240

Pro Ile Ala Asp Val Pro Tyr Phe Gln Arg Val Ala Ala Ala His Gln
            245                 250                 255

Ile His His Ser Glu Lys Phe Glu Gly Val Pro Tyr Gly Leu Phe Met
        260                 265                 270

Gly Pro Lys Glu Leu Glu Glu Ile Gly Gly Leu Lys Glu Leu Glu Lys
    275                 280                 285

Glu Val Ser Arg Arg Ile Lys Ala Tyr Asn Asn Ser Ala Glu Ile Lys
290                 295                 300

Thr
305

<210> SEQ ID NO 15
<211> LENGTH: 915
<212> TYPE: DNA
<213> ORGANISM: Crocus

<400> SEQUENCE: 15
atgtcggcca aaatctcccc ctccgccacc accctcgccg cctccttccg ccgccctccg      60
tccggcgcac gcatcatcct cctctcttcg ctccctgtcc gccgcccgt cgaacgtcga     120 atccggccgc cgttgcttca tcgtcggcgt cggacggcga cagtgttttt cgttctcgcc     180
gaagaaaaaa caactccttt tcttgacgat gtggaggaag agaagagtat tgcgccgtca     240
aatcgggcgg ctgagaggtc ggcgcggaag cggtcggagc ggaccacgta cctcatcacg     300
gcggttatgt cgagcttcgg catcacatcc atggccgccg ccgccgtcta ctaccgcttc     360
gcttggcaaa tggagggagg ggatgtgcca gtgacggaga tggcgggaac gttcgctctc     420
tcggtcgggg cggccgtggg gatggagttc tgggccaggt gggcccaccg ggcactctgg     480
cacgcgtcgc tctggcacat gcacgagtcc caccaccggc cgagggaggg ccctttcgag     540
ctcaacgacg tcttcgccat aatcaacgcg gtccccgcca tcgccctcct caacttcggc     600
ttcttccaca gaggtctcct ccccggcctc tgtttcggcg ccgggctggg gatcacgctg     660
tttggtattg cgtacatgtt cgtccacgac gggctagtcc accggcggtt ccctgtgggg     720
cccatcgccg acgtgcccta cttccagcgc gtcgccgctg ctcaccagat ccaccactcg     780
gagaagttcg aagggggtgcc ctatggactg ttcatggggc caaggaatt ggaggagatt     840 ggtggattaa aagagctgga gaaggaggtg agcaggagga ttaaggcata taataacagc     900
gccgaaatca aaacc                                                     915

<210> SEQ ID NO 16
<211> LENGTH: 308
<212> TYPE: PRT
<213> ORGANISM: Daffodil

<400> SEQUENCE: 16
```

```
Met Ala Val Trp Ile Ser Ala Pro Pro Ala Leu Ala Ile Ser Ser
 1               5                  10                  15

Ala Pro Arg Ile Arg Val Ile Leu Phe Ser Pro Leu His Ser Arg
            20                  25                  30

Gln Ile Gly Trp Pro Pro Ile Arg Asn Arg Arg Lys Arg Ser Lys Ser
            35                  40                  45

Thr Val Phe Phe Ala Ser Asp Val Asp Val Gly Lys Ser Asn Gly Gly
 50                  55                  60

Asp Gly Ile Val Asp Lys Ile Glu Arg Leu Lys Gln Glu Gln Leu
 65                  70                  75                  80

Met Ile Ser Lys Ser Arg Thr Thr Glu Arg Met Glu Arg Lys Arg Ser
                85                  90                  95

Glu Arg Thr Thr Tyr Leu Ile Ala Ala Met Met Ser Ser Leu Gly Ile
            100                 105                 110

Thr Ser Met Ala Ile Val Ser Val Tyr Tyr Arg Phe Ala Trp Gln Met
                115                 120                 125

Glu Glu Gly Glu Ile Pro Val Thr Glu Met Leu Gly Thr Phe Ala Leu
            130                 135                 140

Ser Val Gly Ala Ala Val Gly Met Glu Phe Trp Ala Arg Trp Ala His
145                 150                 155                 160

Arg Ala Leu Trp His Ala Ser Leu Trp His Met His Glu Ser His His
                165                 170                 175

Lys Pro Arg Asp Gly Pro Phe Glu Leu Asn Asp Val Phe Ala Val Ile
            180                 185                 190

Asn Ala Val Pro Ala Ile Ser Leu Leu Tyr Tyr Gly Phe Phe Asn Arg
            195                 200                 205

Gly Leu Val Pro Gly Leu Cys Phe Gly Ala Gly Leu Gly Ile Thr Leu
            210                 215                 220

Tyr Gly Met Ala Tyr Met Phe Val His Asp Gly Leu Val His Arg Arg
225                 230                 235                 240

Phe Pro Val Gly Pro Ile Ala Asp Val Pro Tyr Phe Arg Arg Val Ala
                245                 250                 255

Ala Ala His Arg Ile His His Thr Glu Lys Phe Asn Gly Val Pro Tyr
            260                 265                 270

Gly Leu Phe Leu Gly Pro Lys Glu Leu Glu Glu Val Gly Gly Glu Glu
            275                 280                 285

Glu Leu Glu Lys Leu Ile Lys Arg Arg Ile Glu Ile Asn Ser Arg Ser
            290                 295                 300

Leu Asp Val Lys
305

<210> SEQ ID NO 17
<211> LENGTH: 923
<212> TYPE: DNA
<213> ORGANISM: Daffodil

<400> SEQUENCE: 17
atggcagttt ggatctccgc cgctcccccg ccctcgcga tctcctccgc ccccgcatc      60 cgccgtgtca tcctcttctc cccgctccac agccgtcaga tcggatggcc gccgatcagg     120
aaccgtcgaa agaggagcaa gtcgacggtg tttttcgcct cggacgtgga cgtcggtaag    180
tccaacggcg gcgatgggat cgtcgataaa attgagcgac tgaagaaaca ggagcagctg    240
atgatctcga aatcgcgcac gacggagaga atggagagga gcgatcgga gaggacgacg    300 tatctgatcg cggcgatgat gtcgagcttg gggatcacgt caatggcgat cgtctccgtt    360
```

```
tattaccgat tgcttggca aatggaggaa ggggagattc ccgtaacgga aatgctggga    420
acgttcgcgt tgtcagtggg ggccgcagtt gggatggaat tttgggcgag atgggcgcat    480
cgagctctat ggcatgcatc cttgtggcac atgcatgagt cgcatcacaa accacgtgac    540
ggtccatttg agctcaacga tgttttcgcc gtcattaacg ccgttccggc gatctctctt    600
ctatactacg gcttcttcaa ccgcggacta gttcccggcc tctgctttgg tgccggtctt    660
ggaatcacac tctacgggat ggcgtacatg ttcgttcacg acggattggt tcaccggcga    720
ttcccagtgg gacccattgc cgatgttccc tatttcagaa gagttgccgc tgctcatcgg    780
atccaccata ctgagaagtt caacggggtg ccctatgggc tgttcttggg tcccaaggaa    840
ttggaggagg tgggcggtga agaggagctg agaaaattga ttaagaggag gattgagatt    900
aacagccgca gcttagatgt taa    923
```

<210> SEQ ID NO 18
<211> LENGTH: 299
<212> TYPE: PRT
<213> ORGANISM: Grape

<400> SEQUENCE: 18

```
Met Ala Thr Gly Ile Ser Ala Ser Leu Asn Ser Met Ser Cys Arg Leu
1               5                   10                  15

Gly Arg Asn Ser Phe Thr Ala Thr Gly Pro Ser Ser Val Ile Ser Leu
            20                  25                  30

Ser Ser Phe Leu Thr Pro Val Thr His Leu Lys Gly Asn Ile Phe Pro
        35                  40                  45

Leu Gln Arg Arg Ser Leu Lys Val Cys Leu Val Leu Glu Lys Glu
    50                  55                  60

Ile Glu Asp Gly Ile Glu Ile Glu Asp Asp Ser Pro Glu Ser Ser Asn
65                  70                  75                  80

Arg Ala Ser Glu Arg Leu Ala Arg Lys Lys Ala Glu Arg Tyr Thr Tyr
                85                  90                  95

Leu Val Ala Ala Met Met Ser Ser Leu Gly Ile Thr Ser Met Ala Ile
            100                 105                 110

Val Ala Val Tyr Tyr Arg Leu Ser Trp Gln Met Glu Gly Gly Glu Ile
        115                 120                 125

Pro Val Leu Glu Met Leu Gly Thr Phe Ala Leu Ser Val Gly Ala Ala
    130                 135                 140

Val Gly Met Glu Phe Trp Ala Arg Trp Ala His Lys Ala Leu Trp His
145                 150                 155                 160

Ala Ser Leu Trp His Met His Glu Ser His His Arg Pro Arg Glu Gly
                165                 170                 175

Pro Phe Glu Leu Asn Asp Val Phe Ala Ile Ile Asn Ala Val Pro Ala
            180                 185                 190

Ile Ser Leu Leu Ser Tyr Gly Leu Phe Asn Lys Gly Leu Val Pro Gly
        195                 200                 205

Leu Cys Phe Gly Ala Gly Leu Gly Ile Thr Val Phe Gly Met Ala Tyr
    210                 215                 220

Met Phe Val His Asp Gly Leu Val His Arg Arg Phe Pro Val Gly Pro
225                 230                 235                 240

Ile Ala Asn Val Pro Tyr Leu Arg Lys Val Ala Ser Ala His Gln Leu
                245                 250                 255

His His Ser Asp Lys Phe Asn Gly Val Pro Tyr Gly Leu Phe Leu Gly
            260                 265                 270
```

```
Pro Met Glu Leu Glu Glu Val Gly Gly Met Glu Glu Leu Glu Lys Glu
        275                 280                 285

Ile Ser Arg Arg Ile Lys Ser Ser Asp Ser Ser
        290                 295
```

<210> SEQ ID NO 19
<211> LENGTH: 897
<212> TYPE: DNA
<213> ORGANISM: Grape

<400> SEQUENCE: 19

```
atggcgacag gaatttcggc ttctttaaac tccatgtcgt gccgtttggg ccggaatagt      60
ttcacagcca ccggacccag ctcggtgata agtttgtcgt cttcttaac tccggtgacc     120
cacttgaagg ggaatatttt tcctctacag agaaggagga gcttgaaggt gtgcttggtc     180
ctggagaaga aaattgaaga tggtattgaa attgaggacg acagtccgga aagctcgaac     240
agggcctcgg agagactagc gaggaagaaa gcggaaagat acacttatct tgttgctgct     300
atgatgtcta gcctcggcat cacttcaatg ctatcgttg ctgtctacta cagatttcct     360
tggcaaatgg agggtggaga atcccagtt ctggaaatgt tgggtacatt tgctctttct     420
gtgggagctg ctgtggggat ggagttttgg gctcggtggg ctcacaaagc gctctggcat     480
gcttcactgt ggcatatgca cgagtctcac catagaccca gagaaggtcc tttcgagctc     540
aacgatgtgt ttgccatcat caatgccgtc ccggcaatat ctctgctctc ctatggcctc     600
ttcaacaaag gcctcgtccc aggtctctgt ttcggagctg gactaggaat aacagtgttt     660
ggcatggcct acatgtttgt ccacgacggc cttgtccacc gtcgattccc tgtaggaccc     720
atcgccaacg tcccttatct acgaaaagta gcttcggccc accaacttca tcactctgac     780
aaatttaatg gagttccata cgggctgttc ttgggaccca tggagctgga agaggtggga     840
ggcatggaag agttggaaaa ggagatcaat agaagaatta aatcatctga ctcttca      897
```

<210> SEQ ID NO 20
<211> LENGTH: 182
<212> TYPE: PRT
<213> ORGANISM: Maize

<400> SEQUENCE: 20

```
Met Glu Gly Gly Gly Glu Ile Pro Val Thr Glu Met Val Gly Thr Phe
1               5                   10                  15

Ala Leu Ser Val Gly Ala Ala Val Gly Met Glu Phe Trp Ala Arg Trp
            20                  25                  30

Ala His Arg Ala Leu Trp His Ala Ser Leu Trp His Met His Gln Ser
        35                  40                  45

His His Arg Pro Arg Asp Gly Pro Phe Glu Leu Asn Asp Val Phe Ala
    50                  55                  60

Ile Val Asn Ala Val Pro Ala Met Ser Leu Leu Ala Tyr Gly Phe Phe
65                  70                  75                  80

Asn Arg Gly Leu Val Pro Gly Leu Cys Phe Gly Ala Gly Leu Gly Ile
            85                  90                  95

Thr Leu Phe Gly Met Ala Tyr Met Phe Val His Asp Gly Leu Val His
            100                 105                 110

Arg Arg Phe Pro Val Gly Pro Ile Glu Asn Val Pro Tyr Phe Arg Arg
        115                 120                 125

Val Ala Ala Ala His Gln Ile His His Met Asp Lys Phe Gln Gly Val
    130                 135                 140
```

Pro Tyr Gly Leu Phe Leu Gly Pro Lys Glu Leu Lys Glu Val Gly Gly
145                 150                 155                 160

Thr Glu Glu Leu Glu Lys Glu Ile Lys Lys Arg Ile Arg Arg Arg Glu
                165                 170                 175

Ala Leu Asp Ala Ile Gln
            180

<210> SEQ ID NO 21
<211> LENGTH: 548
<212> TYPE: DNA
<213> ORGANISM: Maize

<400> SEQUENCE: 21 atggagggg gcggcgagat cccggtgacg gagatggtcg gcaccttcgc gctctcggtg      60
ggcgccgcgg tggggatgga gttctgggcg cggtgggcgc accgggcgct gtggcacgcg     120
tcgctgtggc acatgcacca gtcccaccac cggccccgcg acgggccctt cgagctcaac     180
gacgtcttcg ccatcgtcaa cgccgtcccg gccatgtccc cctcgcccta cggcttcttc     240
aaccggggcc tcgtgccggg cctctgcttc ggcgcggggc tggggatcac gctgttcggg     300
atggcctaca tgttcgtgca cgacggcctc gtccaccgcc gcttcccgt cgggcccatc      360 gagaacgtgc cctacttccg ccgcgtcgcc gccgcccatc agatacatca catggacaag     420
ttccagggcg tgccctacgg cctgttcctg gggcccaagg agctgaagga ggtgggagga     480
actgaggagc tggagaagga gatcaagaag aggatcagga ggagggaggc cctagacgcc     540
atccaata                                                              548

<210> SEQ ID NO 22
<211> LENGTH: 309
<212> TYPE: PRT
<213> ORGANISM: Marigold

<400> SEQUENCE: 22

Met Ala Ala Ala Ile Ala Val Pro Cys Ser Ser Arg Pro Phe Gly Leu
1               5                  10                  15

Gly Arg Met Arg Leu Leu Gly His Lys Pro Thr Thr Ile Thr Cys His
            20                  25                  30

Phe Pro Phe Ser Phe Ser Ile Lys Ser Phe Thr Pro Ile Val Arg Gly
        35                  40                  45

Arg Arg Cys Thr Val Cys Phe Val Ala Gly Gly Asp Ser Asn Ser Asn
    50                  55                  60

Ser Asn Asn Ser Asp Ser Asn Ser Asn Pro Gly Leu Asp Leu
65                  70                  75                  80

Asn Pro Ala Val Met Asn Arg Asn Arg Leu Val Glu Glu Lys Met Glu
                85                  90                  95

Arg Lys Lys Ser Glu Arg Phe Thr Tyr Leu Val Ala Ala Ile Met Ser
            100                 105                 110

Thr Phe Gly Ile Thr Ser Met Ala Val Met Ala Val Tyr Tyr Arg Phe
        115                 120                 125

Ser Trp Gln Met Glu Gly Gly Glu Ile Pro Tyr Val Glu Met Phe Gly
    130                 135                 140

Thr Phe Ala Leu Ser Val Gly Ala Ala Val Gly Met Glu Tyr Trp Ala
145                 150                 155                 160

Arg Trp Ala His Glu Ala Leu Trp His Ala Ser Leu Trp His Met His
                165                 170                 175

Glu Ser His His Lys Pro Arg Glu Gly Pro Phe Glu Leu Asn Asp Val
              180                 185                 190

Phe Ala Ile Thr Asn Ala Val Pro Ala Ile Ala Leu Leu Ser Tyr Gly
        195                 200                 205

Phe Phe His Lys Gly Ile Ile Pro Gly Leu Cys Phe Gly Ala Gly Leu
    210                 215                 220

Gly Ile Thr Val Phe Gly Met Ala Tyr Met Phe Val His Asp Gly Leu
225                 230                 235                 240

Val His Arg Arg Phe Gln Val Gly Pro Ile Ala Asn Val Pro Tyr Leu
                245                 250                 255

Arg Arg Val Ala Ala Ala His Gln Leu His His Thr Glu Lys Phe Asn
            260                 265                 270

Gly Val Pro Tyr Gly Leu Phe Leu Gly Pro Lys Glu Leu Glu Glu Val
        275                 280                 285

Gly Gly Thr Glu Glu Leu Asp Lys Glu Ile Gln Arg Arg Ile Lys Leu
    290                 295                 300

Tyr Asn Asn Thr Lys
305

<210> SEQ ID NO 23
<211> LENGTH: 927
<212> TYPE: DNA
<213> ORGANISM: Marigold

<400> SEQUENCE: 23

```
atggcggcag caattgctgt cccttgtagc tcaagaccat ttggcttagg tcgaatgcgg      60
ttacttggtc ataaacccac aaccataact tgtcacttcc ccttttcttt ttctatcaaa     120
tcatttaccc caattgttag gggcagaaga tgtactgttt gttttgttgc cggtggcgac     180
agtaatagta acagtaataa taatagtgac agtaatagta ataatccggg tctggattta     240
aacccggcgg ttatgaaccg taaccgtttg gttgaagaaa aaatggagag gaaaaaatcg     300
gaacgattta cttatcttgt tgcagctatt atgtctactt ttggaattac ttcaatggcg     360
gttatggcgg tttattaccg gttttcatgg caaatggagg gtggagaaat tccttatgtg     420
gagatgtttg gtacatttgc tctctccgtt ggtgctgcgg taggaatgga gtattgggca     480
agatgggctc atgaggcact atggcatgct tctttgtggc acatgcatga gtcacaccat     540
aagccacgag aaggtccgtt tgagcttaat gatgtgtttg ctataacaaa tgcggtcccg     600
gccattgcgt tgcttagtta tgggttttc cacaaaggca taattccggg tctttgtttt     660
ggggcgggac tgggaattac ggtgtttgga atggcgtata tgttcgtcca cgacgggcta     720
gttcacagaa gattccaagt gggtccgatt gcgaatgttc cctatcttcg aagggttgca     780
gcggctcatc agctgcatca cacgaaaaaa tttaatggtg ttccttatgg cttgttcttg     840
ggacctaagg agctagaaga agtgggtggt acggaagaat ggacaaggga gattcaagga     900
agaattaaat tgtataataa tactaaa                                         927
```

<210> SEQ ID NO 24
<211> LENGTH: 148
<212> TYPE: PRT
<213> ORGANISM: Medicago truncatula

<400> SEQUENCE: 24

Met Gly Ser Gln Ala Leu Trp His Ala Ser Leu Trp His Met His Glu
1               5                   10                  15

Ser His His Arg Ala Arg Glu Gly Ala Phe Glu Leu Asn Asp Val Phe

```
            20                  25                  30
Ala Ile Ile Asn Ala Val Pro Ala Ile Ala Leu Leu Asn Phe Gly Phe
        35                  40                  45

Phe His Lys Gly Leu Val Pro Gly Leu Cys Phe Gly Ala Gly Leu Gly
    50                  55                  60

Ile Thr Val Phe Gly Met Ala Tyr Met Phe Val His Asp Gly Leu Val
65                  70                  75                  80

His Arg Arg Phe Ser Val Gly Pro Ile Ala Asn Val Pro Tyr Phe Arg
                85                  90                  95

Arg Val Ala Ala Ala His Lys Leu His His Ser Asp Lys Phe Glu Gly
            100                 105                 110

Val Pro Tyr Gly Leu Phe Leu Gly Pro Lys Glu Leu Glu Glu Val Gly
        115                 120                 125

Gly Leu Glu Glu Leu Glu Lys Glu Ile Ser Arg Arg Thr Lys Ser Tyr
    130                 135                 140

Asn Ser Ser Ser
145

<210> SEQ ID NO 25
<211> LENGTH: 461
<212> TYPE: DNA
<213> ORGANISM: Medicago truncatula

<400> SEQUENCE: 25
atggagtttt gggctagatg ggctcacagg ctctttggca tgcttccttg tgcacatgc      60 atgagtccca tcatagagca agagaaggag ctttcgagtt gaatgatgtt tttgcaataa   120
tcaatgctgt tcctgctatc gctctcctta actttggttt cttccacaaa ggattggtcc   180
ctggtctttg ctttggtgcg ggtcttggaa ttacggtatt tgggatggcc tacatgtttg   240
tacatgatgg tttggttcat aggagattct cagtgggacc cattgccaat gtgccctatt   300
tcagaagggt agctgcagcc cacaaacttc accattcaga caaattcgaa ggggtgccat   360
atgggctgtt tttgggacca aggaacttg aggaagtggg agggctagaa gagctagaga   420
aagagataag taggaggaca aaatcataca atagtagttc a                        461

<210> SEQ ID NO 26
<211> LENGTH: 186
<212> TYPE: PRT
<213> ORGANISM: Onion

<400> SEQUENCE: 26

Met Ala Val Gly Ile Ser Ala Arg Pro Arg Pro Thr Leu Asn Leu Val
1               5                   10                  15

Ala Asp Thr Phe Ser Arg Pro Pro Phe Pro Arg Arg Cys Leu Phe Pro
            20                  25                  30

Ser Phe Pro Pro Ser Thr Asn Arg Phe Leu Ser Ser Pro Pro Leu Arg
        35                  40                  45

Ser Arg Gln Lys Arg Ser Ser Arg Thr Val Tyr Leu Val Leu His Glu
    50                  55                  60

Gly Asp Lys Ser Thr Ala Asp Asn Glu Val Glu Ile Glu Lys Asn Leu
65                  70                  75                  80

Glu Glu Ser Arg Val Ser Lys Gln Arg Ala Met Glu Arg Thr Glu Arg
                85                  90                  95

Lys Lys Thr Glu Arg Thr Thr Tyr Leu Val Ala Ala Ile Met Ser Ser
            100                 105                 110
```

```
Phe Gly Ile Thr Ser Met Ala Ile Val Ser Val Tyr Tyr Arg Phe Ala
            115                 120                 125

Trp Gln Phe Glu Gly Gly Glu Ile Pro Leu Thr Glu Met Phe Gly Thr
130                 135                 140

Phe Ala Leu Ser Val Gly Ala Ala Val Gly Met Glu Phe Trp Ala Asp
145                 150                 155                 160

Gly Pro Thr Glu Pro Tyr Gly Thr Pro His Tyr Gly Thr Cys Thr Asn
                165                 170                 175

Leu Ile Thr Ser Gln Glu Glu Gly Pro Phe
            180                 185

<210> SEQ ID NO 27
<211> LENGTH: 560
<212> TYPE: DNA
<213> ORGANISM: Onion

<400> SEQUENCE: 27
atggcggtcg gaatctccgc cagaccccga ccaaccctca acctcgtcgc tgacaccttc      60
tcccgaccgc cattccccccg acgctgctta ttcccatcct ttcctccatc gacgaaccgt     120
ttcttatcct cacctccgct tagatcgagg caaaaacgaa gcagcagaac cgtgtatctc     180
gtcctccacg agggagataa gtctaccgcc gacaacgaag tcgaaatcga agaatcta       240 gaggagagta gggtttctaa caacgtgca atggagagaa ccgaaaggaa gaaaacggaa     300
cggaccactt atttggttgc ggcgattatg tccagcttcg gaattacttc tatggcgatt     360
gtttccgtct attatcgatt cgcttggcaa ttcgagggag gagagattcc attaaccgaa     420
atgtttggga catttgcatt atcagttggc gccgctgtag gaatggagtt ttgggcagat     480
gggcccacag agccctatgg cacgccacat tatggcacat gcacgaatct catcaccagc     540
caagaagaag gtcctttttg                                                 560

<210> SEQ ID NO 28
<211> LENGTH: 315
<212> TYPE: PRT
<213> ORGANISM: Pepper

<400> SEQUENCE: 28

Met Ala Ala Glu Ile Ser Ile Ser Ala Ser Ser Arg Ala Ile Cys Leu
1               5                   10                  15

Gln Arg Asn Pro Phe Pro Ala Pro Lys Tyr Phe Ala Thr Ala Pro Pro
            20                  25                  30

Leu Leu Phe Phe Ser Pro Leu Thr Cys Asn Leu Asp Ala Ile Leu Arg
        35                  40                  45

Ser Arg Arg Lys Pro Arg Leu Ala Ala Cys Phe Val Leu Lys Asp Asp
    50                  55                  60

Lys Leu Tyr Thr Ala Gln Ser Gly Lys Gln Ser Asp Thr Glu Ala Ile
65                  70                  75                  80

Gly Asp Glu Ile Glu Val Glu Thr Asn Glu Lys Ser Leu Ala Val
                85                  90                  95

Arg Leu Ala Glu Lys Phe Ala Arg Lys Lys Ser Glu Arg Phe Thr Tyr
            100                 105                 110

Leu Val Ala Ala Val Met Ser Ser Leu Gly Ile Thr Ser Met Ala Val
        115                 120                 125

Ile Ser Val Tyr Tyr Arg Phe Ser Trp Gln Met Glu Gly Gly Glu Met
    130                 135                 140

Pro Phe Ser Glu Met Phe Cys Thr Phe Ala Leu Ala Phe Gly Ala Ala
```

```
                145                 150                 155                 160
        Ile Gly Met Glu Tyr Trp Ala Arg Trp Ala His Arg Ala Leu Trp His
                        165                 170                 175

Ala Ser Leu Trp His Met His Glu Ser His His Arg Pro Arg Glu Gly
                        180                 185                 190

Pro Phe Glu Leu Asn Asp Ile Phe Ala Ile Ile Asn Ala Val Pro Ala
                        195                 200                 205

Ile Ala Phe Phe Ser Phe Gly Phe Asn His Lys Gly Leu Ile Pro Gly
                210                 215                 220

Ile Cys Phe Gly Ala Gly Leu Gly Ile Thr Val Phe Gly Met Ala Tyr
        225                 230                 235                 240

Met Phe Val His Asp Gly Leu Val His Lys Arg Phe Pro Val Gly Pro
                        245                 250                 255

Ile Ala Lys Val Pro Tyr Phe Gln Arg Val Ala Ala His Gln Leu
                        260                 265                 270

His His Ser Asp Lys Phe Asp Gly Val Pro Tyr Gly Leu Phe Leu Gly
                        275                 280                 285

Pro Lys Glu Leu Glu Glu Val Gly Val Ile Glu Glu Leu Glu Lys Glu
                        290                 295                 300

Val Asn Arg Arg Ile Lys Ser Leu Lys Arg Leu
        305                 310                 315

<210> SEQ ID NO 29
<211> LENGTH: 945
<212> TYPE: DNA
<213> ORGANISM: Pepper

<400> SEQUENCE: 29
atggctgctg aaatttcaat ctccgctagc tcccgtgcca tttgtctcca gcgcaacccc      60
tttcctgctc caaaatactt tgcaactgcc ccgccacttc tcttcttctc tcctttaact     120
tgtaatctcg acgcaatttt gcggtctcgg agaaagccta ggttggctgc ttgctttgtg     180
ctgaaggatg acaaattgta tactgcacaa gtggaaaac aaagcgatac tgaagcaata     240
ggtgatgaga ttgaagtaga gactaatgag gagaagagtt tagctgtcag gctggccgaa     300
aaatttgcga ggaagaagtc agagaggttt acttatcttg tagctgcggt aatgtccagt     360
ttggggatta cttctatggc ggttatttca gtttattaca gatttcgtg gcaaatggaa     420 ggtggagaaa tgccttttc tgaaatgttt tgtacattcg ctctcgcctt tggcgctgcc     480
ataggaatgg agtactgggc gagatgggcg catagagcac tatggcatgc ttctttgtgg     540
catatgcacg agtcacacca tagaccaagg gaaggacctt tcgagctgaa cgatattttt     600
gccataatca atgctgttcc agctatagct tttttttcat tcggtttcaa ccataaaggc     660
cttatccctg gaatatgttt tggcgctgga ttagggatta cagtatttgg gatggcctac     720
atgtttgttc acgatggatt agttcacaag agattcccg tgggacccat tgccaaagta     780
cattattttc agagagtagc tgcagcacat cagcttcatc actcggacaa atttgatggg     840
gtcccatatg gcttgttcct aggacctaag gaattggaag aagtagggt aattgaagag     900 ttggaaaagg aagttaaccg aagaattaaa agtttgaaga gatta                      945

<210> SEQ ID NO 30
<211> LENGTH: 334
<212> TYPE: PRT
<213> ORGANISM: Pine

<400> SEQUENCE: 30
```

```
Met Gly Leu Arg Ser Val Ser Pro Tyr Gly Leu Ser Lys Cys Asp
1               5                   10                  15

Ser Ile Leu Ser Pro Pro Leu Ser Ser Thr Lys Pro Ala Ala Pro
            20                  25                  30

Leu Gly Arg Ala Val Tyr Cys Tyr Leu Ala Leu Ala Arg Ala Ser
        35                  40                  45

Ser Val Asn Arg Asn Gly Phe Arg Ser Ala Arg Val Phe Ser Glu Phe
50                  55                  60

Arg Gly Arg Arg Lys Val Leu Ser Leu Val Phe Ala Ser Thr Lys Lys
65                  70                  75                  80

Ser Gln Gln Leu Glu Met Lys Ser Glu Ser Ile Glu Asp Asp Ala Ser
                85                  90                  95

Ala Thr Glu Phe Ala Asp Ser Leu Ser Ser Arg Val Asp Glu Ile Ala
                100                 105                 110

Asn Lys Arg Glu Arg Asp Lys Arg Ala Ala Thr Arg Lys Ser Glu Arg
                115                 120                 125

His Ala Tyr Phe Phe Ala Ala Val Ala Ser Ser Val Gly Ile Thr Ser
                130                 135                 140

Met Thr Ala Ala Ala Val Tyr Tyr Arg Phe Val Trp Gln Met Gln Gly
145                 150                 155                 160

Ala Gln Ile Pro Tyr Met Glu Ile Phe Gly Thr Phe Ala Leu Ala Val
                165                 170                 175

Gly Ala Thr Val Gly Met Glu Phe Trp Ala Arg Trp Ala His Arg Ala
                180                 185                 190

Leu Trp His Ala Ser Leu Trp His Met His Glu Ser His His Arg Pro
                195                 200                 205

Arg Glu Gly Pro Phe Glu Leu Asn Asp Val Phe Ala Ile Ile Asn Ala
210                 215                 220

Phe Pro Ala Ile Ala Leu Met Ala Tyr Gly Phe Phe Asn Lys Gly Phe
225                 230                 235                 240

Val Pro Gly Leu Cys Phe Gly Ala Gly Leu Gly Ile Thr Val Phe Gly
                245                 250                 255

Met Ala Tyr Met Phe Val His Asp Gly Leu Val His Arg Arg Phe Pro
                260                 265                 270

Val Gly Pro Ile Ala Asp Val Pro Tyr Leu Leu Lys Val Ala Ala Ala
                275                 280                 285

His Gln Leu His His Ala Asp Lys Phe Asn Gly Val Pro Tyr Gly Leu
                290                 295                 300

Phe Leu Gly Pro Lys Glu Leu Glu Glu Val Gly Gly His Asp Glu Leu
305                 310                 315                 320

Glu Lys Leu Phe Asn Ser Lys Met Lys Gly Leu Gln Lys His
                325                 330
```

<210> SEQ ID NO 31
<211> LENGTH: 1004
<212> TYPE: DNA
<213> ORGANISM: Pine

<400> SEQUENCE: 31

```
atggggctga ggagtgtttc atctccatac ggattgtcaa agtgcgattc gatcctctca      60
cctccgcttt catcaaccaa accagctgca gcaccactgg gcagggcggt ttattgttat    120
tatctcgcgc ttgccagagc ttcttcagtt aacagaaatg ggttccgttc tgcccgcgtt    180
ttttctgaat tcgtgggag aaggaaggtg ctgtctctag tctttgcgtc gactaaaaaa    240
```

```
tcccaacagc tagagatgaa atcagaatcc attgaagatg atgcttctgc tactgaattt    300
gcagactcat taagcagtag agttgatgag attgcgaata aaagggaacg ggataaaaga    360
gctgcgacga ggaagtccga acgccatgcc tacttctttg ctgccgttgc ctccagtgtt    420
ggtattacta gtatgactgc cgctgctgtt tactaccgat tgtttggca gatgcagggt     480
gcacagattc cctacatgga gatctttgga acttttgcat tagcagtggg agccacggtt    540
ggaatggaat tttgggcacg ttgggctcac cgagctctat ggcacgcctc cttgtgcac    600
atgcatgagt ctcatcaccg gccaagggag ggacctttg agttgaatga tgtgttcgca    660
atcatcaatg cttttcctgc cattgcacta atggcttatg gattctttaa caaaggcttt    720
gtgccaggtc tttgctttgg tgctgggctt ggtatcaccg ttttggggat ggcatatatg    780
tttgtccatg atgggcttgt tcatcgccgc tttcctgttg gacctattgc tgatgttcca    840
tatcttctta aagtagctgc tgcacatcag cttcatcatg cagataagtt taatggtgtg    900
ccttatggtc ttttccttgg accaaaagaa ctggaagagg ttgggggcca tgacgagcta    960
gaaaaattgt ttaatagtaa gatgaagggc ctccaaaagc acta                    1004
```

<210> SEQ ID NO 32
<211> LENGTH: 292
<212> TYPE: PRT
<213> ORGANISM: Rice

<400> SEQUENCE: 32

```
Met Ala Val Ala Arg Leu Val Val Ile Thr Pro Ala Val Leu Leu Gly
1               5                   10                  15

Arg Thr Ala Arg Val Ser Pro Ser Ala Val Pro Arg Leu Arg Pro Ile
            20                  25                  30

Val Ala Gly Arg Arg Ala Val Ala Ala Pro Thr Arg Ala Val Leu Gly
        35                  40                  45

Asp Gly Ala Gly Val Gly Gly Glu Asp Ala Val Val Ala Val Val
    50                  55                  60

Glu Glu Asp Ala Val Ala Arg Arg Ala Ala Arg Lys Arg Ser Glu Arg
65                  70                  75                  80

Arg Thr Tyr Leu Val Ala Ala Val Met Ser Ser Leu Gly Phe Thr Ser
                85                  90                  95

Met Ala Ala Ala Val Tyr Tyr Arg Phe Ala Trp Gln Met Glu Ala
            100                 105                 110

Gly Gly Gly Asp Val Pro Ala Thr Glu Met Val Gly Thr Phe Ala Leu
        115                 120                 125

Ser Val Gly Ala Ala Val Gly Met Glu Phe Trp Ala Arg Trp Ala His
    130                 135                 140

Arg Ala Leu Trp His Ala Ser Leu Trp His Met His Glu Ser His His
145                 150                 155                 160

Arg Pro Arg Asp Gly Pro Phe Glu Leu Asn Asp Val Phe Ala Ile Ala
                165                 170                 175

Asn Ala Ala Pro Ala Ile Ser Leu Leu Ala Tyr Gly Leu Leu Asn Arg
            180                 185                 190

Gly Leu Leu Pro Gly Leu Cys Phe Gly Ala Gly Leu Gly Ile Thr Leu
        195                 200                 205

Phe Gly Met Ala Tyr Met Phe Val His Asp Gly Leu Val His Arg Arg
    210                 215                 220

Phe Pro Val Gly Pro Ile Glu Asn Val Pro Tyr Phe Arg Arg Val Ala
225                 230                 235                 240
```

Ala Ala His Gln Ile His His Thr Asp Lys Phe Glu Gly Val Pro Tyr
              245                 250                 255

Gly Leu Phe Leu Gly Pro Lys Glu Leu Glu Val Gly Gly Thr Glu
          260                 265                 270

Glu Leu Asp Lys Glu Ile Lys Lys Arg Ile Lys Arg Lys Glu Ala Met
        275                 280                 285

Asp Ala Ile Arg
    290

<210> SEQ ID NO 33
<211> LENGTH: 876
<212> TYPE: DNA
<213> ORGANISM: Rice

<400> SEQUENCE: 33

```
atggccgtcg cgaggctggt ggtcatcacc cccgccgtcc tcctcggccg caccgcccgc    60
gtctcgccgt cggcggtgcc gcggctgcgg cccatcgtcg ccggccgccg cgccgtggcg   120
gcgcccacac gcgccgtcct gggagacggg gcgggtgtcg gcggcgagga ggatgcggtg   180
gtggcggtgg tggaggagga gcggtcgcc cggcgcgcgg cgaggaagcg gtcggagcgg   240
cgcacgtacc tggtggcggc ggtgatgtcc agcctcgggt tcacgtccat ggccgccgcc   300
gccgtctact accgcttcgc ctggcaaatg gaggccggcg gcggcgacgt tccggcgacg   360
gagatggtcg gcacgttcgc gttgtcggtg ggggcggcgg tggggatgga gttctgggcg   420
cggtgggcgc accgggcgct gtggcacgcg tcgctgtggc acatgcacga gtcgcaccac   480
cgcccgcgcg acggcccgtt cgagctcaac gacgtcttcg ccatcgccaa cgccgccccg   540
gccatctccc tcctcgccta cggcctcctc aaccgcggcc tcctccccgg cctctgcttc   600
ggcgcggggc ttgggattac gctgttcggg atggcgtaca tgttcgtcca cgacggcctg   660
gtccaccggc gcttccccgt ggggcccatc gagaacgtgc cctacttccg ccagttgct   720
gccgccccacc agatacatca cacggacaag ttcgaaggcg tgccctacgg cctgttcctc   780
ggacccaagg agttggagga ggtgggtggg actgaggagc tggacaagga gatcaagaag   840
aggatcaaga ggaaggaggc catggacgcc atcaga                              876
```

<210> SEQ ID NO 34
<211> LENGTH: 239
<212> TYPE: PRT
<213> ORGANISM: Sorghum

<400> SEQUENCE: 34

Thr Pro Gly Ser Arg Ser Pro Gly Ser Leu Ser Cys Pro Ser Ile Ala
1                 5                  10                  15

Phe His Trp Lys Val Gln Ala Arg Ala His Gly Arg Arg Ser Val Arg
              20                  25                  30

Arg Arg Asp Asp Arg Val Arg Arg Gln Glu Pro Ala Ala Arg Gly Arg
          35                  40                  45

Gly Arg Gly Ala Pro Gln Gly Ala Ser Thr Cys Arg Ala Arg Pro Ala
      50                  55                  60

Val Leu Ala Ala His His Gln Gly Arg Ala Pro Pro Arg Ala Arg
65                  70                  75                  80

Asp Arg His Val Leu Arg Ala Ala Arg His Gly Ala Pro Gly Gly Pro
              85                  90                  95

Gly Pro Gly Cys Ser Gly Ala Gly Ala Gly Ala Gly Asp Gly Ala Gly
          100                 105                 110

Arg Gly Gly Gln Gly Arg Gly Ala Ala His Arg Gly Glu Glu Gly
        115                 120                 125

Ala Glu Ala Val Arg Ala Ser Asp Val Pro Gly Arg His Asp Val
130                 135                 140

Gln Pro Arg Val His Val His Gly Arg Arg Arg Val Leu Ser Leu
145                 150                 155                 160

Gln Leu Ala Asn Gly Arg Arg Gly Ala Gly Glu Arg Asp Val Gly
            165                 170                 175

His Val Arg Ala Leu Arg Arg Gly Gly Arg Asp Gly Val Leu Gly
        180                 185                 190

Ala Val Gly Ala Pro Gly Ala Val Ala Arg Leu Pro Val Ala His Ala
        195                 200                 205

Arg Val Ala Pro Pro Ala Ala Gly Gly Pro Leu Arg Ala Gln Arg Arg
    210                 215                 220

Val Arg His His Gln Arg Arg Ala Gly His Leu Ser Pro Arg Leu
225                 230                 235

<210> SEQ ID NO 35
<211> LENGTH: 717
<212> TYPE: DNA
<213> ORGANISM: Sorghum

<400> SEQUENCE: 35
actcccggct cccgctcgcc cgggtccctg tcctgtccat ctatagcgtt ccattggaaa      60
gtgcaagcac gggcccatgg ccgccggtct gtccggcgcc gcgatgaccg ggttcgtcgc     120
caagaacccg ctgctcgcgg ccgcggccgc ggcgcgccgc agggcgcatc cacttgccgg     180
gcgcgccctg ccgttctcgc cgctcaccac caccagggcc gcgcgccgcc gcgggctcgg     240
gaccgtcacg tgcttcgtgc cgccagacac ggagcacccg gcggcccggg ccccggctgc     300
tccggtgccg gtgccggtgc cggagacggg gctggacgag gaggccaggg ccgcggcggc     360
gcggcgcatc gcggagaaga aggcgcggaa gcggtccgag cgtcggacgt acctggtggc     420
cgccatgatg tccagcctcg ggttcacgtc catggccgtc gccgccgtgt actctcgctt     480
cagctggcaa atggagggcg cgaggtgcc ggtgagcgag atgttgggca cgttcgcgct     540
ctccgtcggc gcggcggtcg ggatggagtt ctgggcgcgg tgggcgcacc gggcgctgtg     600
gcacgcctcc ctgtggcaca tgcacgagtc gcaccaccgg ccgcgggagg gccccttcga     660
gctcaacgac gtgttcgcca tcatcaacgc cgtgccggcc atctgtctcc tcgccta       717

<210> SEQ ID NO 36
<211> LENGTH: 127
<212> TYPE: PRT
<213> ORGANISM: Sandersonia aurantiaca

<400> SEQUENCE: 36

Leu Glu Phe Trp Ala Arg Trp Ala His Arg Ala Leu Trp His Ala Ser
1               5                   10                  15

Leu Trp His Met His Glu Ser His His Arg Ala Arg Glu Gly Pro Phe
            20                  25                  30

Glu Leu Asn Asp Val Phe Ala Ile Thr Asn Ala Val Pro Ala Ile Ala
        35                  40                  45

Leu Leu Ser Tyr Gly Phe Phe His Arg Gly Leu Leu Pro Gly Leu Cys
    50                  55                  60

Phe Gly Ala Gly Leu Gly Ile Thr Leu Phe Gly Met Ala Tyr Met Phe
65                  70                  75                  80

```
Val His Asp Gly Leu Val His Arg Arg Phe Pro Val Gly Pro Ile Ala
                85                  90                  95

Asn Val Pro Tyr Phe Gln Arg Val Ala Ala His Gln Ile His His
            100                 105                 110

Met Asp Lys Phe Glu Gly Val Pro Tyr Gly Leu Phe Met Gly Pro
        115                 120                 125
```

<210> SEQ ID NO 37
<211> LENGTH: 381
<212> TYPE: DNA
<213> ORGANISM: Sandersonia aurantiaca
<220> FEATURE:
<221> NAME/KEY: misc_feature
<222> LOCATION: (90)..(90)
<223> OTHER INFORMATION: n is a, c, g, or t

<400> SEQUENCE: 37

```
ttggagttct gggcgagatg ggcgcaccgg gcgctgtggc acgcgtcgct gtggcatatg      60
cacgagtcgc accaccgggc gagggagggn ccgttcgagc tcaacgacgt cttcgccatc     120
acgaacgccg tccctgcgat cgcgctccta tcgtatggat tcttccatcg cggcctcctt     180
cctggactct gcttcggagc tgggctgggg attacgctgt cgggatggc gtacatgttc      240
gtccacgacg ggctggtgca caggaggttc ccggtgggc ccatcgccaa cgtgccctac      300
ttccagagag tcgcggcggc tcatcagatc caccacatgg acaagtttga aggggtgcct     360
tatgggctgt tcatgggtcc c                                               381
```

<210> SEQ ID NO 38
<211> LENGTH: 334
<212> TYPE: PRT
<213> ORGANISM: Soybean

<400> SEQUENCE: 38

```
Met Gly Asp Arg Gly Ser Ser His Ser Leu Leu Ala Gly Glu His Lys
1               5                   10                  15

His Ser Leu Phe Ala Ser Trp Arg Asn Ser Ile Glu Ala Ile Tyr Pro
            20                  25                  30

Ser Met Ala Ala Gly Leu Pro Thr Ala Ala Ile Leu Lys Pro Tyr Asn
        35                  40                  45

Leu Val Gln Pro Pro Ile Pro Leu Ser Lys Pro Thr Thr Ser Leu Phe
    50                  55                  60

Phe Asn Pro Leu Arg Cys Phe His His Ser Thr Ile Leu Arg Val Arg
65                  70                  75                  80

Pro Arg Arg Arg Met Ser Gly Phe Thr Val Cys Val Leu Thr Glu Asp
                85                  90                  95

Ser Lys Glu Ile Lys Thr Val Glu Gln Glu Gln Glu Val Ile Pro
            100                 105                 110

Gln Ala Val Ser Ala Gly Val Ala Glu Lys Leu Ala Arg Lys Lys Ser
        115                 120                 125

Gln Arg Phe Thr Tyr Leu Val Ala Val Met Ser Ser Phe Gly Ile
    130                 135                 140

Thr Ser Met Ala Val Phe Ala Val Tyr Tyr Arg Phe Ser Trp Gln Met
145                 150                 155                 160

Glu Gly Gly Asp Val Pro Trp Ser Glu Met Leu Gly Thr Phe Ser Leu
                165                 170                 175

Ser Val Gly Ala Ala Val Ala Met Glu Phe Trp Ala Arg Trp Ala His
            180                 185                 190
```

Arg Ala Leu Trp His Ala Ser Leu Trp His Met His Glu Ser His His
        195                 200                 205

Arg Pro Arg Glu Gly Pro Phe Glu Leu Asn Asp Val Phe Ala Ile Ile
        210                 215                 220

Asn Ala Val Pro Ala Ile Ala Leu Leu Ser Tyr Gly Ile Phe His Lys
225                 230                 235                 240

Gly Leu Val Pro Gly Leu Cys Phe Gly Ala Gly Leu Gly Ile Thr Val
                245                 250                 255

Phe Gly Met Ala Tyr Met Phe Val His Asp Gly Leu Val His Lys Arg
                260                 265                 270

Phe Pro Val Gly Pro Ile Ala Asn Val Pro Tyr Phe Arg Arg Val Ala
                275                 280                 285

Ala Ala His Gln Leu His His Ser Asp Lys Phe Asn Gly Ala Pro Tyr
            290                 295                 300

Gly Leu Phe Leu Gly Pro Lys Glu Val Glu Glu Val Gly Gly Leu Glu
305                 310                 315                 320

Glu Leu Glu Lys Glu Ile Ser Arg Arg Ile Arg Ser Gly Ser
                325                 330

<210> SEQ ID NO 39
<211> LENGTH: 1125
<212> TYPE: DNA
<213> ORGANISM: Soybean

<400> SEQUENCE: 39

| | | | | | |
|---|---|---|---|---|---|
| atggcggcag | gactctccac | cgccgcaatc | ttaaagccct | acaatctcgt | ccaaccccca | 60 |
| atccctcttt | ctaaaccaac | cacatcactc | ttcttcaacc | ccttaagatg | tttccatcac | 120 |
| agtacaatcc | ttcgagttcg | acccagaaga | agaatgagcg | gcttcaccgt | ttgcgtcctc | 180 |
| acggaggatt | ccaaagagat | caaaacggtc | gaacaagaac | aagaacaagt | gattcctcaa | 240 |
| gccgtgtcag | caggtgtggc | agagaagttg | gcgagaaaga | agtcccagag | gttcacttat | 300 |
| ctcgttgcgg | ctgtcatgtc | tagctttggc | atcacctcta | tggcagtctt | tgccgtttat | 360 |
| tatagattct | cctggcaaat | ggagggtgga | gatgttcctt | ggtctgaaat | gctaggcaca | 420 |
| ttttccctct | ccgtcggtgc | tgctgtggct | atggaatttt | gggcaagatg | ggctcataga | 480 |
| gctctttggc | atgcttcctt | gtggcacatg | cacgagtcac | accatcgacc | aagagaggga | 540 |
| ccgttcgagc | ttaacgacgt | ttttgcgata | attaacgctg | tccctgcgat | cgttcttctc | 600 |
| tcatacggtt | ttttccacaa | gggtctggtc | cctggcctct | gttttggtgc | aggccttgga | 660 |
| atcacggtgt | ttgggatggc | ctacatgttt | gtccacgatg | gattggttca | taagagattc | 720 |
| cctgtgggtc | ccattgccaa | cgtgccctac | tttagaagag | ttgctgctgc | tcaccaactc | 780 |
| caccattcgg | acaaattcaa | cggggtgcca | tatggcttgt | ttttgggacc | aaaggaagtt | 840 |
| gaagaagtgg | gagggctaga | agagctagag | aaagagataa | gtaggagaat | caggtccggt | 900 |
| tcatgaccat | gccactggta | ttagctagac | ttgtttgaaa | gaattgaggg | tagagaaagg | 960 |
| gaaacaattc | aattaatgaa | tgaaatgatt | tgaatctttt | ttttttcttt | catacagcta | 1020 |
| ttcatattat | aatagcagag | catataacag | aaaaataggg | ttaaacgttt | atagatgtat | 1080 |
| aaacagatca | aacatgtgtc | aatggaaatg | ttctaattgc | agcat | | 1125 |

<210> SEQ ID NO 40
<211> LENGTH: 309
<212> TYPE: PRT
<213> ORGANISM: Tomato

<400> SEQUENCE: 40

| | | | | | | | | | | | | | | |
|---|---|---|---|---|---|---|---|---|---|---|---|---|---|---|
|Met|Ala|Ala|Ala|Ala|Arg|Ile|Ser|Ala|Ser|Thr|Ser|Arg|Thr|Phe|
|1| | | |5| | | | |10| | | | |15|
|Tyr|Phe|Arg|His|Ser|Pro|Phe|Leu|Gly|Pro|Lys|Pro|Thr|Ser|Thr|Thr|
| | | |20| | | | |25| | | | |30| | |
|Ser|His|Val|Ser|Pro|Ile|Ser|Pro|Phe|Ser|Leu|Asn|Leu|Gly|Pro|Ile|
| | | |35| | | | |40| | | | |45| | |
|Leu|Arg|Ser|Arg|Arg|Lys|Pro|Ser|Phe|Thr|Val|Cys|Phe|Val|Leu|Glu|
| |50| | | | |55| | | | |60| | | | |
|Asp|Glu|Lys|Leu|Lys|Pro|Gln|Phe|Asp|Asp|Glu|Ala|Glu|Asp|Phe|Glu|
|65| | | | |70| | | | |75| | | | |80|
|Lys|Lys|Ile|Glu|Glu|Gln|Ile|Leu|Ala|Thr|Arg|Leu|Ala|Glu|Lys|Leu|
| | | | |85| | | | |90| | | | |95| |
|Ala|Arg|Lys|Lys|Ser|Glu|Arg|Phe|Thr|Tyr|Leu|Val|Ala|Ala|Ile|Met|
| | | | |100| | | | |105| | | | |110| |
|Ser|Ser|Phe|Gly|Ile|Thr|Ser|Met|Ala|Val|Met|Ala|Val|Tyr|Tyr|Arg|
| | | | |115| | | | |120| | | | |125| |
|Phe|Ser|Trp|Gln|Met|Glu|Gly|Gly|Glu|Val|Pro|Val|Thr|Glu|Met|Leu|
| | |130| | | | |135| | | | |140| | | |
|Gly|Thr|Phe|Ala|Leu|Ser|Val|Gly|Ala|Ala|Val|Gly|Met|Glu|Phe|Trp|
|145| | | | |150| | | | |155| | | | |160|
|Ala|Arg|Trp|Ala|His|Lys|Ala|Leu|Trp|His|Ala|Ser|Leu|Trp|His|Met|
| | | | |165| | | | |170| | | | |175| |
|His|Glu|Ser|His|His|Lys|Pro|Arg|Glu|Gly|Pro|Phe|Glu|Leu|Asn|Asp|
| | | |180| | | | |185| | | | |190| | |
|Val|Phe|Ala|Ile|Thr|Asn|Ala|Val|Pro|Ala|Ile|Ala|Leu|Leu|Asn|Tyr|
| | |195| | | | |200| | | | |205| | | |
|Gly|Phe|Phe|His|Lys|Gly|Leu|Ile|Ala|Gly|Leu|Cys|Phe|Gly|Ala|Gly|
| | |210| | | | |215| | | | |220| | | |
|Leu|Gly|Ile|Thr|Val|Phe|Gly|Met|Ala|Tyr|Met|Phe|Val|His|Asp|Gly|
|225| | | | |230| | | | |235| | | | |240|
|Leu|Val|His|Lys|Arg|Phe|Pro|Val|Gly|Pro|Val|Ala|Asn|Val|Pro|Tyr|
| | | | |245| | | | |250| | | | |255| |
|Leu|Arg|Lys|Val|Ala|Ala|Ala|His|Ser|Leu|His|His|Ser|Glu|Lys|Phe|
| | | |260| | | | |265| | | | |270| | |
|Asn|Gly|Val|Pro|Tyr|Gly|Leu|Phe|Phe|Gly|Pro|Lys|Glu|Leu|Glu|Glu|
| | | |275| | | | |280| | | | |285| | |
|Val|Gly|Gly|Thr|Glu|Glu|Leu|Glu|Lys|Glu|Val|Ile|Arg|Arg|Thr|Arg|
| |290| | | | |295| | | | |300| | | | |
|Leu|Ser|Lys|Gly|Ser| | | | | | | | | | | |
|305| | | | | | | | | | | | | | | |

<210> SEQ ID NO 41
<211> LENGTH: 927
<212> TYPE: DNA
<213> ORGANISM: Tomato

<400> SEQUENCE: 41
atggctgccg ccgccagaat ctccgcctcc tctacctcac gaactttta tttccgtcat     60 tcaccgtttc ttggcccaaa acctacttcg acaacctcac atgtttctcc aatctctcct    120
ttttctctta atctaggccc aattttgagg tctagaagaa acccagttt cactgtttgc     180 tttgttctcg aggatgagaa gctgaaacct caatttgacg atgaggctga ggattttgaa   240

```
aagaagattg aggaacagat cttagctact cgcttggcgg agaaactggc taggaagaaa    300
tcggagaggt ttacttatct tgtggctgct ataatgtcta gttttgggat tacttctatg    360
gctgttatgg ctgtttatta cagattttcg tggcaaatgg agggaggaga agttcctgta    420
accgaaatgt tgggtacatt tgctctctct gttggtgctg ctgtaggaat ggagttttgg    480
gcgagatggg cacacaaagc actgtggcat gcttcactat ggcacatgca tgagtcacac    540
cacaaaccaa gagaaggacc ttttgagctg aacgacgttt tcgccataac aaacgctgtt    600
ccagcaatag ccctcctcaa ctatggtttc ttccataaag gcctcattgc cggactatgc    660
ttcggtgctg ggctagggat cacagtattt ggaatggcat acatgtttgt tcacgatggt    720
ttggttcaca agagattccc agttggacct gtagccaatg taccttatct taggaaggtg    780
gctgctgctc attcgcttca tcactcagag aagttcaatg gtgtcccata tggcttgttc    840
ttcggaccta aggaactgga agaagtagga gggacggaag agttggaaaa ggaagtgata    900
cgaaggacga gactttcgaa aggatca                                        927
```

<210> SEQ ID NO 42
<211> LENGTH: 272
<212> TYPE: PRT
<213> ORGANISM: Wheat

<400> SEQUENCE: 42

```
Met Ala Val Ala Arg Arg Gly Ala Ala Pro Phe Pro Leu Ala Ala
1               5                   10                  15

Arg Ala Arg Gly Pro Arg Ala Arg Leu Leu Phe Ala Pro Leu Ser Ala
            20                  25                  30

Leu Pro Arg Arg Ala Ala Ala Pro Ala Met Arg Val Ala Ser Asp Gly
        35                  40                  45

Asn Gly Gly Gly Leu Val Pro Val Arg Pro Gly Gln Glu Ala Glu Asp
    50                  55                  60

Ala Ala Ala Thr Ala Arg Gly Ala Val Ser Asp Arg Ala Ala Arg Lys
65                  70                  75                  80

Glu Ser Glu Arg Arg Thr Tyr Leu Val Ala Ala Leu Met Ser Ser Leu
                85                  90                  95

Gly Ile Thr Ser Met Asp Gly Val Ala Val Tyr Tyr Arg Phe Ala Trp
            100                 105                 110

Glu Met Glu Gly Gly Glu Ile Pro Val Thr Glu Met Leu Gly Thr Leu
        115                 120                 125

Ala Leu Ser Val Gly Ala Ala Ala Gly Met Glu Phe Trp Ala Leu Cys
    130                 135                 140

Ala His Arg Ser Leu Trp His Ala Ser Met Trp Asp Met His Gln Phe
145                 150                 155                 160

His His Leu Pro Arg Glu Gly Pro Phe Gln Leu His Asp Val Phe Ala
                165                 170                 175

Ile Leu Asn Gly Val Pro Gly His Gly Pro Pro Trp Val Trp Val Phe
            180                 185                 190

Met Thr Gly Gly Ser Ala Pro Ser Tyr Val Arg Gly Pro Val Leu Gly
        195                 200                 205

Pro Pro Arg Ser Arg Met Gly Lys Leu Cys Val Pro His Gly Leu Gly
    210                 215                 220

Arg Pro Pro His Ser Pro Arg Gly Pro Leu Trp Asn Arg Pro His Phe
225                 230                 235                 240

Pro Gly Asn Leu Ala Gly Pro Ala Leu Val Ala Gly Gln Val Gln His
                245                 250                 255
```

Pro Ala Ser Gly Leu Phe Pro Pro Gln Pro Gln Val Ala Trp Arg Arg
            260                 265                 270

<210> SEQ ID NO 43
<211> LENGTH: 816
<212> TYPE: DNA
<213> ORGANISM: Wheat

<400> SEQUENCE: 43

```
atggccgtcg cgaggcgggg ggccgcgcca ttccccctcg ccgccgcccg cgcccgcggc      60
ccgcgggcgc ggctgctgtt cgcgccgctc tctgcgctcc ccgtcgcgc ggccgcgccc     120
gccatgcgcg tggcgtcaga cggcaacggc ggcggccttg tccccgtccg cccgggccag    180
gaggcggagg acgccgcggc gacggcgcgg ggcgcggtgt cggatcgcgc ggcgaggaag    240
gagtcggagc ggcggacgta cctggtggcc gcgctcatgt ccagcctcgg catcacctcc    300
atggacggcg tcgccgtcta ctaccgattc gcctgggaaa tggagggcgg cgagattccg    360
gtgacggaga tgctgggcac cttggcactc tccgtgggcg cggcggcggg gatggagttc    420
tgggcgctgt gtgcgcaccg ctcgctgtgg cacgcgtcga tgtgggacat gcaccaattc    480
caccaccttc cccgcgaagg gcccttcag cttcacgacg tgttcgccat tctaaacggc    540
gtacccggcc atggccctcc ctgggtttgg gtttttatga ctgggggctc cgccccgtct    600
tatgttcggg gccggtcttt ggaccccccc cggtcgcgaa tggcaaaact ttgcgtcccc    660
cacgggcttg gtcgaccgcc ccactccccc aggggggccc tgtggaaccg tccccacttc    720
ccgggaaatc ttgcggggcc agcgttggtc gctggacagg ttcagcatcc ggcatccggg    780
ctcttccccc cccaaccaca agtagcgtgg cggcgg                              816
```

<210> SEQ ID NO 44
<211> LENGTH: 286
<212> TYPE: PRT
<213> ORGANISM: Lettuce

<400> SEQUENCE: 44

Met Ala Ala Ala Ala Ile Ala Val Ala Ser Ser Arg Ser Phe Arg
1               5                   10                  15

Leu Thr Arg Met Pro Phe Leu Gly Gln Lys Pro Thr Ser Arg Thr Ser
            20                  25                  30

Gln Phe Pro Ser Ser Ile Arg Asn Phe Asp Pro Ile Ala Arg Phe Arg
            35                  40                  45

Arg Thr Pro Arg Leu Thr Val Cys Phe Ala Gly Asp Gln Lys Leu
        50                  55                  60

Glu Thr Gln Ile Val Glu Asp Asn Gly Ser Gly Asn Asn Pro Gly Pro
65                  70                  75                  80

Ser Gly Gly Glu Gly Ser Asp Glu Gly Ile Thr Gln Val Met Leu Ser
                85                  90                  95

Ser Thr Ser Asn Arg Val Val Glu Glu Lys Met Ala Arg Lys Lys Ser
            100                 105                 110

Glu Arg Phe Thr Tyr Leu Val Ala Ala Ile Met Ser Thr Phe Gly Ile
        115                 120                 125

Thr Ser Met Ala Val Met Ala Val Tyr Tyr Arg Phe Ser Trp Gln Met
    130                 135                 140

Glu Gly Gly Asp Val Pro Phe Val Glu Met Phe Gly Thr Phe Ala Leu
145                 150                 155                 160

Ser Val Gly Ala Ala Val Gly Met Glu Tyr Trp Ala Arg Trp Ala His

```
              165                 170                 175
Glu Ala Leu Trp His Ala Ser Leu Trp His Thr His Glu Ser His His
            180                 185                 190

Lys Pro Arg Glu Gly Pro Phe Glu Leu Asn Asp Val Phe Ala Ile Ile
            195                 200                 205

Asn Ala Val Pro Ala Ile Ala Leu Leu Asn Tyr Gly Phe Phe His Lys
        210                 215                 220

Gly Ile Phe Pro Gly Leu Cys Phe Gly Ala Gly Leu Gly Ile Thr Val
225                 230                 235                 240

Phe Gly Met Ala Tyr Met Phe Val His Asp Gly Leu Val His Arg Arg
                245                 250                 255

Phe Gln Val Gly Pro Ile Ala Asn Val Pro Tyr Leu Arg Arg Val Ala
            260                 265                 270

Ala Ala His Gln Leu His His Thr Glu Glu Phe Asn Gly Val
            275                 280                 285

<210> SEQ ID NO 45
<211> LENGTH: 859
<212> TYPE: DNA
<213> ORGANISM: Lettuce

<400> SEQUENCE: 45
atggcggcag cagcaatcgc cgtcgcttcc agttcacgct ccttccgttt aacccgaatg     60
ccgttcctag gtcaaaaacc cacatctaga acttctcaat ttccatcctc tatcagaaac    120
ttcgacccga ttgctcggtt ccgacggacg cctaggttga cagtctgttt cgttgccgga    180
gaccagaagt tagagaccca aattgttgag acaacggca gtggtaacaa tcctggacct     240
agcggcggcg agggttcaga tgaggaaata actcaggtga tgttgagtag tactagtaac    300
cgcgtcgtag aggaaaaaat ggctaggaag aagtccgaac gctttactta ccttgtcgca    360
gctatcatgt ctacttttgg gattacttcc atggctgtta ggctgtttta ttacaggttt    420
tcatggcaaa tggagggtgg agatgttcct tttgtggaga tgtttgggac atttgctctc    480
tctgttggcg ctgcggtagg aatggagtat tgggcgagat gggcgcatga agctctatgg    540
catgcttctt tatggcacac gcatgagtca caccataaac cccgagaagg ccccttcgag    600
ctcaacgacg tgttcgcgat tataaacgcc gttccggcga ttgcgttact gaactacggc    660
ttcttccata aggaatatt tcccggcctc tgtttcggcg ctgggcttgg ataacggtg      720 tttggaatgg cgtacatgtt cgtccacgat ggccttgttc ataggagatt ccaagtgggt    780
cccattgcaa atgtccccta ccttcgaaga gttgcagctg ctcatcagtt gcatcacaca    840
gaagaattta tgggtac                                                   859

<210> SEQ ID NO 46
<211> LENGTH: 61
<212> TYPE: DNA
<213> ORGANISM: Artificial
<220> FEATURE:
<223> OTHER INFORMATION: Linker segment

<400> SEQUENCE: 46
atctacccgc ttcgcgtcgg catccggtca tggcagtgaa gggccaacag ttcctgatta     60
a                                                                    61
```

<210> SEQ ID NO 47
<211> LENGTH: 17
<212> TYPE: DNA
<213> ORGANISM: Artificial
<220> FEATURE:
<223> OTHER INFORMATION: Forward primer

<400> SEQUENCE: 47
gggtggagag gctattc                                                    17

<210> SEQ ID NO 48
<211> LENGTH: 17
<212> TYPE: DNA
<213> ORGANISM: Artificial
<220> FEATURE:
<223> OTHER INFORMATION: Reverse primer

<400> SEQUENCE: 48
gaaggcgata gaaggcg                                                    17

<210> SEQ ID NO 49
<211> LENGTH: 88
<212> TYPE: DNA
<213> ORGANISM: Solanum tuberosum

<400> SEQUENCE: 49
tctctccttt ttctcctaat ctaggcccaa ttctgaggtc tagaagaaaa cccagtttca     60
ctgtttgctt tgttctcgag gatgagaa                                        88

<210> SEQ ID NO 50
<211> LENGTH: 88
<212> TYPE: DNA
<213> ORGANISM: Solanum tuberosum

<400> SEQUENCE: 50
tctctccgtt aactcgcaat tttggcgcaa ttttgctgtc tcgaagaaag ccgaggttgg     60 cggttttgctt tgtgctgaag aatgagaa                                       88

<210> SEQ ID NO 51
<211> LENGTH: 308
<212> TYPE: DNA
<213> ORGANISM: Solanum tuberosum

<400> SEQUENCE: 51
tggtggaaaa attggctagg aagaaatcgg agaggtttac ttatcttgta gctgctgtaa    60
tgtctagttt tgggattact tctatggctg ttatggcggt ttattacaga ttttcgtggc    120
aaatggaggg tggagaagtt cctttaaccg aaatgttggg tacatttgct ctctctgttg    180
gtgctgctgt aggaatggag ttttgggcaa gatgggcaca caaagcattg tggcatgctt    240
cactatggca catgcacgag tcacatcaca aaccaagaga aggaccttt  gagctgaatg    300 acgttttc                                                              308

<210> SEQ ID NO 52
<211> LENGTH: 308
<212> TYPE: DNA
<213> ORGANISM: Solanum tuberosum -continued

```
<400> SEQUENCE: 52
tggcggaaaa attggcgagg aagaaatcgg agaggtttac ttatcttgtg gcggctgtca        60
tgtctagttt agggattact tctatggcga ttttgtcagt ttattacaga ttttcatggc       120
aaatggaggg tggagaagtg cctttttctg aaatgttagc tacattcact ctctcgtttg       180
gcgctgccgt aggaatggag tactgggcga gatgggctca tagagcacta tggcatgctt       240
ctttatggca catgcacgag tcacaccata gaccaagaga aggacctttt gagatgaacg       300
acgttttc                                                                308
```